(12) United States Patent
Pourfallah et al.

(10) Patent No.: US 8,939,356 B2
(45) Date of Patent: Jan. 27, 2015

(54) PORTABLE PRESCRIPTION PAYMENT DEVICE MANAGEMENT PLATFORM APPARAUTSES, METHODS AND SYSTEMS

(71) Applicant: Visa International Service Association, San Francisco, CA (US)

(72) Inventors: Stacy Pourfallah, San Ramon, CA (US); Karen Louise Cervenka, Woodside, CA (US)

(73) Assignee: Visa International Service Association, San Francisco, CA (US)

( * ) Notice: Subject to any disclaimer, the term of this patent is extended or adjusted under 35 U.S.C. 154(b) by 26 days.

(21) Appl. No.: 13/853,952

(22) Filed: Mar. 29, 2013

(65) Prior Publication Data

US 2013/0226609 A1 Aug. 29, 2013

Related U.S. Application Data

(63) Continuation-in-part of application No. 12/573,688, filed on Oct. 5, 2009, now Pat. No. 8,413,905, and a continuation-in-part of application No. 12/545,372, filed on Aug. 21, 2009, and a continuation-in-part of (Continued)

(51) Int. Cl.
*G06F 17/00* (2006.01)
*G06Q 50/22* (2012.01)
(Continued)

(52) U.S. Cl.
CPC ............ *G06Q 20/3474* (2013.01); *G06Q 50/22* (2013.01); *G06F 19/328* (2013.01);
(Continued)

(58) Field of Classification Search
USPC ................ 235/380, 487, 492, 375; 705/14.1, 705/13.37, 17
See application file for complete search history.

(56) References Cited

U.S. PATENT DOCUMENTS

| 4,491,725 A | 1/1985 | Pritchard |
| 5,018,067 A | 5/1991 | Mohlenbrock et al. |

(Continued)

FOREIGN PATENT DOCUMENTS

| JP | 2005124991 A | 5/2005 |
| JP | 2008545210 A | 12/2008 |

(Continued)

OTHER PUBLICATIONS

Convansys: From the Inside Out, "Companion Guide: 835 Health Care Claim Payment/Advice," XP002564865, http://www.njelkids.com/UL/pdf/NJ_835v1_20040820-2.pdf, Jun. 24, 2004, 20 pages.

(Continued)

*Primary Examiner* — Seung Lee
(74) *Attorney, Agent, or Firm* — Loeb & Loeb LLP

(57) ABSTRACT

The PORTABLE PRESCRIPTION PAYMENT DEVICE MANAGEMENT PLATFORM APPARATUSES, METHODS AND SYSTEMS ("PPD") provides a portable coupon payment device includes a substrate having surface with an image rendering thereon that corresponds to a free sample. The portable coupon payment device also has memory, in contact with the substrate, having data encoded therein including (i) an identifier for the free sample, (ii) a quantity for the free sample; (iii) a sponsor company account for a selling merchant to charge the cost of the free sample for payment to a selling merchant account to reimburse the selling merchant for the free sample; (iv) an image corresponding to the free sample; and (v) an identifier for a coupon provider donating the free sample to a consumer.

20 Claims, 8 Drawing Sheets

Related U.S. Application Data application No. 12/480,268, filed on Jun. 8, 2009, and a continuation-in-part of application No. 12/480,346, filed on Jun. 8, 2009, and a continuation-in-part of application No. 12/480,444, filed on Jun. 8, 2009, and a continuation-in-part of application No. 12/480,529, filed on Jun. 8, 2009, and a continuation-in-part of application No. 12/480,551, filed on Jun. 8, 2009.

(51) Int. Cl.
*G06F 19/00* (2011.01)
*G06Q 20/34* (2012.01)
*G06Q 30/04* (2012.01)
*G06Q 99/00* (2006.01)
*G07F 17/00* (2006.01)
*G06Q 20/38* (2012.01)
*G06Q 30/02* (2012.01)

(52) U.S. Cl.
CPC .......... *G06Q20/3415* (2013.01); *G06Q 20/346* (2013.01); *G06Q 30/04* (2013.01); *G06Q 99/00* (2013.01); *G07F 17/0014* (2013.01); *G07F 17/0092* (2013.01); *G06Q 20/387* (2013.01); *G06Q 30/0241* (2013.01); *G06F 19/323* (2013.01); *G06F 19/3456* (2013.01)
USPC ........................................................ 235/375

(56) References Cited

U.S. PATENT DOCUMENTS

| | | |
|---|---|---|
| 5,070,452 A | 12/1991 | Doyle, Jr. et al. |
| 5,175,416 A | 12/1992 | Belamant et al. |
| 5,235,507 A | 8/1993 | Levin et al. |
| 5,301,105 A | 4/1994 | Cummings, Jr. |
| 5,324,077 A | 6/1994 | Kessler et al. |
| 5,335,278 A | 8/1994 | Birch et al. |
| 5,550,734 A | 8/1996 | De Fazio et al. |
| 5,628,530 A | 5/1997 | Thornton |
| 5,644,778 A | 7/1997 | Burks et al. |
| 5,710,578 A | 1/1998 | Beauregard et al. |
| 5,832,447 A | 11/1998 | Mansfield et al. |
| 5,915,241 A | 6/1999 | Giannini |
| 5,965,860 A | 10/1999 | Oneda |
| 5,995,939 A | 11/1999 | Asbell et al. |
| 6,012,035 A | 1/2000 | Freeman, Jr. et al. |
| 6,044,352 A | 3/2000 | Deavers |
| 6,082,776 A | 7/2000 | Feinberg |
| 6,112,183 A | 8/2000 | Gladding |
| 6,151,588 A | 11/2000 | Lynch et al. |
| 6,208,973 B1 | 3/2001 | Boyer et al. |
| 6,243,687 B1 | 6/2001 | Powell |
| 6,332,133 B1 | 12/2001 | Takayama |
| 6,343,271 B1 | 1/2002 | Peterson et al. |
| 6,401,079 B1 | 6/2002 | Kahn et al. |
| 6,529,884 B1 | 3/2003 | Jakobsson |
| 6,629,081 B1 | 9/2003 | Cornelius et al. |
| 6,850,901 B1 | 2/2005 | Hunter et al. |
| 6,877,655 B1 | 4/2005 | Robertson et al. |
| 6,915,265 B1 | 7/2005 | Johnson |
| 6,988,075 B1 | 1/2006 | Hacker |
| 7,072,842 B2 | 7/2006 | Provost |
| 7,174,302 B2 | 2/2007 | Patricelli |
| 7,295,988 B1 | 11/2007 | Reeves |
| 7,428,494 B2 | 9/2008 | Hasan |
| 7,752,096 B2 | 7/2010 | Santalo et al. |
| 7,769,599 B2 | 8/2010 | Yanak et al. |
| 7,792,688 B2 | 9/2010 | Yanak et al. |
| 7,866,548 B2 | 1/2011 | Reed et al. |
| 7,996,260 B1 | 8/2011 | Cunningham et al. |
| 2001/0037295 A1 | 11/2001 | Olsen |
| 2001/0053986 A1 | 12/2001 | Dick |
| 2002/0002534 A1 | 1/2002 | Baudoin et al. |
| 2002/0002536 A1 | 1/2002 | Braco |
| 2002/0019808 A1 | 2/2002 | Sharma |
| 2002/0032583 A1 | 3/2002 | Joao |
| 2002/0073025 A1 | 6/2002 | Ludtke et al. |
| 2002/0128863 A1 | 9/2002 | Richmond |
| 2002/0138309 A1 | 9/2002 | Thomas |
| 2002/0147678 A1 | 10/2002 | Drunsic |
| 2002/0152180 A1 | 10/2002 | Turgeon |
| 2002/0160761 A1 | 10/2002 | Wolfe |
| 2002/0198831 A1 | 12/2002 | Byrd et al. |
| 2003/0004808 A1 | 1/2003 | Elhaoussine et al. |
| 2003/0040939 A1 | 2/2003 | Gardner et al. |
| 2003/0046154 A1 | 3/2003 | Larson et al. |
| 2003/0055686 A1 | 3/2003 | Fujiwara et al. |
| 2003/0193185 A1 | 10/2003 | Greeven et al. |
| 2003/0200118 A1 | 10/2003 | Barchet et al. |
| 2003/0212642 A1 | 11/2003 | Bray et al. |
| 2003/0225693 A1 | 12/2003 | Ballard et al. |
| 2004/0006490 A1 | 1/2004 | Beardsley et al. |
| 2004/0039693 A1 | 2/2004 | Abel et al. |
| 2004/0103000 A1 | 5/2004 | Comensky et al. |
| 2004/0111345 A1 | 6/2004 | Chuang et al. |
| 2004/0117250 A1 | 6/2004 | Bunin et al. |
| 2004/0128201 A1 | 7/2004 | Ofir et al. |
| 2004/0138999 A1 | 7/2004 | Blackley et al. |
| 2004/0148203 A1 | 7/2004 | Dunn et al. |
| 2004/0172312 A1 | 9/2004 | Druzolowski et al. |
| 2004/0186746 A1 | 9/2004 | Angst et al. |
| 2004/0203648 A1 | 10/2004 | Wong et al. |
| 2004/0210520 A1 | 10/2004 | Amalraj et al. |
| 2004/0225567 A1 | 11/2004 | Mastie et al. |
| 2004/0254816 A1 | 12/2004 | Myers |
| 2004/0260608 A1 | 12/2004 | Lewis et al. |
| 2005/0010448 A1 | 1/2005 | Mattera |
| 2005/0015280 A1 | 1/2005 | Gabel et al. |
| 2005/0033609 A1 | 2/2005 | Yang |
| 2005/0038675 A1 | 2/2005 | Siekman et al. |
| 2005/0065819 A1 | 3/2005 | Schultz |
| 2005/0065824 A1 | 3/2005 | Kohan |
| 2005/0071194 A1 | 3/2005 | Bormann et al. |
| 2005/0119918 A1 | 6/2005 | Berliner |
| 2005/0182721 A1 | 8/2005 | Weintraub |
| 2005/0187790 A1 | 8/2005 | Lapsker |
| 2005/0187794 A1 | 8/2005 | Kimak |
| 2005/0209893 A1 | 9/2005 | Nahra et al. |
| 2005/0211764 A1 | 9/2005 | Barcelou |
| 2005/0240478 A1 | 10/2005 | Lubow et al. |
| 2005/0246292 A1 | 11/2005 | Sarcanin |
| 2005/0273387 A1 | 12/2005 | Previdi |
| 2005/0288964 A1 | 12/2005 | Lutzen et al. |
| 2006/0010007 A1 | 1/2006 | Denman et al. |
| 2006/0106645 A1 | 5/2006 | Bergelson et al. |
| 2006/0106646 A1 | 5/2006 | Squilla et al. |
| 2006/0111943 A1 | 5/2006 | Wu |
| 2006/0129427 A1 | 6/2006 | Wennberg |
| 2006/0129435 A1 | 6/2006 | Smitherman et al. |
| 2006/0136270 A1 | 6/2006 | Morgan et al. |
| 2006/0149529 A1 | 7/2006 | Nguyen et al. |
| 2006/0149603 A1 | 7/2006 | Patterson et al. |
| 2006/0149670 A1 | 7/2006 | Nguyen et al. |
| 2006/0161456 A1 | 7/2006 | Baker et al. |
| 2006/0173712 A1 | 8/2006 | Joubert |
| 2006/0184455 A1 | 8/2006 | Meyer et al. |
| 2006/0206361 A1 | 9/2006 | Logan |
| 2006/0206376 A1 | 9/2006 | Gibbs et al. |
| 2006/0224417 A1 | 10/2006 | Werner |
| 2006/0229911 A1 | 10/2006 | Gropper et al. |
| 2006/0235761 A1 | 10/2006 | Johnson |
| 2006/0259364 A1 | 11/2006 | Strock et al. |
| 2007/0005403 A1 | 1/2007 | Kennedy et al. |
| 2007/0027715 A1 | 2/2007 | Gropper et al. |
| 2007/0038515 A1 | 2/2007 | Postrel |
| 2007/0061169 A1 | 3/2007 | Lorsch |
| 2007/0106607 A1 | 5/2007 | Seib et al. |
| 2007/0112629 A1 | 5/2007 | Solomon et al. |
| 2007/0125844 A1 | 6/2007 | Libin et al. |
| 2007/0143215 A1 | 6/2007 | Willems |
| 2007/0203792 A1 | 8/2007 | Rao |
| 2007/0288313 A1 | 12/2007 | Brodson et al. |
| 2008/0010096 A1 | 1/2008 | Patterson et al. |

(56) References Cited

U.S. PATENT DOCUMENTS

| | | | |
|---|---|---|---|
| 2008/0071646 | A1 | 3/2008 | Hodson et al. |
| 2008/0103817 | A1* | 5/2008 | Bohlke, III ..................... 705/2 |
| 2008/0147518 | A1 | 6/2008 | Haider et al. |
| 2008/0177574 | A1 | 7/2008 | Gonzalez et al. |
| 2008/0281733 | A1 | 11/2008 | Kubo et al. |
| 2008/0306761 | A1 | 12/2008 | George et al. |
| 2009/0006203 | A1 | 1/2009 | Fordyce, III et al. |
| 2009/0048871 | A1 | 2/2009 | Skomra |
| 2009/0079182 | A1 | 3/2009 | Dold et al. |
| 2009/0106115 | A1 | 4/2009 | James et al. |
| 2009/0125323 | A1* | 5/2009 | Lakshmanan et al. ............ 705/2 |
| 2009/0326977 | A1 | 12/2009 | Cullen et al. |
| 2010/0010901 | A1 | 1/2010 | Marshall et al. |
| 2010/0010909 | A1 | 1/2010 | Marshall et al. |
| 2010/0162171 | A1 | 6/2010 | Felt et al. |
| 2010/0312626 | A1 | 12/2010 | Cervenka |
| 2010/0312631 | A1 | 12/2010 | Cervenka |
| 2010/0312632 | A1 | 12/2010 | Cervenka |
| 2010/0312633 | A1 | 12/2010 | Cervenka |
| 2010/0312634 | A1 | 12/2010 | Cervenka |
| 2010/0312635 | A1 | 12/2010 | Cervenka |
| 2011/0047019 | A1 | 2/2011 | Cervenka et al. |

FOREIGN PATENT DOCUMENTS

| | | | |
|---|---|---|---|
| KR | 20030080111 A | 10/2003 | |
| KR | 10-2004-0028017 A | 4/2004 | |
| KR | 20040028110 A | 4/2004 | |
| KR | 10-2005-0099707 | 10/2005 | |
| KR | 10-2005-0094938 B1 | 6/2006 | |
| KR | 20060101241 A | 9/2006 | |
| KR | 10-2007-0041183 A | 4/2007 | |
| WO | 9922330 A1 | 5/1999 | |
| WO | 0106468 A1 | 1/2001 | |
| WO | 03073353 A2 | 9/2003 | |
| WO | 2006074285 A3 | 7/2006 | |
| WO | 2008102935 | 8/2008 | |

OTHER PUBLICATIONS

Hammond, W. Edward and James J. Camino, "Standards in Medical Informatics: Computer Applications in Health Care and Biomedicine," XP002564866, Springer, NY, 2000, 51 pages.

Administrative Services of Kansas, "ANSI Health Care Eligibility Benefit Inquiry and Response Companion Document," Last updated Aug. 5, 2010, 18 pages.

Classen, David et al., "The Patient Safety Institute Demonstration Project: A Model for Implementing a Local Health Information Infrastructure," Journal of Healthcare Information Management, vol. 19, 2004,12 pages.

First Consulting Group, "Patient Safety Institute Economic Value of a Community Clinical Information Sharing Network: Part 1, Value to Payers and the Uninsured" Mar. 2004, 18 pages.

Visa U.S.A. Inc., "Visa Introduces Next Generation B2B Payment Service," www.corporate.visa.com/md/nr/press136.jsp, Feb. 2, 2007, 3 pages.

Visa U.S.A. Inc., "Visa USA Small Business & Merchants, Visa ePay—How It Works," www.usa.visa.com/business/accepting_visa/payment_technologies/epay_how_it_works.html, Feb. 2, 2007, 1 page.

Visa U.S.A. Inc., "Visa USA Small Business & Merchants, Visa ePay—Participated Financial Institutes," www.usa.visa.com/business/accepting_visa/payment_technologies/epay_fi.html, Feb. 2, 2007, 1 page.

Visa U.S.A. Inc., "Visa ePay," www.usa.visa.com/business/accepting_visa/payment_technlogies/epay.html, Feb. 2, 2007, 1 page.

American Express, "American Express Healthypay Plus: What is Healthpay Plus," www.152.americanexpress.com/entcampweb/payment_technologies/epay_how_it_works, Feb. 2, 2007, 3 pages.

Visa U.S.A. Inc., "Visa USA Small Business & Merchants, Visa ePay—Credit Counseling Automation," www.usa.visa.com/business/accepting_visa/payment_technologies/epay_credit_counseling.html, Feb. 2, 2007, 3 pages.

"Visa Introduces Next Generation B2B Payment Service," www.sellitontheweb.con/ezine/news0569,html, Apr. 10, 2002, 4 pages.

American Express, "American Express Healthypay Plus: What is Healthpay Plus," www.152.americanexpress.com/entcampweb/whatishealthpayplus.jsp, Feb. 2, 2007, 3 pages.

European Patent Office, "Supplementary European Search Report," issued in connection with European Patent Application No. 06717481.3, mailed on Jan. 8, 2010, 9 pages.

International Searching Authority, "International Search Report," issued in connection with International Appl. No. PCT/US2006/00288, mailed on Aug. 31, 2007, 1 page.

European Patent Office, "Supplementary European Search Report," issued in connection with European Patent Application No. 06717470.6, mailed on Mar. 10, 2010, 8 pages.

International Searching Authority, "International Search Report," issued in connection with International Application U.S. Appl. No. PCT/US2006,00274, mailed on Aug. 29, 2007, 1 page.

International Searching Authority, "International Search Report," issued in connection with International Application Serial No. PCT/US2007/84179, mailed on May 5, 2008, 4 pages.

International Searching Authority, "International Search Report," issued in connection with International Application No. PCT/US2009/066847, mailed Jun. 28, 2010, 3 pages.

International Searching Authority, "International Search Report and Written Opinion," issued in connection with International Application No. PCT/US2009/049203, mailed on Feb. 9, 2010, 8 pages.

EIC 3600 to John Holly, "Search Report," performed in connection to U.S. Appl. No. 11/230,7691, mailed on Aug. 20, 2009, 74 pages.

European Patent Office, "Supplementary European Search Report," issued in connection with European Patent Application No. 06717482.1, mailed on Jan. 8, 2010, 4 pages.

International Searching Authority, "International Search Report," issued in connection with International Application No. PCT/US2010/051355, mailed Apr. 29, 2011, 4 pages.

International Searching Authority, "International Search Report," issued in connection with International Application No. PCT/US2010/045500, mailed on Mar. 29, 2011, 3 pages.

International Searching Authority, "International Search Report," issued in connection with International Application No. PCT/US2010/045445, mailed on Feb. 24, 2011, 3 pages.

International Searching Authority, "International Search Report and Written Opinion," issued in connection with International Application No. PCT/US2007/70780, mailed on May 30, 2008, 8 pages.

European Patent Office, "Supplementary European Search Report," issued in connection with European Patent Application No. 07798894.7, mailed on May 25, 2011, 3 pages.

International Searching Authority, "International Search Report and Written Opinion," issued in connection with International Application Serial No. PCT/US2007/71797, mailed on Dec. 20, 2007, 10 pages.

European Patent Office, "Supplementary European Search Report," issued in connection with European Patent Application No. 08771445.7, mailed on Aug. 6, 2010, 5 pages.

International Searching Authority, "International Search Report and Written Opinion," issued in connection with International Application No. PCT/US2008,67460, mailed Aug. 29, 2008, 8 pages.

International Searching Authority, "International Search Report," issued in connection with International Application No. PCT/US2007/74862, mailed Sep. 29, 2008, 3 pages.

Canadian Corporate News, "Racal Introduces WebSentry Reducing the Risk of Fraud for Internet Transactions; WebSentry Offers System Integrators Cost Effective SET Compliance for E-Commerce," May 26, 1999, 2 pages.

* cited by examiner

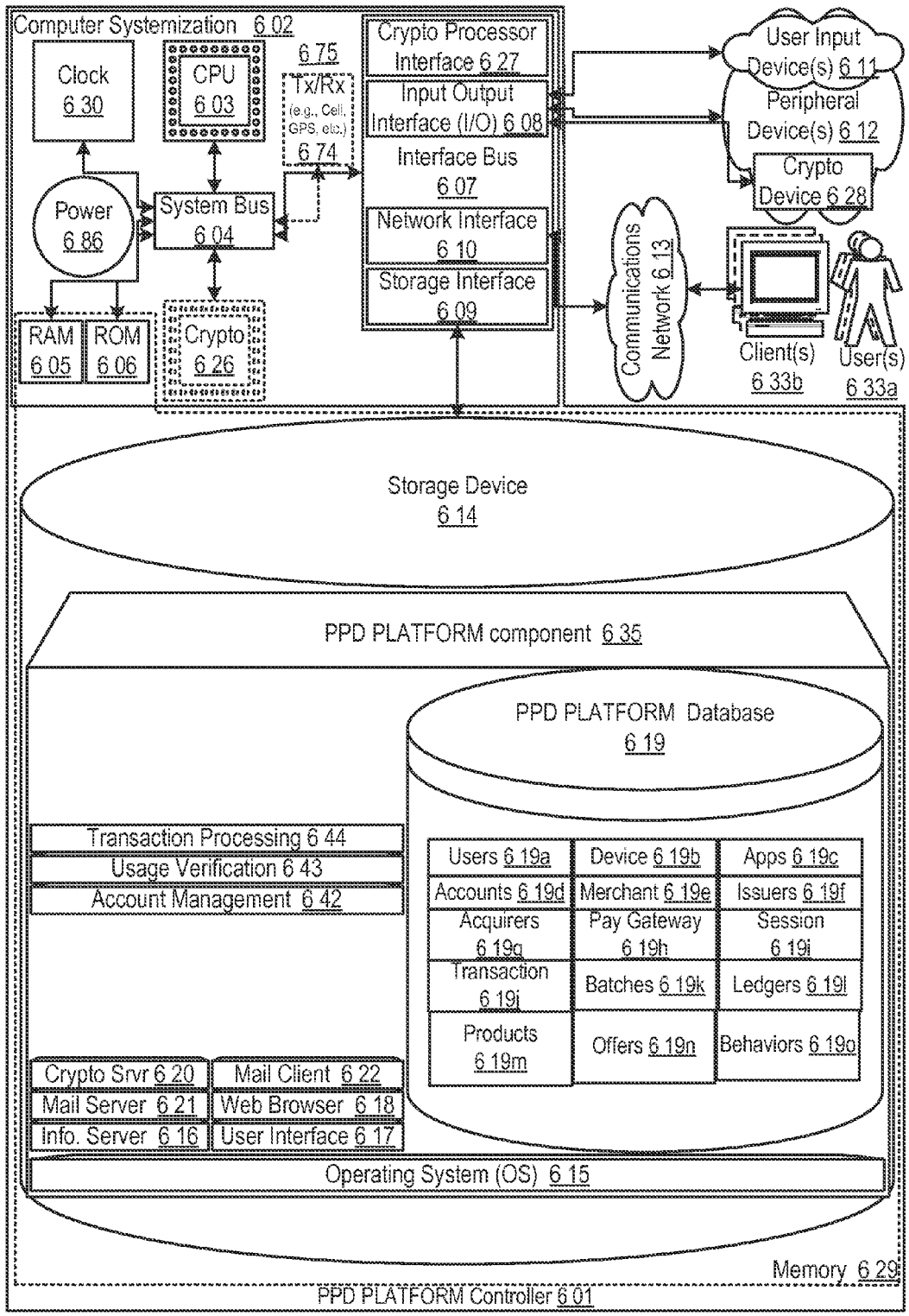

US 8,939,356 B2

PORTABLE PRESCRIPTION PAYMENT DEVICE MANAGEMENT PLATFORM APPARAUTSES, METHODS AND SYSTEMS

PRIORITY CLAIM

This application is a continuation-in-part of, and claims priority under 35 U.S.C. §§120, 365 to: co-pending U.S. nonprovisional patent application Ser. No. 12/573,688, filed Oct. 5, 2009, titled "Portable Prescription Transaction Payment Device," and co-pending U.S. nonprovisional patent application Ser. No. 12/545,372, filed Aug. 21, 2009, entitled "Free Sample Coupon Card."

Application Ser. No. 12/545,372 is a continuation in part of each of the following utility applications: (i) U.S. patent application Ser. No. 12/480,268, filed on Jun. 8, 2009, by Karen Cervenka, titled Coupon Card Generation Web Service; (ii) U.S. patent application Ser. No. 12/480,346, filed on Jun. 8, 2009, by Karen Cervenka, titled Dual Range Cellular Telephone Coupon Card Generation; (iii) U.S. patent application Ser. No. 12/480,444, filed on Jun. 8, 2009, by Karen Cervenka, titled Coupon Card Kiosk; (iv) U.S. patent application Ser. No. 12/480,529, filed on Jun. 8, 2009, by Karen Cervenka, titled Coupon Card Point Of Service Terminal Processing; and (v) U.S. patent application Ser. No. 12/480,551, filed on Jun. 8, 2009, by Karen Cervenka, titled Transaction Handler Merchant Reimbursement For Consumer Transaction Use Of Sponsor Discount Coupon Card. Each of the foregoing utility applications is incorporated herein by reference.

The entire contents of the aforementioned applications are all expressly incorporated by reference herein.

OTHER APPLICATIONS

The following applications are all expressly incorporated by reference herein: U.S. patent application Ser. No. 12/573,817, titled "Portable Consumer Transaction Payment Device Bearing Sponsored Free Sample"; U.S. patent application Ser. No. 12/573,833, titled "Portable Consumer Transaction Payment Device Bearing Sample Prescription"; U.S. patent application Ser. No. 12/573,838, titled "Free Sample Account Transaction Payment Card Dispensing Kiosk"; U.S. patent application Ser. No. 12/573,846, titled "Prescription Sample Transaction Payment Card," all of the four filed on Oct. 5, 2009; and PCT international application serial no. PCT/US2010/051355, titled Sample Bearing Portable Transaction Payment Device, filed Oct. 4, 2010.

This patent for letters patent disclosure document describes inventive aspects that include various novel innovations (hereinafter "disclosure") and contains material that is subject to copyright, mask work, and/or other intellectual property protection. The respective owners of such intellectual property have no objection to the facsimile reproduction of the disclosure by anyone as it appears in published Patent Office file/records, but otherwise reserve all rights.

FIELD

The present innovations generally address apparatuses, methods, and systems for restricted product supply management, and more particularly, include PORTABLE PRESCRIPTION PAYMENT DEVICE MANAGEMENT PLATFORM APPARATUSES, METHODS AND SYSTEMS ("PPD").

BACKGROUND

Consumer transactions require a customer to select a product from a store shelf or website, and then to check the out at a checkout counter or webpage. Product information is selected from a webpage catalog or entered into a point-of-sale terminal, or the information is entered automatically by scanning an item barcode with an integrated barcode scanner at the point-of-sale terminal. The customer is usually provided with a number of payment options, such as cash, check, credit card or debit card. Once payment is made and approved, the point-of-sale terminal memorializes the transaction in the merchant's computer system, and a receipt is generated indicating the satisfactory consummation of the transaction.

BRIEF DESCRIPTION OF THE DRAWINGS

The accompanying appendices and/or drawings illustrate various non-limiting, example, inventive aspects in accordance with the present disclosure:

FIG. 6 shows a block diagram illustrating embodiments of a PPD controller within embodiments of PPD.

Figure 1A:
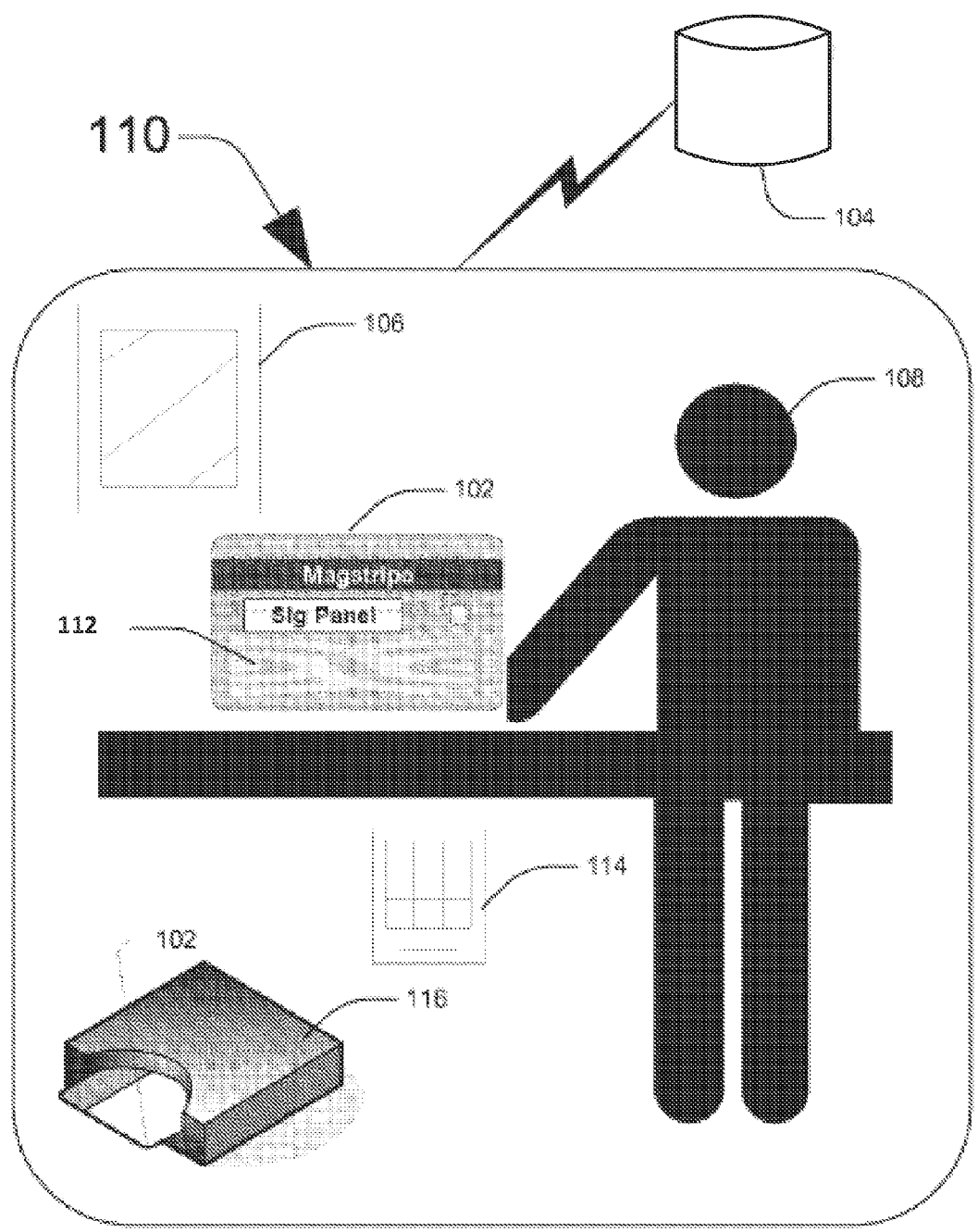
FIGS. 1A-1B depict block diagrams of an exemplary method of a healthcare provider using a card processor system to associate a sample transaction payment card with an electronic voucher within embodiments of PPD.

The leading number of each reference number within the drawings indicates the figure in which that reference number is introduced and/or detailed. As such, a detailed discussion of reference number 101 would be found and/or introduced in FIG. 1. Reference number 201 is introduced in FIG. 2, etc.

DETAILED DESCRIPTION

Portable Prescription Payment Device Management Platform (PPD)

PORTABLE PRESCRIPTION PAYMENT DEVICE MANAGEMENT PLATFORM (PPD) provides a platform for the distribution of samples, and more particularly with the distribution of pharmaceutical samples, and most particularly to a sample transaction payment card that can be exchanged by a patient at a pharmacy dispensing the sample of the prescribed medical supply to the patient, the sample transaction payment card being associated with an account of a third party who is financially response for the cost of the prescribed medical supply sample.

For example, when a patient sees a healthcare provider for an ailment, often the patient is provided samples of pharmaceutical products to try. This may be done when the healthcare provider is unsure which medication will alleviate the patient's symptoms or illness, or when a prescription is very expensive. However, this form of distribution can be dangerous. The healthcare provider may accidentally provide the wrong sample to the patient, might not keep accurate records of what samples were given, or may not be aware of possible interactions with medications the patient has been prescribed by other providers.

Additionally, the distribution of sample pharmaceutical products by healthcare providers is costly. Pharmaceutical companies must send the sample drugs to representatives, who are then paid to distribute the samples to local healthcare providers. These samples must be individually packaged, often with expensive safety features and elaborate advertisements. Further, the pharmaceutical companies must cover the cost of the samples themselves regardless of whether the healthcare provider ever actually distributes the samples. All of this adds to the soaring prices of medications.

Thus, there is a need for a system that allows healthcare providers to provide patients with access to sample medications within a more controlled environment, such as a pharmacy. Further, there is a need to reduce medication and medical supply costs by removing the expense of representatives and individual sample packaging.

In one implementation, a portable prescription sample transaction payment device is provided with memory, embedded in a substrate, and having information stored in the memory. The substrate can have a surface with an image of a representation of the information in the memory. The image can be read by being scanned by a scanner at a Point of Service terminal. The information includes an identifier, quantity, and dosage for each of a plurality of prescription medical supply samples prescribed by a prescribing medical practitioner to a patient. The information can also include one or more non-sample prescription medical supplies prescribed by a corresponding prescribing medical practitioner to the patient. The information in the memory can also include an image of each prescription for the patient that was prescribed by the corresponding prescribing medical practitioner. For each prescription medical supply sample, a pharmaceutical company account is included in the information in the memory. The pharmaceutical company account can be used for a dispensing pharmacist to charge the cost of the prescription medical supply sample for payment to a dispensing pharmacist account to reimburse the dispensing pharmacist for the prescription medical supply sample. Also included in the information in the memory is an identifier to correlate which prescription for the patient was prescribed by which prescribing medical practitioner. A device or mechanism is provided by which the information in the memory can be accessed.

In one implementation, a method includes receiving, in a transmission from a network, information about a free sample in response to a request. The information includes an advertising account for a merchant to charge the cost of the free sample to and an identifier and quantity of the free sample. The information is written to the memory of a portable consumer transaction payment device where, also encoded in the memory, is a consumer account for the consumer to engage in transactions on the account with merchants in a payment processing network. A transaction for the free sample is submitted by the merchant to the merchant's acquirer for processing by a transaction handler who requests payment for the transaction from the advertising account, and the issuer of the advertising account forwards the payment for the free sample to the acquirer to reimburse the merchant. Other transactions, which are not for the free sample, are submitted by each merchant to an acquirer for processing by a transaction handler who requests payment for the transaction from the account borne on the portable consumer transaction payment device, and the issuer of the account forwards the payment to the acquirer to reimburse the merchant.

In another implementation, a method includes browsing to an Internet website in communication with a web service having a database of information that includes free samples and sending a request to the web service including a selection of one free sample. Information about the free sample is then received in a transmission from the website. The information includes an advertising account for a merchant to charge the cost of the free sample for payment to the merchants' account to reimburse the merchant for the free sample, a graphic image for rendering at a Point Of Service terminal (POS), and an identifier and quantity of the free sample. The received information is written to the memory of a portable consumer transaction payment device where, also encoded in the memory, is a consumer account for the consumer to engage in transactions on the account with merchants in a payment processing network. In a transaction between the consumer and a merchant for the free sample, data from the transaction is submitted by the merchant to the merchant's acquirer for processing by a transaction handler who requests payment for the transaction from the advertising account, and the issuer of the advertising account forwards the payment for the free sample to the merchant's acquirer to reimburse the merchant for giving the free sample to the consumer. Other transactions, which are not for the free sample, are submitted by each merchant to an acquirer for processing by a transaction handler who requests payment for the transaction from the account borne on the portable consumer transaction payment device, and the issuer of the account forwards the payment to the acquirer to reimburse the merchant.

In yet another implementation, an apparatus is presented. The apparatus includes a user interface to receive a request for a free sample and a network communication device to send the request for the free sample and receive an advertising account for a merchant to charge the cost of the free sample to in order to reimburse the merchant for the free sample. The apparatus further includes a card writer to encode data in the memory of the portable consumer transaction payment device where the data includes the advertising account, an identifier and quantity of the free sample, and a graphic image for rendering at a Point of Sale terminal (POS) of the merchant. Already encoded in the memory of the portable consumer transaction payment device is a consumer account for the consumer to engage in transactions on the account with merchants in a payment processing network. In a transaction between the consumer and a merchant for the free sample, data from the transaction is submitted by the merchant to the merchant's acquirer for processing by a transaction handler who requests payment for the transaction from the advertising account, and the issuer of the advertising account forwards the payment for the free sample to the merchant's acquirer to reimburse the merchant for giving the free sample to the consumer. Other transactions, which are not for the free sample, are submitted by each merchant to an acquirer for processing by a transaction handler who requests payment for the transaction from the account borne on the portable consumer transaction payment device, and the issuer of the account forwards the payment to the acquirer to reimburse the merchant.

In one implementation, a method includes receiving, in response to a request sent over a network, information about a prescription medical supply sample that includes an advertising account to which a dispensing pharmacist is to charge the cost of the prescription medical supply sample, and an identifier, quantity, and dosage of the prescription medical supply sample. The received information is then written to the memory of a portable consumer transaction payment device along with an identifier for the patient and identifier for the prescribing medical practitioner. The portable consumer transaction payment device is associated with a patient account to engage in transactions on the patient account with merchants in a payment processing network.

In another implementation, a method includes receiving a transmission from a network in response to a request, where the transmission has information about a prescription medical supply sample that includes an advertising account for the dispensing pharmacist to charge the cost of the prescription medical supply sample to and an identifier, quantity and dosage of the prescription medical supply sample. The method further includes writing to the memory of a portable consumer health services payment device the information received, an identifier for the patient, an identifier for a medical practitioner prescribing the prescription medical supply sample to the patient, and an identifier, quantity, and dosage of a prescription medical supply, other than the prescription medical supply sample, being prescribed by the prescribing medical practitioner to the patient. The patient account is regulated for limited use for payments to healthcare providers and is for the dispensing pharmacists to charge the cost of the prescription medical supply.

In yet another implementation, an apparatus is presented having a user interface to receive a request for a prescription medical supply sample, a network communication device, and a card writer to encode the prescription data in the memory of a portable consumer transaction payment device. The network communication device further is capable of sending the request for a prescription medical supply sample and receiving an advertising account for a dispensing pharmacist to charge the cost of the prescription medical supply sample to. The prescription data includes the advertising account, and identifier for a patient, and an identifier for a prescribing medical practitioner. The prescription data further includes an identifier, a quantity, and a dosage of the prescription medical supply sample and a prescription medical supply, other than the prescription medical supply sample, which the prescribing medical practitioner is prescribing to the patient. The prescription data also includes an image of a prescription for the patient from the prescribing medical practitioner. Included in the memory of the portable consumer transaction payment device is a consumer account for a consumer to engage in transactions on the consumer account with merchants in a payment processing network, where the dispensing pharmacist is one such merchant in the payment processing network and the charging of the cost of the prescription medical supply sample to the advertising account for the payment to the dispensing pharmacist account is another said transaction in the payment processing network. Each transaction in the payment processing network is submitted by the merchant to an acquirer for processing by a transaction handler who requests an issuer of a corresponding account upon which the transaction was conducted to obtain payment for the transaction from the corresponding account, and wherein the issuer of the corresponding account forwards the payment for the transaction to the transaction handler who forwards the payment for the transaction to the acquirer to reimburse the merchant for the transaction.

In one implementation, a method of providing a free sample account transaction payment card to a user of a kiosk is provided. The method includes receiving a selection of a free sample from a database having multiple selectable free samples. Each free sample is associated with a free sample account issued to a sponsor who is financially responsible for the cost of providing the free sample to a customer, where the free sample account is acceptable by a merchant for payment for a free sample given to a customer and the cost of the free sample is debited from the free sample account and credited to the merchant's account. The method further includes retrieving, from the database, to memory in the kiosk, a rendering image corresponding to the rendering capability of the kiosk and the free sample information. The free sample information includes the free sample account, a quantifier for the free sample, and a good or service. The free sample information is then written from the memory in the kiosk to a memory location in a free sample account transaction payment card stored within the kiosk and a hard copy of the rendering image is rendered on a surface of the free sample account transaction payment card.

In another implementation, a kiosk is presented. The kiosk includes a means for displaying selectable free samples, each of which are associated with a free sample account issued by an issuer to a sponsor who is financially responsible for the cost of providing the free sample to the consumer. The free sample account is acceptable by a merchant for payment of a free sample tendered to a consumer and the cost of distributing the free sample is debited from the free sample account and credited to the merchant's account. The kiosk also includes a means for receiving a selection of free samples from the selectable free samples and a means for retrieving from the database to the memory of the kiosk a rendering image corresponding to the rendering capabilities of the kiosk and the free sample information, including the free sample account, a quantifier for the free sample, and a good or service. The kiosk further includes a means for writing, using a card writing device, the free sample information from the memory of the kiosk to the memory of a free sample account transaction payment card and a means for rendering a hard copy of the rendering image on a surface of the free sample account transaction payment card.

In yet another implementation, a kiosk is presented. The kiosk has a user interface having a display device and an input device, memory, and a computing apparatus that executes an internet browser to access a web site associated with a server serving a web page for displaying multiple free samples. Each free sample is associated with a free sample account issued by an issuer to a sponsor who is financially responsible for the cost of providing the free sample to a consumer, where the free sample account is acceptable by a merchant for payment in a transaction in which the merchant tenders the free sample to the consumer, the cost of the free sample is to be debited from the free sample account and credited to a merchant account to reimburse the merchant for tendering the free sample. The computing apparatus further executes the internet browser to transmit to the server a selection of a free sample and to receive a rendering image and the free sample information, including an identifier for the free sample account, a quantifier for the free sample, and a good or service. The kiosk further includes a card writing device to write the sample information to memory in a free sample account transaction payment card and render a hard copy of the rendering image on the surface of the free sample account transaction payment card.

In another implementation, a method includes receiving, using an input device of a user interface, an identifier, quantity, and dosage of a free prescription medical supply sample and an identifier for a patient. A transmission is sent including the identifier for the free prescription medical supply sample and, in response, a transmission is received including the free prescription medical supply sample information. The information includes a pharmaceutical company account to which for the dispensing pharmacist is to charge the cost of the free sample, the identifier, quantity, and dosage of the free sample, and an image corresponding to the free prescription medical supply sample. The method further includes receiving a prescription medical supply sample transaction payment card and writing to its memory the free prescription medical supply sample information, an identifier for the patient, and an identifier for the prescribing medical practitioner. The image corresponding to the free prescription medical supply sample is rendered on the surface of the prescription medical supply sample transaction payment card.

In another implementation, a method includes browsing, using an input device of a user interface, to an Internet website in communication with a web service having a database of information that includes different free pharmaceutical samples and receiving an identifier, quantity and dosage of a selected free prescription medical supply sample, and a prescription for a prescription medical supply sample prescribed by a medical practitioner to a patent. A transmission is then sent to the web service which includes an identifier for the selected free prescription medical supply sample. In response, a transmission is received which includes free prescription medical supply sample information including a pharmaceutical company account for the dispensing pharmacist to charge the cost of the free prescription medical supply sample and an image corresponding to the selected free prescription medical supply sample. A free prescription medical supply sample is then received and written to its memory is the free prescription medical supply sample information, an identifier for the patient, an identifier for the prescribing medical practitioner, and an image of the prescription. The image corresponding to the prescription medical supply sample is then rendered on the surface of the prescription medical supply sample transaction payment card. Additionally, the pharmaceutical company account is a type of consumer account issued by an issuer to a pharmaceutical company, the prescription medical supply sample transaction payment card is a type of portable consumer device that is associated with a consumer account, the payment processing network includes multiple merchants and consumers conducting transactions, and each transaction involves the merchant submitting the transaction to an acquirer for processing by a transaction handler.

In yet another implementation, an apparatus is presented comprising a means for receiving an identifier, quantity, and dosage of a free prescription medical supply sample, an identifier for a prescribing medical practitioner, and an identifier for a patient. The apparatus further comprises a first communication means for sending a transmission out to a network including the identifier for the free prescription medical supply sample and a second communication means for receiving a transmission in response which includes free prescription medical supply sample information. The information includes a pharmaceutical company account for a dispensing pharmacist to charge the cost of the free prescription medical supply sample to, and an image corresponding to the free prescription medical supply sample. The apparatus further comprises a means for writing to the memory of a prescription medical supply sample transaction payment card the identifier, quantity, and dosage of the free prescription medical supply sample, the identifier for a prescribing medical practitioner, an identifier for the patient, and the pharmaceutical company account. Finally, the apparatus comprises a means for printing the image corresponding to the free prescription medical supply sample on the surface of the prescription medical supply sample transaction payment card.

The present discussion considers a sample of a prescription medical supply that can be prescribed to a patient by a healthcare provider's use of a portable prescription transaction payment device, such as may have the form factor of a transaction payment card. Such a sample transaction payment card can be exchanged by the patient with a pharmacist who will dispense the sample of the prescription medical supply to the patient. In the present context, an account for the payment of a sample attributable to an electronic voucher is issued by an issuer to a third-party sponsor of the electronic voucher and credited with funds submitted by the third-party. The funds on deposit in the account are for reimbursement of the distribution of the sample by the dispensing pharmacist upon the presentation by the patient of the sample transaction payment card having the electronic voucher stored thereon. The sample transaction payment card is provided to the patient by a prescribing healthcare provider and has information stored therein for at least one electronic voucher. In another implementation, the PPD may apply the portable consumer transaction payment device to the consumer as; (i) a free sample card for the consumer to use to obtain a free sample from a merchant without paying for the free sample; and (ii) a typical card (i.e., credit card, debit card, or prepaid card, etc.) to use for other commercial transactions for which the consumer must pay the merchant from funds associated with an account issued to the consumer that corresponds to the card. Accordingly, the portable consumer transaction payment device will also be referred to herein as a 'free sample card'.

In certain implementations, the sponsor of the electronic voucher is the manufacturer of the sample. In certain implementations, the merchant who provides data as input into the memory or storage of the sample card is a distributor of the sample. In certain implementations, the merchant provider is a wholesaler of the sample. In certain implementations, the merchant provider and the third-party sponsor are the same entity. In certain implementations, the merchant provider is a retailer of different goods or services than the retail merchant.

In another implementation, The present discussion considers a coupon card and its use in a payment processing system that processes electronic coupons stored on the coupon card. In the present context, an account for the payment of future discounts on goods and services attributable to the use of electronic coupons is issued by the issuer to a third-party and credited with funds submitted by the third-party. The funds are for reimbursement of discounts on the sale of goods and services given by a merchant upon the presentation of a coupon card having at least one of the electronic coupons stored thereon.

In one implementation, a portable coupon payment device is presented. The portable coupon payment device includes a substrate having surface with an image rendering thereon that corresponds to a free sample. The portable coupon payment device also has memory, in contact with the substrate, having data encoded therein including (i) an identifier for the free sample, (ii) a quantity for the free sample; (iii) a sponsor company account for a selling merchant to charge the cost of the free sample for payment to a selling merchant account to reimburse the selling merchant for the free sample; (iv) an image corresponding to the free sample; and (v) an identifier for a coupon provider donating the free sample to a consumer.

In another implementation, a portable coupon transaction payment device is presented. The portable coupon transaction payment device has memory embedded in a substrate. Stored in the memory are an identifier and a quantity for each of a plurality of a free sample donated by a coupon provider to a consumer and a non-sample item each being offered by a corresponding coupon provider to the consumer. Also stored, for each free sample, is a sponsor company account for a selling merchant to charge the cost of the free sample for payment to a selling merchant account to reimburse the selling merchant for the free sample. Also stored is an identifier for the consumer. Also stored, is an identifier for each coupon provider. Also stored is an identifier for a consumer account issued by an issuer to the consumer. Also stored is an identifier to correlate which donation for the consumer was donated by which coupon provider. The sponsor company account and the consumer account are each an account in a payment processing network by which a consumer can engage in a plurality of transactions on the account with a plurality of merchants in the payment processing network. The payment processing network includes a plurality of merchants and consumers engaging in the plurality of transactions on a plurality of respective accounts that respective issuers issue to the consumers. Each transaction involves the merchant submitting the transaction to an acquirer for processing by a transaction handler who requests the issuer to obtain payment for the transaction from the account, wherein the issuer forwards the payment to the transaction handler who forwards the payment to the acquirer to reimburse the merchant for the transaction. The portable coupon transaction payment device also includes means for providing access to the information in the memory.

In yet another implementation, a portable coupon transaction payment device is presented. The portable coupon transaction payment device has memory embedded in a substrate. The memory has information stored therein. The substrate has an image on a surface thereof that includes a representation of at least a portion of the information in the memory for being read by the image being scanned by a scanner at a Point of Service terminal. The stored information includes (i) an identifier and a quantity for each of a plurality of a free sample donated by a coupon provider to a consumer and a non-sample item offered by a corresponding coupon provider to the consumer; (ii) an image, having multiple portion, of each donation for the consumer that was donated by the corresponding coupon provider, wherein the portions of the image correspond to the identifier for the consumer, the identifier for the coupon provider; the identifier and the quantity for the free sample; and the identifier and the quantity for the non-sample item; (iii) for each free sample, a sponsor company account for a selling merchant to charge the cost of the free sample for payment to a selling merchant account to reimburse the selling merchant for the free sample; and (iv) an identifier to correlate which donation for the consumer was donated by which coupon provider. The sponsor company account and the consumer account are each an account in a payment processing network by which a consumer can engage in a plurality of transactions on the account with a plurality of merchants in the payment processing network. The payment processing network includes a plurality of merchants and consumers engaging in the plurality of transactions on a plurality of respective accounts that respective issuers issue to the consumers. Each transaction involves the merchant submitting the transaction to an acquirer for processing by a transaction handler who requests the issuer to obtain payment for the transaction from the account, wherein the issuer forwards the payment to the transaction handler who forwards the payment to the acquirer to reimburse the merchant for the transaction. The portable coupon transaction payment device also has means for providing access to the information in the memory.

In alternatives to the foregoing implementations, the memory can be a non-volatile memory of a semiconductor device, a magnetic encoded data region of a magnetic stripe, or a combination of the foregoing. The substrate can be a portion of a consumer transaction payment card (e.g. a smart card having a Radio Frequency Identification (RFID) tag, a transponder device and a microchip, a magstripe card, or a combination of the foregoing. The portable coupon transaction payment device can include circuitry and corresponding firmware, as would be understood by those of skill in the relevant arts, for the memory to receive the information by a wireless communication, a hardwired communication, or a magnetic encoded communication for track data received by modifying the magnetism of magnetic particles on a band of magnetic material on the portable coupon payment device. For each image of each donation, the identifier for the coupon provider can be a handwritten signature of the coupon provider. Alternatively, for each image of each free sample, the free sample in the image can be hand written by the coupon provider.

In certain implementations, the third-party sponsor, merchant provider, and/or retail merchant are related companies. In such implementations, the retail merchant and or merchant provider may be subsidiaries of the third-party sponsor. In certain implementations, the third-party sponsor of the electronic voucher is the manufacturer of the sample. In certain implementations, the third-party sponsor is the distributor of the sample. In certain implementations, the third-party sponsor is the wholesaler of the sample. Throughout the specification, the entity "healthcare provider" may be a merchant provider, retail merchant, and/or the like.

Turning now to FIG. 1A, an exemplary block diagram is presented of an environment 110 of a healthcare provider using a card processor system to associate a sample transaction payment card with an electronic voucher, where the sample transaction payment card may be used by the patient for a sample medical supply prescribed by the healthcare provider to be dispensed to the patient by a pharmacist. Although the implementation is discussed in regards to a substantially planar laminated card, one skilled in the art will recognize that other forms of transaction payment tokens could be used.

Although the present application is primarily concerned with prescription medication, one of ordinary skill in the art will understand that the samples may be of prescription medical supplies, such as by way of example and not limitation, syringes or home medical supplies covered by health insurance. Furthermore, the samples may be of over-the-counter (OTC) medications or medical supplies, such as by way of example and not limitation, aspirin, antiseptics, bandages, creams, or salves.

Further, one of ordinary skill in the art will realize that, in the present discussion, "healthcare provider" is intended to include doctors, nurse practitioners, veterinarians, dentists, psychiatrists, veterinarians, and any other prescriber. Additionally, wherein the sample is for an OTC medication or medical supply, "healthcare provider" may include chiropractors, homeopathic therapists, acupuncturists, physical therapists, or any other provider of health-related services. Also, it will be understood that a patient of a healthcare provider could act through an agent to perform acts described herein.

In another implementation, sample card 102, being a portable consumer transaction payment device, may be a credit card, debit card, prepaid card, loyalty card, or other such device associated with an account that was issued by an issuer to a consumer. Thus, the consumer may use sample card 102 to both receive a sample and to pay for an item or service. In certain implementations, the account of the consumer associated with sample card 102 is a regulated account that's use is limited to payments to certain kinds of merchants dealing in certain limited commodities, where such merchants may be represented by one or more Merchant Commodity Codes (i.e., petroleum products and services, travel and entertainment, healthcare, etc.) In certain implementations, the consumer account is a revolving credit account, a debit account, or a prepaid account. In certain implementations, the consumer account is a Flexible Savings Account (FSA), a Health Savings Account (HSA), or a Health Reimbursement Account (HRA).

In certain implementations, a card processor system is connected to a database 104. The card processor system, for instance, can create, from a blank transaction payment card, a prescription medical supply sample transaction payment card that is encoded with information to facilitate a transaction with a dispensing pharmacist for a patient to receive the sample at substantially no cost. In certain implementations, database 104 is a database of electronic vouchers for free samples which healthcare provider 108 may distribute to patents. In one implementation, a third-party offering, and willing to pay for, the distribution of at least one sample using an electronic voucher has access to the database and may send to and receive from the database information such as the number of electronic vouchers used, the number of electronic vouchers remaining, alternatives to a given sample, medications commonly prescribed with a given sample and the availability of such medications, or any other relevant information.

In certain implementations, database 104 is connected to a network accessible by a computer used by healthcare provider 108. In such implementations, the network may be a Local Area Network (LAN), Wide Area Network (WAN), Personal Area Network (PAN), Virtual Private Network (VPN), Storage Area Network (WAN), Global Area Network (GAN), Internetwork, or combination thereof. In such implementations, the computer may connect to the network using wireless communications, optical fiber, Ethernet, ITU-T G.hn, or similar technology, or a combination thereof. In such implementations, the computer may include a network card, network adapter, or network interface controller (NIC). In other implementations, the computer may include other types of hardware capable of connecting to and communicating with a network.

In certain implementations, database 104 is provided by a web service in communication with a website. In such implementations, healthcare provider 108 browses, using a web browser of a web-enabled computer, to the website to select an electronic voucher from database 104.

In certain implementations, database 104 also includes information relating to each electronic voucher stored therein. In such implementations, database 104 may include an identifier for the free sample and an account identifier of the third-party sponsor of the electronic voucher. In certain implementations, the account of the third-party sponsor is a regulated account that's use is limited to payments to healthcare providers. In certain implementations, the third-party account is a revolving credit account, a debit account, or a prepaid account. In certain implementations, the third-party account is a Flexible Savings Account (FSA), a Health Savings Account (HAS), or a Health Reimbursement Account (HRA).

In certain implementations, database 104 includes information also regarding a merchant. In such an implementation, the electronic voucher may only be valid for use with a particular compounding pharmacy or drug store. In other implementations, the information includes the prescription date or an expiration date, after which the electronic voucher is no longer valid. In yet other implementations, the information includes the number of samples eligible for distribution using the electronic voucher. By way of example and not limitation, the electronic voucher may be valid for three (3) sample-sized tubes of a prescription topical cream. In other implementations, the database 104 includes information regarding an expiration date, after which the electronic voucher is no longer valid.

By way of another example and not limitation, the electronic voucher may be valid for three (3) sample-sized cans for house paint, or a free decal for an automobile body part, or a free massage at a spa, or a free tennis lesson, or a free appraisal of a jewelry or work of art, or for both a free car wash and a free air freshener. In certain implementations, database 104 includes information regarding a retail merchant where the electronic voucher is valid only for use with that particular retail merchant.

In certain implementations, database 104 includes advertisements and/or educational or safety information capable of being printed by a merchant Point Of Service terminal (POS), (i.e., a cash register) when the sample transaction payment card bearing the electronic voucher is presented to a pharmacist. In other implementations, the advertisements may be capable of being rendered as printed out on a hard copy or rendered on a monitor at a merchant. In certain implementations, a specific advertisement is selected by healthcare provider 108 to be associated with the sample transaction payment card. In certain implementations, the advertisements are pre-associated with the electronic vouchers. In certain implementations, the advertisement may be an image. In certain implementations, the advertisement may be for a type of good or service, which may or may not be related to the free prescription sample. In certain implementations, the advertisement may be for the pharmacist providing the free sample or for the third-party sponsor. In certain implementations, the advertisement is of a different good or service provided by healthcare provider 108, the pharmacist, or by the third-party sponsor. In certain implementations, the advertisement is for a merchant, or a good or service provided by a merchant, whose retail location is near healthcare provider 108 or the pharmacist.

In some implementations, database 104 includes information regarding a coupon for a free or discounted item. The coupon may be issued by the sponsor of the electronic voucher. In other implementations, healthcare provider 108 may select a coupon from multiple coupons available in database 104. In yet other implementations, database 104 may automatically associate a coupon with sample transaction payment card 102. The association may be based upon the medications being prescribed, the diagnosis of the patient, or any other criteria. The coupon may be for discounts on prescription medication or over-the-counter items, such as, for example, cough syrups, bandages, or herbal teas. In one implementation the coupon expires with the use of the consumer payment device to obtain the sample associated with the electronic voucher, the discount only being redeemable at the time medication is dispensed. In other implementations, the coupon may be redeemable at a later time.

In certain implementations, the identifier of the free sample corresponds to a type of good or service. In certain implementations, the identifier is an image capable of being displayed or printed by a merchant POS. In certain implementations, the identifier of the free sample is a Stock Keeping Unit (SKU). In certain implementations, the identifier of the free sample is a Universal Product Code (UPC). In certain implementations, the identifier is of a trademark associated with the product being distributed as a sample, the trade name of the wholesaler of the product, or the trade name of the manufacturer of the product. In certain implementations, the identifier is for an active ingredient of the product being distributed as a free sample. In certain implementations, the identifier is a National Drug Code (NDC).

The card processor system, in some implementations, may include a user interface 106 capable of presenting healthcare provider 108 with a selection of electronic vouchers available for distribution. The user interface 106 may be a touch screen, a digital electronic display with an input device, a projector with an input device, a monitor with an input device, any combination of the foregoing, or any other device for the presentation of information.

Healthcare provider 108 may select an electronic voucher using input device 114. Input device 114 may be a key pad, a touch screen, a pointing device, an audio input device, a video input device, any combination of the foregoing, or other hardware capable of receiving and transforming data for use by the device.

Card read-write device 116 may then be used to associate the selected electronic vouchers with sample transaction payment card 102. In certain implementations, prior to association, sample transaction payment card 102 is a blank card. In certain implementations, sample transaction payment card 102 is provided by the third-party sponsor of the electronic voucher. In other implementations, sample transaction payment card 102 is provided by healthcare provider 108. In yet other implementations, sample transaction payment card 102 is provided by any other entity with an interest in the distribution of samples via electronic vouchers. Additionally, in certain implementations sample transaction payment card 102 is a one-time use card, being deactivated after it is redeemed for a sample from a merchant. In other implementations, sample transaction payment card 102 is capable of being used multiple times for multiple samples provided at a single or multiple merchant locations. In yet other implementations, sample transaction payment card 102 is a portable consumer device associated with a financial account that belongs to the patient card holder and may be capable of being used to conduct transactions for goods or services with various merchants.

Card read-write device 116 stores information relating to the electronic voucher selected by healthcare provider 108 on sample transaction payment card 102, including the account identifier associated with an account of the third-party sponsor of the electronic voucher.

In certain implementations, the electronic voucher may be for a sample made by a particular manufacturer. In such an implementation, the information may further include an identifier for the manufacturer. In certain implementations, the electronic voucher may be for a particular type of sample made by any manufacturer. In such an implementation, the information may further include an identifier for an acceptable generic alternative to the name-brand sample.

In certain implementations, the electronic voucher may be for a sample of an OTC medication or medical supply, such as, by way of example and not limitation, aspirin, bandages, salves, or creams. In such an implementation, the information may further include a type of sample, or category thereof, for which a sample transaction payment card is valid. By way of example and not limitation, the electronic voucher may be valid for a sample of all OTC pain relievers made by a particular manufacturer. Alternatively, the electronic voucher may be valid for a specific OTC pain reliever made by the manufacturer.

In certain implementations, the information also includes a prescription for a prescription medication. In such implementations, an image may be stored on sample transaction payment card 102 which includes the signature of healthcare provider 108. In certain implementations, the image may contain other information required in specific jurisdictions for a pharmacist to dispense a prescription medical supply. Such information, by way of example and not limitation, may include an image of the written prescription in the handwriting of the prescribing healthcare provider, the name of the patient, dosing instructions, and/or the refill amount. In certain implementations, the image may be of the free sample.

In such an implementation where a prescription is included, the electronic voucher may be for a sample of a medication not usually stocked at the pharmacy in sufficient amounts to completely fulfill a prescription. In other such implementations, the electronic voucher may be for a sample of a name-brand medication while the prescription may be for the generic equivalent.

In certain implementations, card read-write device 116 stores additional information on sample transaction payment card 102. Wherein the electronic voucher is for a sample of a prescription medication, card read-write device 116 may additionally store, by way of example and not limitation, identifiers for the prescribing healthcare provider 108, the patient, and the prescription medication for which a sample is to be provided.

In certain implementations, card read-write device 116 is a memory card reader-writer. In such an implementation, sample transaction payment card 102 is a smart card and the account identifier and any additional information is stored in the memory of an embedded chip. In certain implementations, sample transaction payment card 102 is a contact smart card having a contact area that when inserted into card read-write device 116 makes contact with electrical connectors capable of writing the information to memory. In certain implementations, sample transaction payment card 102 is a contactless smart card in which the chip communicates with card read-write device 116 through radio-frequency identification (RFID) induction technology.

In certain implementations, card read-write device 116 is a magnetic card reader. In such an implementation, sample transaction payment card 102 has a magnetic data stripe. The account identifier and any additional information is stored on sample transaction payment card 102 when the magnetic data stripe is placed in physical contact with a read-write head of card read-write device 116. In certain implementations, sample transaction payment card 102 includes both an embedded chip and a magnetic stripe.

In one implementation, sample transaction payment card 102 may also include an image 112 printed on a surface. Image 112 may be preprinted on sample transaction payment card 102 by the pharmaceutical company and may serve as an advertisement. Alternatively, image 112 may be printed by the card processor and may relate to the medication prescribed by healthcare provider 108 or the free sample. Further, sample transaction payment card 102 may display a flat or raised account number as well as the prescription name, quantity, instructions, patient name, prescribing healthcare provider's name, and any other relevant information.

Wherein the card processor system is capable of printing image 112 on sample transaction payment card 102, the device may include a card printer such as, for example, the Direct-to-Card (DTC) 450 or High Definition Printing (HDP) 5000 commercially available from Fargo Electronics, Inc., a corporation located in Eden Prairie, Minn.

In certain implementations, association of the electronic voucher with sample transaction payment card 102 further involves using the card processor system to provide an identifier of a sponsor account that will cover the cost of the sample and that is to be associated with sample transaction payment card 102. The card processor system also provides information regarding the electronic voucher selected by healthcare provider 108 for storage on sample transaction payment card 102 to be provided to a transaction handler, such as one or more of the transaction handler (th) 502 (FIG. 5), wherein the account identifier and the information is stored in a database. In such an implementation, the database may be used to verify the authenticity of an electronic voucher stored on a consumer payment device presented at a merchant's location for redemption of a sample.

Figure 1B:
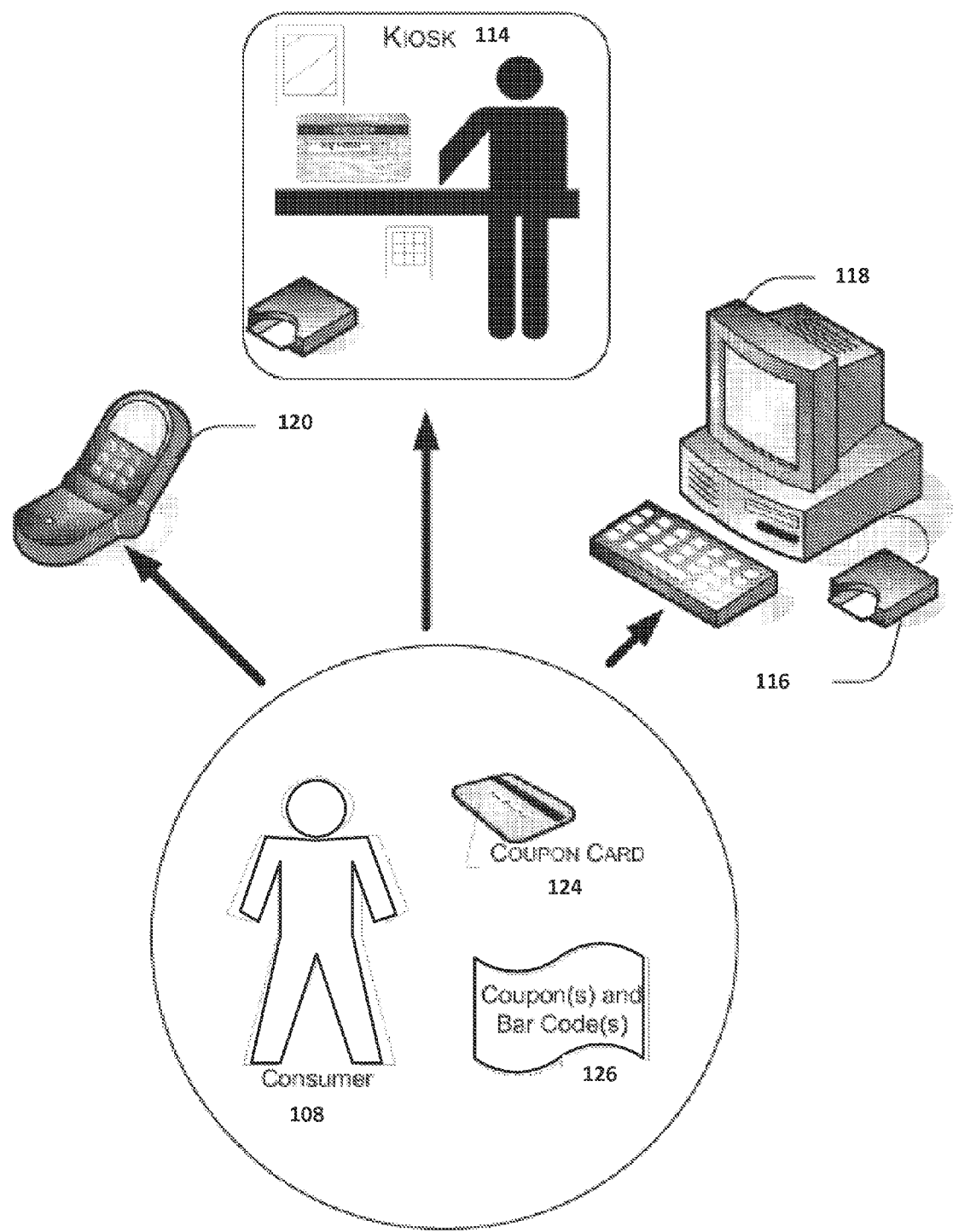

In the illustrated implementation of FIG. 1B, consumer 108 may associate a coupon card 126 with at least one electronic coupon using several methods. In one implementation, consumer 108 uses a web-enabled computer system 118 to connect to the World Wide Web, the Internet, or other network, and browse to a website having electronic coupons available for downloading as facilitated by a web service. In such an implementation, consumer 108 uses the browser to select at least one of the electronic coupons offered. Information relating to that electronic coupon is then downloaded to computer system 118, including an account identifier for the party offering, and willing to pay for the discount provide by, the electronic coupon.

In certain implementations, the information further includes the type of product or service, or category thereof, for which the electronic coupon is valid. By way of example and not limitation, the electronic coupon may be valid for all cleaning products made by a particular manufacturer. Alternatively, the electronic coupon may be valid for a specific dish soap made by the manufacturer.

In other implementations, the information also includes a merchant or manufacturer with which the electronic coupon is valid. In such an implementation, the electronic coupon may only be valid for use with a particular merchant or only for the purchase of a particular manufacturer's product. In other implementations, the information includes an expiration date, after which the electronic coupon is no longer valid. In yet other implementations, the information includes the number of goods or services eligible for a discount using the electronic coupon. By way of example and not limitation, the electronic coupon may be valid for discounts on up to three (3) bottles of a pain reliever. Alternatively, the electronic coupon may only be used when ten (10) car washes are purchased at the same time.

In certain implementations, the information also includes a bar code identifying the item or type of item for which the electronic coupon is valid. In such an implementation, the bar code is rendered on a print out 126 using a printer connected to computer system 118. The bar code may later be scanned by a scanner of a POS terminal to identify the item being purchased that is eligible for a discount using the electronic coupon.

Print out 126 includes a scannable copy of the bar code such that it may be later scanned by a scanner at a POS terminal to identify the type of item eligible for a discount using the electronic coupon. Print out 126 also serves as a reminder to consumer 108 of which electronic coupons are stored on coupon card 124.

In certain implementations, print out 126 includes advertisements. In certain implementations, print out 126 additionally includes information regarding soon-to-be-available electronic coupons.

Once the information relating to the selected electronic coupon is downloaded to computer system 118, the account identifier is written to a coupon card 124 using card read-write device 116. In certain implementations, card read-write device 116 is attached as a peripheral to computer system 118. In certain implementations, card read-write device 116 is a memory card reader. In such an implementation, coupon card 124 is a smart card and the account identifier is stored in the memory of an embedded chip. In certain implementations, coupon card 124 is a contact smart card having a contact area that when inserted into card read-write device 116 makes contact with electrical connectors capable of writing the information to memory. In certain implementations, coupon card 124 is a contactless smart card in which the chip communicates with card read-write device 116 through radio-frequency identification (RFID) induction technology.

In certain implementations, card read-write device 116 is a magnetic card reader. In such an implementation, coupon card 124 has a magnetic data stripe. The account identifier is stored on coupon card 124 when the magnetic data stripe is placed in physical contact with a read-write head of card read-write device 116.

In certain implementations, coupon card 124 includes both an embedded chip and a magnetic stripe. In other implementations, coupon card 124 is also a portable consumer device, such as a credit card, debit card, prepaid card, loyalty card or other such device associated with an account of consumer 108. In such implementations, consumer 108 may use coupon card 124 to both receive a discount and pay for the item.

Figure 2:
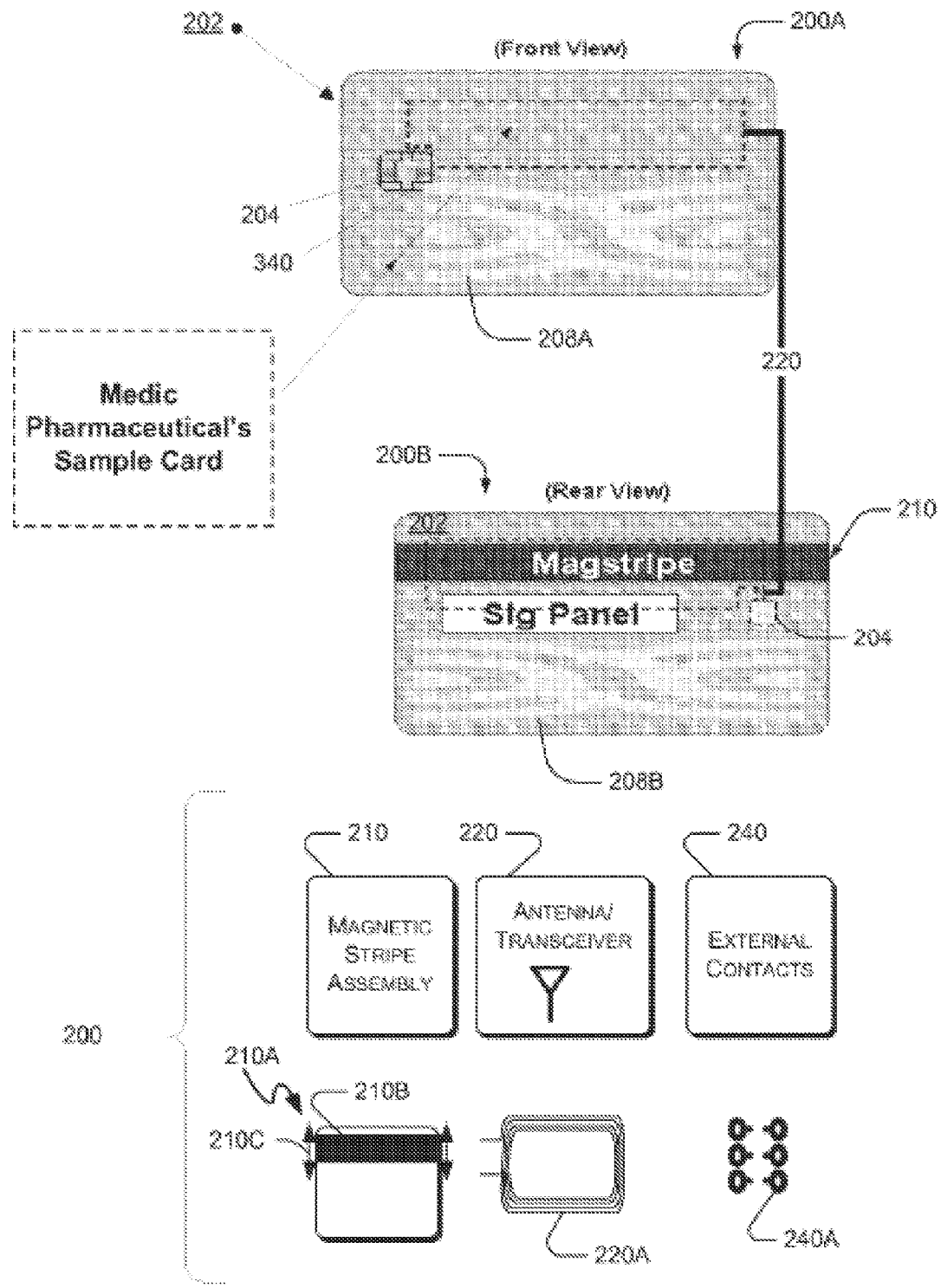
FIG. 2 illustrates possible alternative implementations of the data encoding area of a sample transaction payment card within embodiments of PPD.

In the illustrated implementation of FIG. 2, consumer 202 may also associate coupon card 204 with at least one electronic coupon using a dual range (i.e., long range wireless communications and short range wireless communications), web-enabled cellular telephone 210, where coupon card 204 is a smart card. In such implementations, consumer 202 uses the cellular telephony functionality of cellular telephone 210 to connect to the Internet or World Wide Web and browse to a website having electronic coupons provided by a web service. Upon selecting an electronic coupon, the associated information is downloaded to cellular telephone 210, including the account identifier for the third-party sponsoring the electronic coupon.

In such implementations where the information downloaded also includes a bar code, the bar code is capable of being rendered on the display of cellular telephone 210. The bar code can later be scanned by a scanner at a POS terminal to identify the type of item eligible for a discount using the electronic coupon.

Once the information relating to the selected electronic coupon is downloaded to cellular telephone 210, the account identifier associated with the sponsor of the electronic coupon is written to coupon card 204 using a moblet stored on cellular telephone 210. The moblet is executed to provide functionality to short range wireless communication that writes to the memory of coupon card 204, such as via a near field communication (NFC) card read-write application capable of using wireless NFC to read and write data to the memory of coupon card 204.

In the illustrated implementation of FIG. 2, consumer 202 may also associate a coupon card 204 with at least one electronic coupon using a kiosk 214. Kiosk 214 is in communication with a database (not shown), preferably kept in one or more device storage devices, capable of storing and relating information regarding the available electronic coupons. In one implementation, a third-party offering at least one electronic coupon has access to the database and may send to and receive from the database information such as the number of electronic coupons used, the number of electronic coupons remaining, or any other relevant information.

When using kiosk 214, consumer 202 is presented with a user interface displaying a plurality of electronic coupons and uses an input device to make a selection. In one implementation, consumer 202 then receives from kiosk 214 a coupon card 204. In such an implementation, kiosk 214 includes a stack of blank coupon cards which may be issued to consumer 202. In other implementations, consumer 202 obtains coupon card 204 and provides it to kiosk 214 via a card receiving device to have the selected electronic coupons stored thereon. In such implementations, consumer 202 may purchase coupon card 204 from a merchant. In other implementations, consumer 202 may receive coupon card 204 from the third-party, a merchant, or any other entity having an interest in providing electronic coupons. In yet other implementations, coupon card 204 is also a portable consumer device and is issued by an issuer to consumer 202 (i.e., the consumer's credit, debit, gift, or pre-paid card).

In using kiosk 214 to associate coupon card 204 with at least one electronic coupon, kiosk 214 stores information relating to the electronic coupon selected by consumer 202 on coupon card 204, including the account identifier associated with an account of the electronic coupon sponsor.

In those implementations where the selected electronic coupon is also associated with a bar code identifying the type of item for which the electronic coupon is valid, kiosk 214 additionally dispensed to consumer 202 a print out 206 having the bar code printed thereon. The print out may later be scanned by a scanner at a POS terminal, as would a typical coupon.

Turning to FIG. 2, both a front view 200A and a rear view 200B of an exemplary sample transaction payment card 202 are presented. Images may be displayed on both sides of sample transaction payment card 202, with image 208A on the front view 200A being either the same as or different from image 208B on the rear view 200B. In this illustration, the front view 200A also displays information about the provider of sample transaction payment card 202.

FIG. 2 also shows exemplary implementations of a data encoding area of sample transaction payment card 202. The data encoding area may include an optional shielding element, which allows desired electromagnetic, optical, or radiative signals to penetrate while protecting the data encoding area from physical abuse or damage. Sample transaction payment card 202 may optionally have areas outside of the data encoding area shielded from physical abuse or otherwise acceptable forms of electromagnetic radiation. Some of the acceptable signals that are allowed to penetrate the shielding and may include, but are not limited to, signals accompanying a magnetic field, RFID signals, IrDA signals, visible light, invisible light, modulated laser, and/or modulated RF communication signals. By way of example and not limitation, a selective shielding element may comprise a clear plastic shield, conformal coatings, an opaque plastic shield, or a clear thin film, depending on the implementation of the data encoding area.

Non-limiting examples of the data encoding area are shown at reference numeral 200, and include a magnetic stripe assembly 210, an antenna and/or transceiver 220, and electrical contacts 240. Magnetic stripe assembly 210 may comprise, in the implementation shown as 210A, a reprogrammable magnetic stripe assembly 210B that accepts data and/or commands from a processor and formats and renders that data into a form on a magnetic stripe that is readable by conventional merchant magnetic stripe-reading point of sale (POS) terminals. In this manner, the processor may program a particular account for use in a transaction as a function of user input selecting the account. Alternatively, the processor may erase the magnetic stripe of assembly 210, rendering the card useless in the event of its loss or theft. In the implementation shown as 210A, magnetic stripe assembly 210B at least partially slidably moves 210C into and out of an assembly of sample transaction payment card 202 (partial view shown), allowing sample transaction payment card 202 to conduct a transaction at a point of sale terminal that includes a magnetic stripe reader.

Continuing with FIG. 2, another implementation of the data encoding area is shown as an antenna and/or transceiver 220. Antenna and/or transceiver 220 may include commonly used loop inductors such as the one shown 220A or in those shown in related ISO standards for RF-readable smart cards. With such an interface, account data may be translated, modulated and transmitted in a manner acceptable by an RF contactless merchant POS terminal, an 802.11 WiFi or WiMax network, or by a cellular or RF communications network. For instance, antenna and/or transceiver 220 may receive a wireless communication from a card read-write device, where the wireless communication carries data for a sponsor's electronic voucher account that is to be written in memory to the data encoding area 200.

Electrical contacts 240 are yet another alternative implementation of the data encoding area shown in FIG. 2. With sample transaction payment card 202 possessing physical contacts such as an array of conductive pads or shapes 240A, sample transaction payment card 202 may be placed in physical contact with merchant POS terminals, and electrical contacts 240 may establish connectivity between imbedded integrated circuit 204 and the merchant's financial processing system. The processor may relay account-related information to the merchant POS terminal through the contact interface, thereby allowing sample transaction payment card 202 to be utilized with the large number of preexisting merchant POS terminals.

Within the exemplary payment processing system depicted in FIG. 5 and described below, FIG. 3 illustrates the general environment wherein a sample transaction payment card, such as sample transaction payment card 202 (FIG. 2) obtained by the environment described in connection with FIG. 1, is used by a patient 314 to receive a sample prescription or medical item from a merchant, such as a pharmacy (n) 310, that had been prescribed by a prescribing healthcare provider (p) 322 to patient 314. To start, at the POS terminal of pharmacy 310, patient 314 presents to Pharmacy 310 sample transaction payment card (q) 302. Pharmacy 310 uses a card reader associated with the POS terminal to read the information stored on sample transaction payment card 302, including the account identifier associated with the one or more electronic vouchers being sponsored, respectively, by one or more sponsors 312 (one such sponsor is indicated in FIG. 3 as sponsor (r) 312). In certain implementations, sample transaction payment card 302 is read by swiping sample transaction payment card 302 through the POS terminal to read data magnetically encoded in its magnetic stripe. In other implementations, the POS terminal reads sample transaction payment card 302 using a contactless technology, such as RFID, when patient 314 is near the POS terminal. In yet other implementations, to be read, sample transaction payment card 302 is inserted into the POS terminal such that external contacts on sample transaction payment card 302 establish connectivity with the POS terminal.

In certain implementations, other information is also read from sample transaction payment card 302, such as, by way of example and not limitation, an expiration date, a sample type, or patient 314's name. In such implementations, the POS terminal may determine whether the electronic voucher is valid for the sample requested. This may occur, by way of example and not limitation, by comparing the current date with the expiration data of the electronic voucher.

In certain implementations, the POS terminal may be connected to a database storing information regarding prescriptions patient 314 has had filled at pharmacy 310 or any related pharmacy 310(*n*). In such an implementation, the database may be used to determine whether patient 314 is taking any other medication that may interacted with the sample to be distributed. Wherein the sample is of a controlled substance included on a schedule, such a database may additionally be used to force compliance with regulations promulgated by the United States Drug Enforcement Agency. In such implementations, the database may be used to verify that use of the electronic voucher would not allow patient 314 to receive more then the legally allowed limit. By way of example and not limitation, where the sample is for a medication listed on Schedule II, such as Methadone, Oxycodone, or Fentanyl, patients are limited to a thirty (30) day supply unless they meet a legal exception. Thus, the database may be used to determine whether distribution of the sample, alone or in combination with other samples or prescriptions, would give patient 314 more than a thirty (30) day supply. Further, the prescription date may be checked against the date on which patient 314 is requesting the sample to ensure that the sample is being distributed within the legally allowed time frame from the prescription date. Alternatively, wherein the medication is restricted by the number of refills which may be distributed within a given time frame, such as medications on Schedule III and Schedule IV, the data base may be used to determine whether distribution of the sample may be considered a "refill" exceeding the allowed amount under law during that timeframe.

In certain implementations, patient 314 is requested to present identification. In such an implementation, the identification may be checked against a patient identifier read from sample transaction payment card 302 in order to verify that patient 314 was the same patient who was given sample transaction payment card 302 from healthcare provider 322. Alternatively, the identification may be used to verify that the individual presenting sample transaction payment card 302 is authorized to receive medication on behalf of patient 314, such as in the case of a parent or spouse of patient 314.

Upon receipt of sample transaction payment card 302, the transaction is processed similarly to the method to be described in connection with FIG. 5. Pharmacy 310 submits an authorization request to acquirer 308, which includes the account identifier read from sample transaction payment card 302. In certain implementations where consumer is also making a purchase of a good or a service, an account identifier of a financial account issued by an issuer to consumer 314 and associated with portable consumer transaction payment device 302 is also included in the authorization request.

In certain implementations, the authorization request is for only some of the samples or amounts described by the electronic voucher associated with the account identifier of sample transaction payment card 302. In such an implementation, pharmacy 310 can send the authorization request only for the types of medications or the amount of medication the pharmacy is capable of distributing at that time. In such a situation, patient 314 could then use the card at another pharmacy to receive the rest of the sample associated with the account identifier of the card. In such cases, memory of card 302 will be accordingly updated to reflect the progressive partial and complete filling of a prescription dispensed by each respective pharmacist (n) 310 to patient 314.

In certain implementations, the authorization request may additionally include a different account identifier that is separately supplied by the patient 314 (or agent thereof), where patient 314 intends to pay for the portion of the transaction with the pharmacist (n) 310 that is not free, and where that portion of the purchase is to be paid for by the patent's use of their personal credit card, debit card, personal check written on a checking account, or other portable consumer transaction payment device.

Where acquirer 308 is not the same entity as the issuer of the account associated with the account identifier read from sample transaction payment card 302, acquirer 308 forwards the transaction information to a transaction handler 306, who in turn forwards it to issuer 304 to verify that the account associated with electronic voucher sponsor 312 contains sufficient funds to reimburse pharmacy 310 for the sample.

Upon receipt of a reply from issuer 304, transaction handler 306 forwards an authorization response to acquirer 308, who forwards it to pharmacy 310. Where the authorization response contains an approval of the use of the electronic voucher, patient 314 is given the associated sample free of charge.

In certain implementations, the authorization response is only a partial response. In such implementations, the authorization request may have included types of samples or amounts not associated with the account identifier of sample transaction payment card 302.

In certain implementations, pharmacy 310 invalidates or deletes the electronic voucher(s) stored on sample transaction payment card 302 once the sample has been provided to patient 314. In certain implementations, sample transaction payment card 302 may be a one-time use card. In such an implementation, pharmacy 310 may forgo returning sample transaction payment card 302 to patient 314. In certain implementations, sample transaction payment card 302 is deactivated only after all of the samples described in the sample information have been redeemed by patient 314. In such an implementation, patient 314 may fill only part of the sample at any given time or may receive portions of the samples from different pharmacies. In another implementation, the PPD may have the electronic voucher stored on portable consumer transaction payment device 302. Alternatively, in such implementations, the authorization request may have included items patient 314 wishes to purchase using a financial account belonging to patient 314 and also associated with portable consumer transaction payment device 302 (e.g., the patient's personal credit card account number).

In other implementations, sample transaction payment card 302 may be a multiple use card and is therefore not deactivated. In such an implementation, sample transaction payment card 302 may be used to store subsequent electronic vouchers and therefore is returned to patient 314. Alternatively, sample transaction payment card 302 may also be a credit card, debit card, or other form of a portable consumer device that can be used to conduct transactions for goods or services with merchants.

In certain implementations, approval of the transaction may be more involved. In such implementations, the authorization request includes additional information, by way of example and not limitation, the sample medication to be distributed, the prescribing healthcare provider, and/or the sponsor of the electronic voucher. In one implementation, database 316 may be used to, by way of example and not limitation, to verify the number of samples authorized by electronic voucher sponsor 312 for distribution generally or for distribution by a specific doctor. In other implementations, database 316 may be used to verify the types of prescription medications or OTC healthcare items a healthcare provider may distribute using a sample transaction payment card. The number and type of samples distributed in the transaction may then be reflected against the amount and types the healthcare provider has available to distribute in the future. In further implementations, the PPD may verify that electronic voucher sponsor 312 has issued the electronic voucher consumer 314 is attempting to use. In such an implementation, the authorization process may include comparing the additional information provided against information stored in database 316. In other implementations, database 316 is used to keep a tally of the electronic vouchers used by consumers. In such an implementation, this information may then be used by electronic voucher sponsor 312 in deciding future electronic vouchers to issue or for identifying specific consumers for targeted advertising. In still other implementations, the additional information includes the identifier for the advertisement that was presented to consumer 314 with the electronic voucher being used, such as the advertisement on sample card 302. In such an implementation, the electronic voucher sponsor 312 may charge another entity a fee for each time the advertisement has been presented with the electronic voucher.

In other implementations, database 318 is used. Database 318 may contain information regarding all sample transaction payment cards issued for distribution of each type of sample medication or healthcare item. By way of example and not limitation, database 318 may be used to verify the authenticity of sample transaction payment card 302 or that sample transaction payment card 302 has only been used once. In further implementations, database 318 may contain information regarding the account issued to each electronic voucher sponsor 312($r$), where electronic voucher sponsor 312($r$) is one of up to 'R' electronic voucher sponsors. In such implementations, database 318 may be used to verify that the account identifier read from sample card 302 is associated with one of the 'R' electronic voucher sponsors. Database 318 may additionally be used to verify that the associated account contains sufficient funds with which to reimburse retail merchant 310 for the sample distributed.

In yet another implementation, another database, database 320, contains information regarding all activated sample transaction payment cards, wherein prescribing healthcare provider 322 activates sample transaction payment card 302 prior to giving it to patient 314. Alternatively, a representative of electronic voucher sponsor 312 may activate sample transaction payment card 302 prior to providing it to healthcare provider 322. Approval of the transaction request may, in such an implementation, depend upon verification that sample transaction payment card 302 is activated.

Once the authorization request is approved and the sample associated with the electronic voucher stored on sample transaction payment card 302 is distributed, pharmacy 310 may submit a payment request to payment processing system 300 for reimbursement from electronic voucher sponsor 312's account for the cost of the sample. Specifically, pharmacy 310 submits a request for payment to acquirer 308. Where acquirer 308 is not the same entity as the issuer of the account associated with the account identifier stored on sample transaction payment card 302, acquirer 308 forwards the request to transaction handler 306. Transaction handler 306 in turn requests payment for the sample from issuer 304, where issuer 304 is the issuer of the account associated with electronic voucher sponsor 312. Issuer 304 debits the account and forwards the payment to transaction handler 306 who forwards the payment to acquirer 308. Finally, acquirer 308 credits the account of pharmacy 310 for the cost of the distributed sample.

Figure 3A:
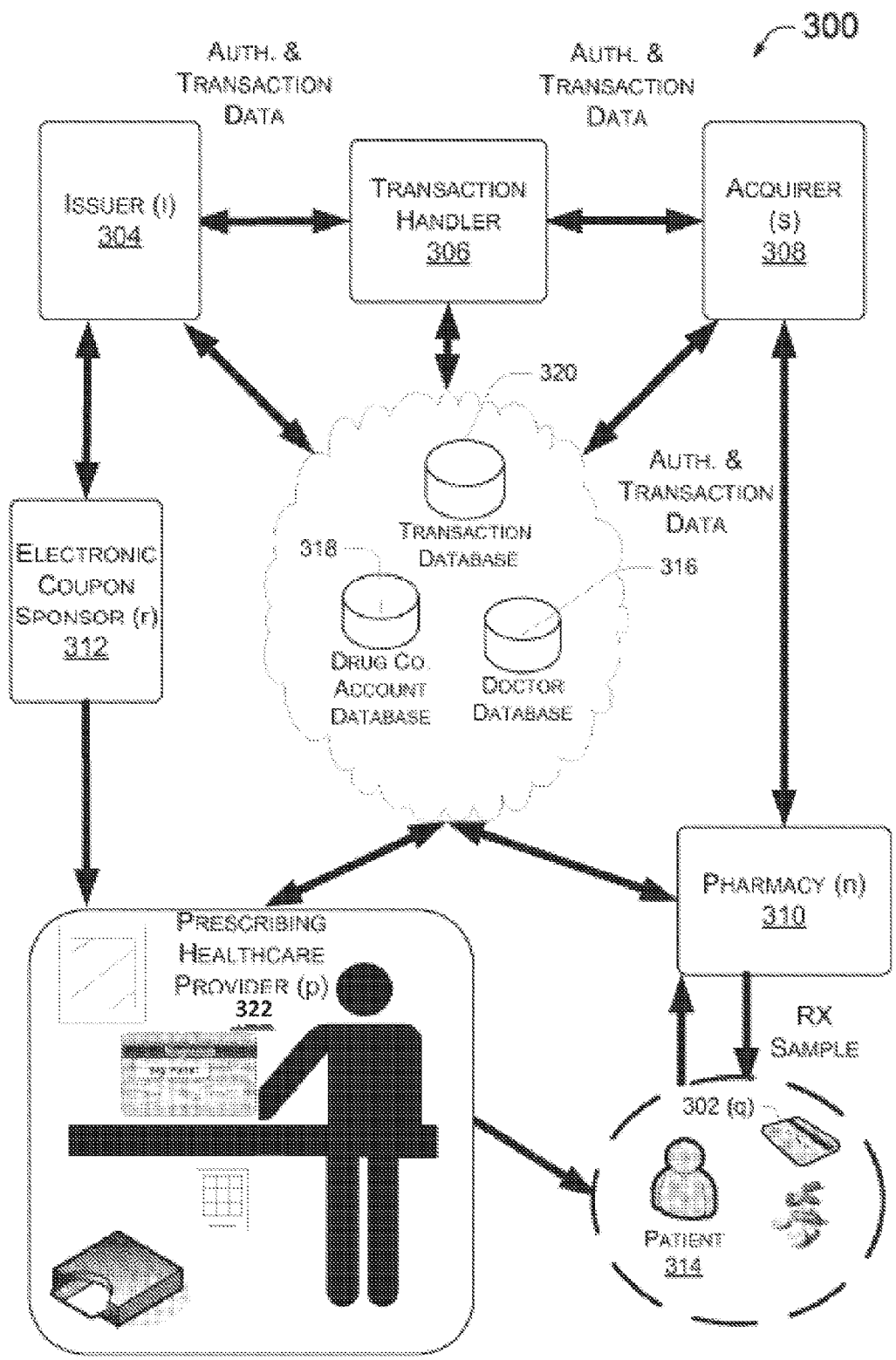
FIGS. 3A-3B depict the environment within FIG. 5 where a sample transaction payment card is used by a patient to obtain a sample within embodiments of PPD.
Figure 3B:
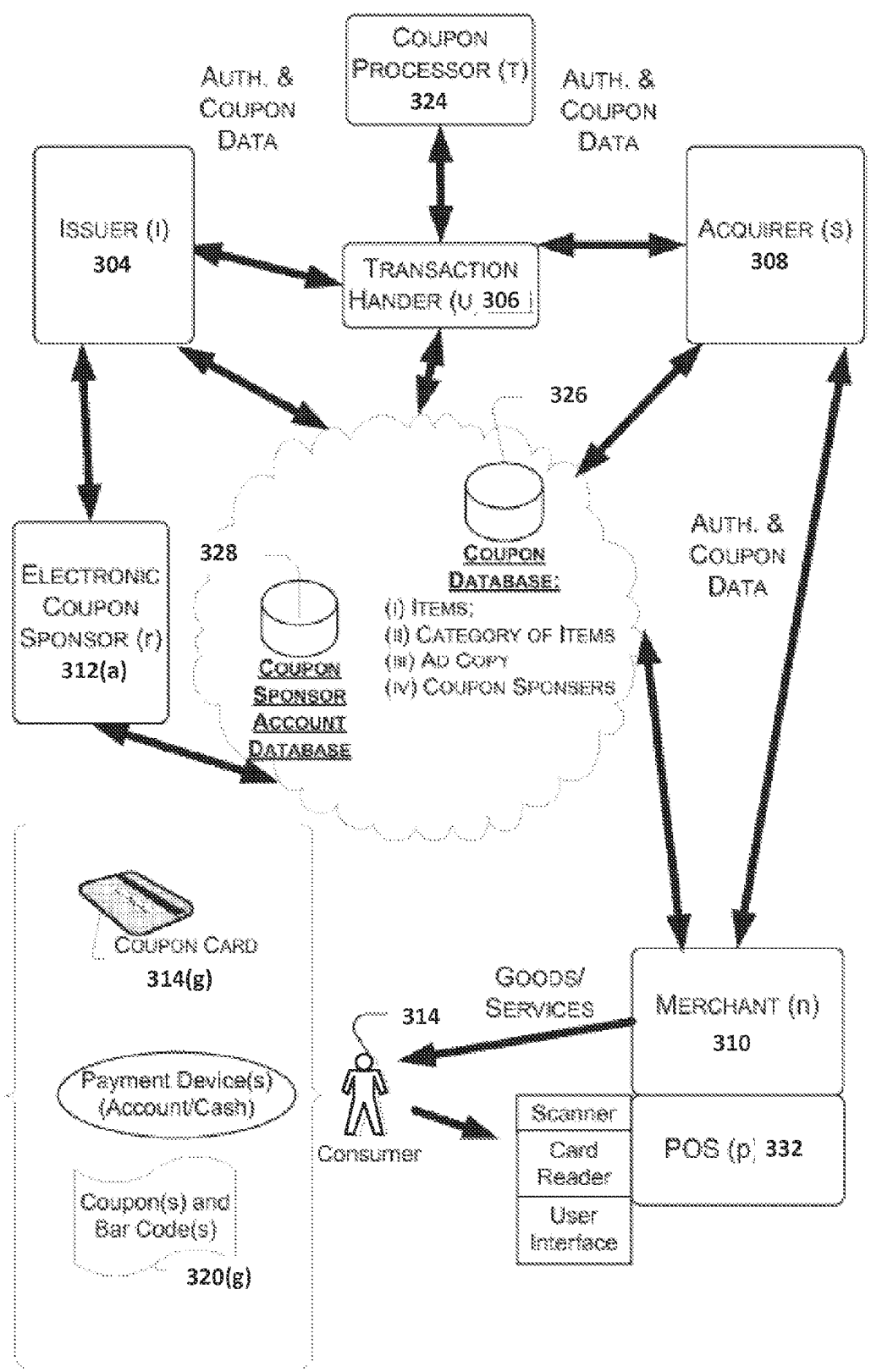

FIG. 3B provides an alternative embodiment to FIG. 3A, illustrating a coupon card usage processing flow within embodiments of the PPD. Similar to that described in FIG. 3A, a consumer to receive a discount on the purchase of goods and services. To start, at POS terminal 332, consumer 314 presents to merchant 310 coupon card 314($g$) along with the item(s) consumer 314 wishes to purchase. Merchant 310 uses a card reader associated with POS terminal 322 to read the information stored on coupon card 314($g$), including the account identifier associated with electronic coupon sponsor 312($a$). In certain implementations, coupon card 314($g$) is read by swiping coupon card 314($g$) through POS terminal 332 to read data magnetically encoded in its magstripe. In other implementations, POS terminal 332 reads coupon card 314($g$) using a contactless technology, such as RFID, when consumer 314 is near POS terminal 332. In yet other implementations, to be read, coupon card 314($g$) is inserted into POS terminal 332 such that external contacts on coupon card 414 establish connectivity with POS terminal 332.

In certain implementations, other information is also read from coupon card 314($g$), such as, by way of example and not limitation, an expiration date, an item type, or an item quantity. In such implementations, POS terminal 332 may determine whether the electronic coupon is valid for the item being purchased. This may occur, by way of example and not limitation, by comparing the current date with the expiration data of the electronic coupon. Alternatively, POS terminal 332 may determine whether consumer 314 has purchased the quantity of the discounted item specified. POS terminal 332 may also verify whether consumer 314 has actually purchased the item or item type for which the electronic coupon is applicable.

In one implementation, consumer 314 additionally provides print out 320($g$) to merchant 310. Print out 320($g$) has a bar code printed thereon that identifies the item eligible for a discount using the electronic coupon stored on coupon card 314($g$). In such an implementation, the bar code is scanned with a scanner associated with POS terminal 332 to identify the item that is eligible for the discount.

In certain implementations, merchant 310 may additionally enter the amount of the discount into POS terminal 332. In such implementations, the discount amount may be printed on print out. In other implementations, the discount amount is read by POS terminal 332 from coupon card 314($g$). In certain implementations, POS terminal 332 calculates the discount amount. This may occur, by way of example and not limitation, where the discount is valid for the purchase of multiple items. In such an implementation, POS terminal 332 may calculate the discount amount by multiplying the discount per item by the number of items purchased.

Upon receipt of coupon card 314($g$), the transaction is processed similarly to a method described below in connection with FIG. 1. Merchant 310 submits an authorization request to acquirer 308 via POS terminal 332, which includes the account identifier read from coupon card 314($g$).

In certain implementations, the authorization request may additionally include an account identifier associated with consumer 314 where consumer 314 has paid for the purchase using a credit card, debit card, or other portable consumer device.

Where acquirer 308 is not the same entity as issuer 304, acquirer 308 forwards the transaction information to a transaction handler 306, who in turn forwards it to issuer 304 to verify that the account associated with electronic coupon sponsor 312($a$) contains sufficient funds to reimburse merchant 310 for the discount.

Upon receipt of a reply from issuer 304, transaction handler 306 forwards an authorization response to acquirer 308, who forwards it to POS terminal 332 of merchant 310. Where the authorization response contains an approval of the use of the electronic coupon, consumer 314 is given a discount on the retail purchase price of the item.

In certain implementations, merchant 310 invalidates or deletes the electronic coupon(s) stored on coupon card 314(g) using POS terminal 332 once the discount has been applied. In certain implementations, coupon card 314(g) may be a one-time use card. In such an implementation, merchant 310 may forgo returning coupon card 314(g) to consumer 314. In other implementations, coupon card 320(g) may be used to store subsequent electronic coupons and therefore is returned to consumer 314.

In certain implementations, approval of the transaction may be more involved. In such implementations, the authorization request includes additional information, by way of example and not limitation, the item, the item type, and/or the sponsor of the electronic coupon. In certain implementations this information is forwarded by transaction handler 306 to coupon processor 324 for processing. In one implementation, database 326 may be used to, by way of example and not limitation, verify that electronic coupon sponsor 312 has issued the electronic coupon consumer 314 is attempting to use. In such an implementation, the authorization process may include a comparison, performed by coupon processor 324, of the additional information provided against information stored in database 326. In yet other implementations, coupon processor 324 adds a notation to a coupon stored in database 326 once it has been used by a consumer, thereby preventing the coupon from being used more than once. Coupon processor 324 may have direct access to database 326 or may access database 326 via transaction handler 306.

In other implementations, coupon processor 324 uses database 326 to keep a tally of the electronic coupons used by consumers. In such an implementation, this information is used by electronic coupon sponsor 312(a) in deciding future electronic coupons to issue or for identifying specific consumers for targeted advertising. In still other implementations, the additional information includes an identifier for the advertisement that was presented to consumer 314 with the electronic coupon being used. In such an implementation, after the information is stored in database 326 by coupon processor 324, electronic coupon sponsor 312(a) may charge another entity a fee for each time the advertisement is shown to consumers. Alternatively, electronic coupon sponsor 312(a) may change the advertisement associated with an electronic coupon after the advertisement has been presented with the electronic coupon a given number of times.

In other implementations, database 328 is used. As with database 326, coupon processor 324 may access database 328 directly or via transaction handler 306. Database 328 may contain information regarding the account issued to each coupon sponsor 312(a), where electronic coupon sponsor 312(a) is one of (R) coupon sponsors. In such implementations, coupon processor 324 uses database 328 to verify that the account identifier read from coupon card 314(g) is associated with one of the (R) electronic coupon sponsors. Database 328 may additionally be used to verify that the associated account contains funds sufficient to reimburse merchant 310 for the discount applied.

In certain implementations, coupon processor 324 is the same entity as transaction handler 306. In other implementations, coupon processor 424 is a separate entity from transaction handler 306. Similar as discussed in FIG. 3A, the merchant 310 may submit the transaction to payment processing system 300 for settlement and clearing.

As will be understood by a person of ordinary skill in the art, the processes described in connection with FIGS. 3A-3B are equally applicable to the situation where a patient uses a sample transaction payment card having multiple electronic vouchers stored thereon to receive several different samples, and/or the situation where a consumer uses a coupon card having multiple electronic coupons stored thereon to receive a discount on several items. In such a situation, the electronic vouchers and/or coupons may be provided by different electronic voucher/coupon sponsors (i.e., sponsor (r) 312, sponsor (r+1) 312, sponsor (r+2) 312, etc.) having accounts issued by different issuers for the purpose of reimbursing each dispensing pharmacist (n) 310 for samples. Further, it will be clear to a person of ordinary skill in the art that a sample transaction payment card may have multiple electronic vouchers/coupons stored thereon that are valid at different pharmacies and/or merchants, each pharmacy and/or merchant having a different acquirer.

Figure 4:
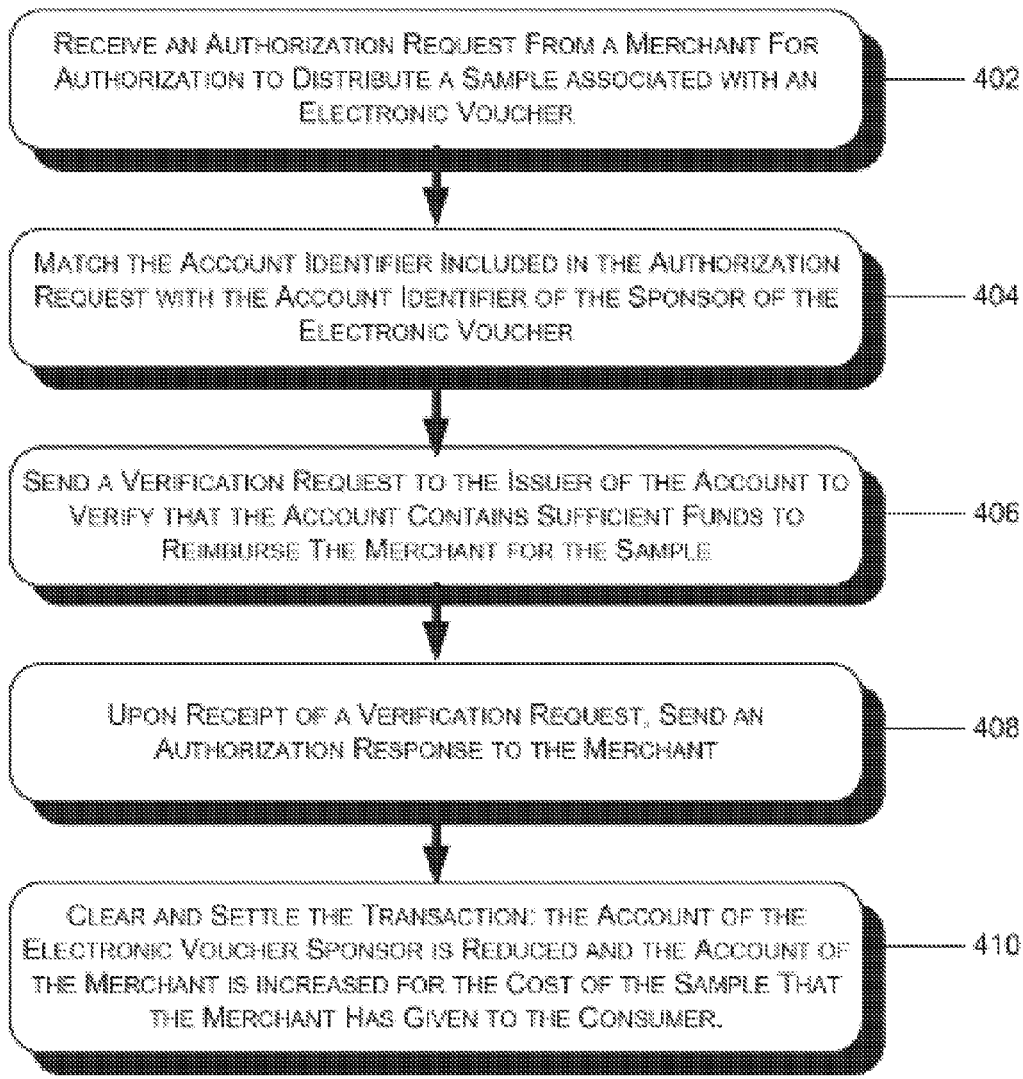
FIG. 4 depicts a flow chart of an exemplary method used by a transaction handler to process an electronic voucher stored on a sample transaction payment card within embodiments of PPD.

Turning now to FIG. 4, a flow chart of an exemplary method used by a transaction handler to process an electronic voucher stored on a consumer payment device is presented. As indicated by block 402, the transaction handler receives an authorization request from a merchant (e.g., via the merchant's acquirer), requesting authorization to distribute a sample associated with an electronic voucher to a patient. Upon receipt of the request, the transaction handler matches the account identifier included in the request with the account identifier associated with the electronic voucher sponsor, as indicated by block 404. In certain implementations, if the account identifier included in the request does not match the account identifier associated with the electronic voucher sponsor, the transaction handler sends an authorization response to the merchant indicating that the transaction is not authorized such that there will be a denial of the distribution of the free sample to the patient. In such an implementation, the process may end.

In the illustrated implementation of FIG. 4, the transaction handler next sends a request to the issuer of the account associated with the electronic voucher sponsor requesting verification that the account contains sufficient funds to reimburse the merchant for the sample, as indicated by block 406. As indicated by block 408, upon receipt of a response from the issuer, the transaction handler sends a response to the merchant. Where the issuer confirms that the account contains sufficient funds, the authorization request may contain an approval. Finally, as indicated by block 410, the transaction handler clears and settles the transaction by facilitating a process in which the issuer debits the account of the electronic voucher sponsor and an acquirer for the pharmacist credits the pharmacist's account for the cost of the free prescription medical supply sample that the pharmacist compounded and dispensed to the patient.

In certain implementations, individual blocks described above may be combined, eliminated, or reordered.

In certain implementations, instructions are encoded in computer readable medium wherein those instructions are executed by a processor to perform one or more of the blocks 402, 404, 406, 408, and 410 recited in FIG. 4.

In certain implementations, individual steps described above in relation to FIG. 4 may be combined, eliminated, or reordered. In yet other implementations, instructions reside in any other computer program product, where those instructions are executed by a computer external to, or internal to, a computing system to perform one or more of the blocks 402, 404, 406, 408, and 410 recited in FIG. 4. In either case the instructions may be encoded in a computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, compactflash, smartmedia, and the like.

An Exemplary Transaction Processing System

Figure 5:
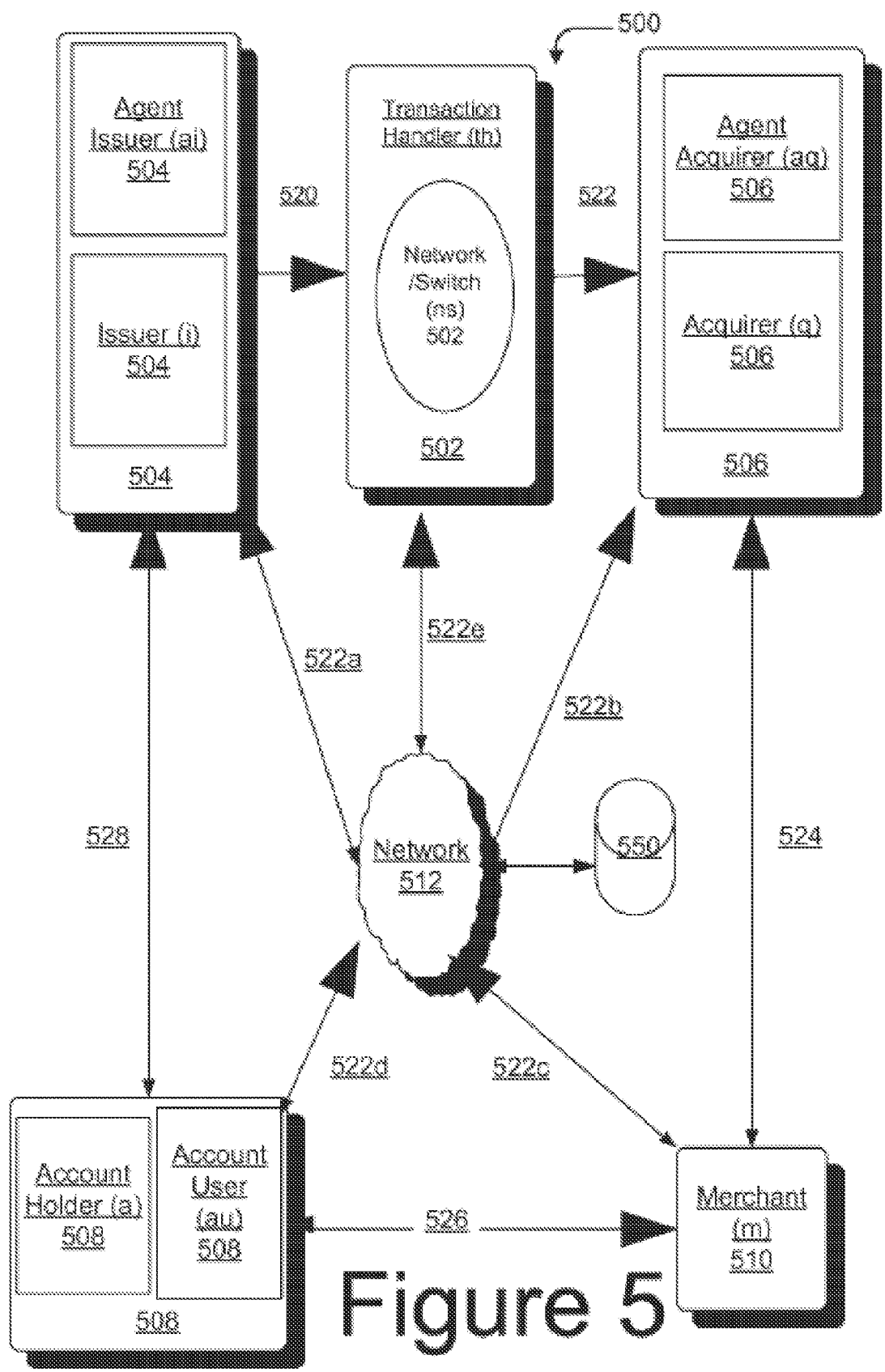
FIG. 5 illustrates an exemplary payment processing network, depicting the general environment where a sample transaction payment card may be used by a card holder to obtain a sample within embodiments of PPD.

Referring to FIG. 5, a transaction processing system 500 is seen. The general environment of FIG. 5 include that of a merchant (m) 510, such as the merchant, who can conduct a transaction for goods and/or services with an account user (au) (e.g., consumer) on an account issued to an account holder (a) 508 by an issuer (i) 504, where the processes of paying and being paid for the transaction are coordinated by at least one transaction handler (th) 502 (e.g., the transaction handler) (collectively "users"). The transaction includes participation from different entities that are each a component of the transaction processing system 500.

The transaction processing system 500 may have at least one of a plurality of transaction handlers (th) 502 that includes transaction handler (1) 502 through transaction handler (TH) 502, where TH can be up to and greater than an eight digit integer.

The transaction processing system 500 has a plurality of merchants (m) 510 that includes merchant (1) 510 through merchant (M) 510, where M can be up to and greater than an eight digit integer. Merchant (m) 510 may be a person or entity that sells goods and/or services. Merchant (m) 510 may also be, for instance, a manufacturer, a distributor, a retailer, a load agent, a drugstore, a grocery store, a gas station, a hardware store, a supermarket, a boutique, a restaurant, or a doctor's office. In a business-to-business setting, the account holder (a) 508 may be a second merchant (m) 510 making a purchase from another merchant (m) 510.

Transaction processing system 500 includes account user (1) 508 through account user (AU) 508, where AU can be as large as a ten digit integer or larger. Each account user (au) conducts a transaction with merchant (m) 510 for goods and/ or services using the account that has been issued by an issuer (i) 504 to a corresponding account holder (a) 508. Data from the transaction on the account is collected by the merchant (m) 510 and forwarded to a corresponding acquirer (a) 506. Acquirer (a) 506 forwards the data to transaction handler (th) 502 who facilitates payment for the transaction from the account issued by the issuer (i) 504 to account holder (a) 508.

Transaction processing system 500 has a plurality of acquirers (q) 506. Each acquirer (q) 506 may be assisted in processing one or more transactions by a corresponding agent acquirer (aq) 506, where 'q' can be an integer from 1 to Q, where aq can be an integer from 1 to AQ, and where Q and AQ can be as large as a eight digit integer or larger. Each acquirer (q) 506 may be assisted in processing one or more transactions by a corresponding agent acquirer (aq) 506, where 'q' can be an integer from 1 to Q, where aq can be an integer from 1 to AQ, and where Q and AQ can be as large as a eight digit integer or larger.

The transaction handler (th) 502 may process a plurality of transactions within the transaction processing system 500. The transaction handler (th) 502 can include one or a plurality or networks and switches (ns) 502. Each network/switch (ns) 502 can be a mainframe computer in a geographic location different than each other network/switch (ns) 502, where 'ns' is an integer from one to NS, and where NS can be as large as a four digit integer or larger.

Dedicated communication systems 520, 522 (e.g., private communication network(s)) facilitate communication between the transaction handler (th) 502 and each issuer (i) 504 and each acquirer (a) 506. A Network 512, via e-mail, the World Wide Web, cellular telephony, and/or other optionally public and private communications systems, can facilitate communications 522a-522e among and between each issuer (i) 504, each acquirer (a) 506, each merchant (m) 510, each account holder (a) 508, and the transaction handler (th) 502. Alternatively and optionally, one or more dedicated communication systems 524, 526, and 528 can facilitate respective communications between each acquirer (a) 506 and each merchant (m) 510, each merchant (m) and each account holder (a) 508, and each account holder (a) 508 and each issuer (i) 504, respectively.

The Network 512 may represent any of a variety of suitable means for exchanging data, such as: an Internet, an intranet, an extranet, a wide area network (WAN), a local area network (LAN), a virtual private network, a satellite communications network, an Automatic Teller Machine (ATM) network, an interactive television network, or any combination of the forgoing. Network 512 may contain either or both wired and wireless connections for the transmission of signals including electrical, magnetic, and a combination thereof. Examples of such connections are known in the art and include: radio frequency connections, optical connections, etc. To illustrate, the connection for the transmission of signals may be a telephone link, a Digital Subscriber Line, or cable link. Moreover, network 512 may utilize any of a variety of communication protocols, such as Transmission Control Protocol/ Internet Protocol (TCP/IP), for example. There may be multiple nodes within the network 512, each of which may conduct some level of processing on the data transmitted within the transaction processing system 500.

Users of the transaction processing system 500 may interact with one another or receive data about one another within the transaction processing system 500 using any of a variety of communication devices. The communication device may have a processing unit operatively connected to a display and memory such as Random Access Memory ("RAM") and/or Read-Only Memory ("ROM"). The communication device may be combination of hardware and software that enables an input device such as a keyboard, a mouse, a stylus and touch screen, or the like.

For example, use of the transaction processing system 500 by the account holder (a) 508 may include the use of a portable consumer device (PCD), which can be an implementation of a portable prescription transaction payment device. The PCD may be one of the communication devices, or may be used in conjunction with, or as part of, the communication device. The PCD may be in a form factor that can be a card (e.g., bank card, payment card, financial card, credit card, charge card, debit card, gift card, transit pass, smart card, access card, a payroll card, security card, healthcare card, or telephone card), a tag, a wristwatch, wrist band, a key ring, a fob (e.g., SPEEDPASS® commercially available from ExxonMobil Corporation), a machine readable medium containing account information, a pager, a cellular telephone, a personal digital assistant, a digital audio player, a computer (e.g., laptop computer), a set-top box, a portable workstation, a minicomputer, or a combination thereof. The PCD may have near field or far field communication capabilities (e.g., satellite communication or communication to cell sites of a cellular network) for telephony or data transfer such as communication with a global positioning system (GPS). The PCD may support a number of services such as SMS for text messaging and Multimedia Messaging Service (MMS) for transfer of photographs and videos, electronic mail (email) access.

The PCD may include a computer readable medium. The computer readable medium, such as a magnetic stripe or a memory of a chip or a chipset, may include a volatile, a non-volatile, a read only, or a programmable memory that stores data, such as an account identifier, a consumer identifier, and/or an expiration date. The computer readable medium may including executable instructions that, when executed by a computer, the computer will perform a method. For example, the computer readable memory may include information such as the account number or an account holder (a) 508's name.

Examples of the PCD with memory and executable instructions include: a smart card, a personal digital assistant, a digital audio player, a cellular telephone, a personal computer, or a combination thereof. To illustrate, the PCD may be a financial card that can be used by a consumer to conduct a contactless transaction with a merchant, where the financial card includes a microprocessor, a programmable memory, and a transponder (e.g., transmitter or receiver). The financial card can have near field communication capabilities, such as by one or more radio frequency communications such as are used in a "Blue Tooth" communication wireless protocol for exchanging data over short distances from fixed and mobile devices, thereby creating personal area networks.

Merchant (m) 510 may utilize at least one POI terminal (e.g., Point of Service or browser enabled consumer cellular telephone); that can communicate with the account user (au) 508, the acquirer (a) 506, the transaction handler (th) 502, or the issuer (i) 504. A Point of Interaction (POI) can be a physical or virtual communication vehicle that provides the opportunity, through any channel to engage with the consumer for the purposes of providing content, messaging or other communication, related directly or indirectly to the facilitation or execution of a transaction between the merchant (m) 510 and the consumer. Examples of the POI include: a physical or virtual Point of Service (POS) terminal, the PCD of the consumer, a portable digital assistant, a cellular telephone, paper mail, e-mail, an Internet website rendered via a browser executing on computing device, or a combination of the forgoing. Thus, the POI terminal is in operative communication with the transaction processing system 500.

The PCD may interface with the POI using a mechanism including any suitable electrical, magnetic, or optical interfacing system such as a contactless system using radio frequency, a magnetic field recognition system, or a contact system such as a magnetic stripe reader. To illustrate, the POI may have a magnetic stripe reader that makes contact with the magnetic stripe of a healthcare card (e.g., Flexible Savings Account card) of the consumer. As such, data encoded in the magnetic stripe on the healthcare card of consumer read and passed to the POI at merchant (m) 510. These data can include an account identifier of a healthcare account. In another example, the POI may be the PCD of the consumer, such as the cellular telephone of the consumer, where the merchant (m) 510, or an agent thereof, receives the account identifier of the consumer via a webpage of an interactive website rendered by a browser executing on a World Wide Web (Web) enabled PCD.

Typically, a transaction begins with account user (au) 508 presenting the portable consumer device to the merchant (m) 510 to initiate an exchange for resources (e.g., a good or service). The portable consumer device may be associated with an account (e.g., a credit account) of account holder (a) 508 that was issued to the account holder (a) 508 by issuer (i) 504.

Merchant (m) 510 may use the POI terminal to obtain account information, such as a number of the account of the account holder (a) 508, from the portable consumer device. The portable consumer device may interface with the POI terminal using a mechanism including any suitable electrical, magnetic, or optical interfacing system such as a contactless system using radio frequency or magnetic field recognition system or contact system such as a magnetic stripe reader. The POI terminal sends a transaction authorization request to the issuer (i) 504 of the account associated with the PCD. Alternatively, or in combination, the PCD may communicate with issuer (i) 504, transaction handler (th) 502, or acquirer (a) 506.

Issuer (i) 504 may authorize the transaction and forward same to the transaction handler (th) 502. Transaction handler (th) 502 may also clear the transaction. Authorization includes issuer (i) 504, or transaction handler (th) 502 on behalf of issuer (i) 504, authorizing the transaction in connection with issuer (i) 504's instructions such as through the use of business rules. The business rules could include instructions or guidelines from the transaction handler (th) 502, the account holder (a) 508, the merchant (m) 510, the acquirer (a) 506, the issuer (i) 504, a related financial institution, or combinations thereof. The transaction handler (th) 502 may, but need not, maintain a log or history of authorized transactions. Once approved, the merchant (m) 510 may record the authorization, allowing the account user (au) 508 to receive the good or service from merchant (m) or an agent thereof.

The merchant (m) 510 may, at discrete periods, such as the end of the day, submit a list of authorized transactions to the acquirer (a) 506 or other transaction related data for processing through the transaction processing system 500. The transaction handler (th) 502 may optionally compare the submitted authorized transaction list with its own log of authorized transactions. The transaction handler (th) 502 may route authorization transaction amount requests from the corresponding the acquirer (a) 506 to the corresponding issuer (i) 504 involved in each transaction. Once the acquirer (a) 506 receives the payment of the authorized transaction from the issuer (i) 504, the acquirer (a) 506 can forward the payment to the merchant (m) 510 less any transaction costs, such as fees for the processing of the transaction. If the transaction involves a debit or pre-paid card, the acquirer (a) 506 may choose not to wait for the issuer (i) 504 to forward the payment prior to paying merchant (m) 510.

There may be intermittent steps in the foregoing process, some of which may occur simultaneously. For example, the acquirer (a) 506 can initiate the clearing and settling process, which can result in payment to the acquirer (a) 506 for the amount of the transaction. The acquirer (a) 506 may request from the transaction handler (th) 502 that the transaction be cleared and settled. Clearing includes the exchange of financial information between the issuer (i) 504 and the acquirer (a) 506 and settlement includes the exchange of funds. The transaction handler (th) 502 can provide services in connection with settlement of the transaction. The settlement of a transaction includes depositing an amount of the transaction settlement from a settlement house, such as a settlement bank, which transaction handler (th) 502 typically chooses, into a clearinghouse bank, such as a clearing bank, that acquirer (a) 506 typically chooses. The issuer (i) 504 deposits the same from a clearinghouse bank, such as a clearing bank, which the issuer (i) 504 typically chooses, into the settlement house. Thus, a typical transaction involves various entities to request, authorize, and fulfill processing the transaction.

The transaction processing system 500 will preferably have network components suitable for scaling the number and data payload size of transactions that can be authorized, cleared and settled in both real time and batch processing. These include hardware, software, data elements, and storage network devices for the same. Examples of transaction processing system 500 include those operated, at least in part, by:

American Express Travel Related Services Company, Inc; MasterCard International, Inc.; Discover Financial Services, Inc.; First Data Corporation; Diners Club International, LTD; Visa Inc.; and agents of the foregoing.

Each of the network/switch (ns) 502 can include one or more data centers for processing transactions, where each transaction can include up to 100 kilobytes of data or more. The data corresponding to the transaction can include information about the types and quantities of goods and services in the transaction, information about the account holder (a) 508, the account user (au) 508, the merchant (m) 510, tax and incentive treatment(s) of the goods and services, coupons, rebates, rewards, loyalty, discounts, returns, exchanges, cashback transactions, etc.

By way of example, network/switch (ns) 502 can include one or more mainframe computers (e.g., one or more IBM mainframe computers) for one or more server farms (e.g., one or more Sun UNIX Super servers), where the mainframe computers and server farms can be in diverse geographic locations.

Each issuer (i) 504 (or agent issuer (ai) 504 thereof) and each acquirer (a) 506 (or agent acquirer (aq) 506 thereof) can use or more router/switch (e.g., Cisco™ routers/switches) to communicate with each network/switch (ns) 502 via dedicated communication systems.

Transaction handler (th) 502 can store information about transactions processed through transaction processing system 500 in data warehouses such as may be incorporated as part of the plurality of networks/switches 502. This information can be data mined. The data mining transaction research and modeling can be used for advertising, account holder and merchant loyalty incentives and rewards, fraud detection and prediction, and to develop tools to demonstrate savings and efficiencies made possible by use of the transaction processing system 500 over paying and being paid by cash, or other traditional payment mechanisms.

The VisaNet® system is an example component of the transaction handler (th) 502 in the transaction processing system 500. Presently, the VisaNet® system is operated in part by Visa Inc. As of 2006, the VisaNet® system Inc. was processing around 300 million transaction daily, on over 1 billion accounts used in over 170 countries. Financial instructions numbering over 16,000 connected through the VisaNet® system to around 20 million merchants (m) 510. In 2007, around 71 billion transactions for about 4 trillion U.S. dollars were cleared and settled through the VisaNet® system, some of which involved a communication length of around 24,000 miles in around two (2) seconds.

The following example is presented to further illustrate to persons skilled in the art how to make and use the invention. This example is not intended as a limitation, however, upon the scope of the invention, which is defined only by the appended claims.

EXAMPLE

By way of example and not limitation, a doctor may diagnose a patient as needing a medication, manufactured and distributed by a given pharmaceutical company, and decide to provide a sample using a sample transaction payment card according to the present discussion. Through use of a card processor system, the doctor can determine whether he or she has available samples of the medications to distribute and, if so, can request that a sample transaction payment card be activated and associated with an electronic voucher for a sample of the medication. The request may include a specific number of samples for distribution and a coupon for an OTC item. The request, for example, may be received by an sponsor account issuer and/or a transaction handler who will facilitate the activation of the sample transaction payment card and association of account identifier with the sample drug and/or medical supply information. Here, the account holder of the sponsor account might be a pharmaceutical company who wishes to promote the use of the drug by giving out free samples to patients via their prescribing physicians.

The prescribing doctor, or agent thereof, may additionally use the card processor system to store information relating to the sample medications, the prescribing doctor him or herself, the patient, prescriptions, dosing instructions, and any other information on the sample transaction payment card. These data could be stored via a magnetic stripe, imbedded microchip, or other memory storage device.

Once done, the patient then presents the sample transaction payment card to a pharmacy to redeem the samples. The pharmacy may require the patient to show identification, such as a driver's license, to compare with information printed or stored on the sample transaction payment card. The pharmacy then sends an authorization request for permission to dispense the medication and to charge the pharmaceutical company's account. The authorization request is, for example, received by the pharmacy's acquirer who forwards it for processing by a transaction handler.

The transaction handler may then send an authorization response authorizing the distribution of the samples after matching the account identifier of the sample transaction payment card activated by the doctor with the account identifier of the card presented to the pharmacy. Upon receiving the authorization response, the pharmacy may then distribute the approved quantity of the medication to the patient. If the sample transaction payment card is a one-time use card, the transaction handler may additionally deactivate it. The transaction handler may also send a request to the issuer of the sample transaction payment card to debit the pharmaceutical company's account for the cost of the samples and forward that payment to the acquirer for deposit in the pharmacy's account. Furthermore, the transaction handler may send a request to the issuer of the portable consumer transaction payment device to debit the patient's account for the cost of the item purchased and forward that payment to the acquirer for deposit in the pharmacy's account.

The steps, methods, processes, and devices described in connection with the implementations disclosed herein, are made with reference to the Figures, in which like numerals represent the same or similar elements. While described in terms of the best mode, it will be appreciated by those skilled in the art that the description is intended to cover alternatives, modifications, and equivalents as may be included within the spirit and scope of the invention as defined by the appended claims and their equivalents as supported by the following disclosure and drawings. Reference throughout this specification to "one implementation," "an implementation," or similar language means that a particular feature, structure, or characteristic described in connection with the implementation is included in at least one implementation of the present invention. Thus, appearances of the phrases "in one implementation," "in an implementation," and similar language throughout this specification may, but do not necessarily, all refer to the same implementation.

The described features, structures, or characteristics of the invention may be combined in any suitable manner in one or more implementations. In the following description, numerous specific details are recited to provide a thorough understanding of implementations of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow charts included are generally set forth as logical flow chart diagrams. As such, the depicted order and labeled steps are indicative of one implementation of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention may be embodied in other specific forms without departing from its spirit or essential characteristics. The described implementations are to be considered in all respects only as illustrative and not restrictive. The scope of the invention is, therefore, indicated by the appended claims rather than by the foregoing description. All changes which come within the meaning and range of equivalency of the claims are to be embraced within their scope.

PPD Controller

FIG. 6 shows a block diagram illustrating embodiments of a PPD controller 601. In this embodiment, the PPD controller 601 may serve to aggregate, process, store, search, serve, identify, instruct, generate, match, and/or facilitate interactions with a computer through various technologies, and/or other related data.

Typically, users, e.g., 633a, which may be people and/or other systems, may engage information technology systems (e.g., computers) to facilitate information processing. In turn, computers employ processors to process information; such processors 603 may be referred to as central processing units (CPU). One form of processor is referred to as a microprocessor. CPUs use communicative circuits to pass binary encoded signals acting as instructions to enable various operations. These instructions may be operational and/or data instructions containing and/or referencing other instructions and data in various processor accessible and operable areas of memory 629 (e.g., registers, cache memory, random access memory, etc.). Such communicative instructions may be stored and/or transmitted in batches (e.g., batches of instructions) as programs and/or data components to facilitate desired operations. These stored instruction codes, e.g., programs, may engage the CPU circuit components and other motherboard and/or system components to perform desired operations. One type of program is a computer operating system, which, may be executed by CPU on a computer; the operating system enables and facilitates users to access and operate computer information technology and resources. Some resources that may be employed in information technology systems include: input and output mechanisms through which data may pass into and out of a computer; memory storage into which data may be saved; and processors by which information may be processed. These information technology systems may be used to collect data for later retrieval, analysis, and manipulation, which may be facilitated through a database program. These information technology systems provide interfaces that allow users to access and operate various system components.

In one embodiment, the PPD controller 601 may be connected to and/or communicate with entities such as, but not limited to: one or more users from user input devices 611; peripheral devices 612; an optional cryptographic processor device 628; and/or a communications network 613. For example, the PPD controller 601 may be connected to and/or communicate with users, e.g., 633a, operating client device(s), e.g., 633b, including, but not limited to, personal computer(s), server(s) and/or various mobile device(s) including, but not limited to, cellular telephone(s), smartphone(s) (e.g., iPhone®, Blackberry®, Android OS-based phones etc.), tablet computer(s) (e.g., Apple iPad™, HP Slate™, Motorola Xoom™, etc.), eBook reader(s) (e.g., Amazon Kindle™, Barnes and Noble's Nook™ eReader, etc.), laptop computer(s), notebook(s), netbook(s), gaming console(s) (e.g., XBOX Live™, Nintendo® DS, Sony PlayStation® Portable, etc.), portable scanner(s), and/or the like.

Networks are commonly thought to comprise the interconnection and interoperation of clients, servers, and intermediary nodes in a graph topology. It should be noted that the term "server" as used throughout this application refers generally to a computer, other device, program, or combination thereof that processes and responds to the requests of remote users across a communications network. Servers serve their information to requesting "clients." The term "client" as used herein refers generally to a computer, program, other device, user and/or combination thereof that is capable of processing and making requests and obtaining and processing any responses from servers across a communications network. A computer, other device, program, or combination thereof that facilitates, processes information and requests, and/or furthers the passage of information from a source user to a destination user is commonly referred to as a "node." Networks are generally thought to facilitate the transfer of information from source points to destinations. A node specifically tasked with furthering the passage of information from a source to a destination is commonly called a "router." There are many forms of networks such as Local Area Networks (LANs), Pico networks, Wide Area Networks (WANs), Wireless Networks (WLANs), etc. For example, the Internet is generally accepted as being an interconnection of a multitude of networks whereby remote clients and servers may access and interoperate with one another.

The PPD controller 601 may be based on computer systems that may comprise, but are not limited to, components such as: a computer systemization 602 connected to memory 629.

Computer Systemization

A computer systemization 602 may comprise a clock 630, central processing unit ("CPU(s)" and/or "processor(s)" (these terms are used interchangeable throughout the disclosure unless noted to the contrary)) 603, a memory 629 (e.g., a read only memory (ROM) 606, a random access memory (RAM) 605, etc.), and/or an interface bus 607, and most frequently, although not necessarily, are all interconnected and/or communicating through a system bus 604 on one or more (mother)board(s) 602 having conductive and/or otherwise transportive circuit pathways through which instructions (e.g., binary encoded signals) may travel to effectuate communications, operations, storage, etc. The computer systemization may be connected to a power source 686; e.g., optionally the power source may be internal. Optionally, a cryptographic processor 626 and/or transceivers (e.g., ICs) 674 may be connected to the system bus. In another embodiment, the cryptographic processor and/or transceivers may be connected as either internal and/or external peripheral devices 612 via the interface bus I/O. In turn, the transceivers may be connected to antenna(s) 675, thereby effectuating wireless transmission and reception of various communication and/or sensor protocols; for example the antenna(s) may connect to: a Texas Instruments WiLink WL1283 transceiver chip (e.g., providing 802.11n, Bluetooth 3.0, FM, global positioning system (GPS) (thereby allowing PPD controller to determine its location)); Broadcom BCM4329FKUBG transceiver chip (e.g., providing 802.11n, Bluetooth 2.1+EDR, FM, etc.); a Broadcom BCM4750IUB8 receiver chip (e.g., GPS); an Infineon Technologies X-Gold 68-PMB9800 (e.g., providing 2G/3G HSDPA/HSUPA communications); and/or the like. The system clock typically has a crystal oscillator and generates a base signal through the computer systemization's circuit pathways. The clock is typically coupled to the system bus and various clock multipliers that will increase or decrease the base operating frequency for other components interconnected in the computer systemization. The clock and various components in a computer systemization drive signals embodying information throughout the system. Such transmission and reception of instructions embodying information throughout a computer systemization may be commonly referred to as communications. These communicative instructions may further be transmitted, received, and the cause of return and/or reply communications beyond the instant computer systemization to: communications networks, input devices, other computer systemizations, peripheral devices, and/or the like. It should be understood that in alternative embodiments, any of the above components may be connected directly to one another, connected to the CPU, and/or organized in numerous variations employed as exemplified by various computer systems.

The CPU comprises at least one high-speed data processor adequate to execute program components for executing user and/or system-generated requests. Often, the processors themselves will incorporate various specialized processing units, such as, but not limited to: integrated system (bus) controllers, memory management control units, floating point units, and even specialized processing sub-units like graphics processing units, digital signal processing units, and/or the like. Additionally, processors may include internal fast access addressable memory, and be capable of mapping and addressing memory 629 beyond the processor itself; internal memory may include, but is not limited to: fast registers, various levels of cache memory (e.g., level 1, 2, 3, etc.), RAM, etc. The processor may access this memory through the use of a memory address space that is accessible via instruction address, which the processor can construct and decode allowing it to access a circuit path to a specific memory address space having a memory state. The CPU may be a microprocessor such as: AMD's Athlon, Duron and/or Opteron; ARM's application, embedded and secure processors; IBM and/or Motorola's DragonBall and PowerPC; IBM's and Sony's Cell processor; Intel's Celeron, Core (2) Duo, Itanium, Pentium, Xeon, and/or XScale; and/or the like processor(s). The CPU interacts with memory through instruction passing through conductive and/or transportive conduits (e.g., (printed) electronic and/or optic circuits) to execute stored instructions (i.e., program code) according to conventional data processing techniques. Such instruction passing facilitates communication within the PPD controller and beyond through various interfaces. Should processing requirements dictate a greater amount speed and/or capacity, distributed processors (e.g., Distributed PPD), mainframe, multi-core, parallel, and/or super-computer architectures may similarly be employed. Alternatively, should deployment requirements dictate greater portability, smaller Personal Digital Assistants (PDAs) may be employed.

Depending on the particular implementation, features of the PPD may be achieved by implementing a microcontroller such as CAST's R8051XC2 microcontroller; Intel's MCS 51 (i.e., 8051 microcontroller); and/or the like. Also, to implement certain features of the PPD, some feature implementations may rely on embedded components, such as: Application-Specific Integrated Circuit ("ASIC"), Digital Signal Processing ("DSP"), Field Programmable Gate Array ("FPGA"), and/or the like embedded technology. For example, any of the PPD component collection (distributed or otherwise) and/or features may be implemented via the microprocessor and/or via embedded components; e.g., via ASIC, coprocessor, DSP, FPGA, and/or the like. Alternately, some implementations of the PPD may be implemented with embedded components that are configured and used to achieve a variety of features or signal processing.

Depending on the particular implementation, the embedded components may include software solutions, hardware solutions, and/or some combination of both hardware/software solutions. For example, PPD features discussed herein may be achieved through implementing FPGAs, which are a semiconductor devices containing programmable logic components called "logic blocks", and programmable interconnects, such as the high performance FPGA Virtex series and/or the low cost Spartan series manufactured by Xilinx. Logic blocks and interconnects can be programmed by the customer or designer, after the FPGA is manufactured, to implement any of the PPD features. A hierarchy of programmable interconnects allow logic blocks to be interconnected as needed by the PPD system designer/administrator, somewhat like a one-chip programmable breadboard. An FPGA's logic blocks can be programmed to perform the operation of basic logic gates such as AND, and XOR, or more complex combinational operators such as decoders or simple mathematical operations. In most FPGAs, the logic blocks also include memory elements, which may be circuit flip-flops or more complete blocks of memory. In some circumstances, the PPD may be developed on regular FPGAs and then migrated into a fixed version that more resembles ASIC implementations. Alternate or coordinating implementations may migrate PPD controller features to a final ASIC instead of or in addition to FPGAs. Depending on the implementation all of the aforementioned embedded components and microprocessors may be considered the "CPU" and/or "processor" for the PPD.

Power Source

The power source 686 may be of any standard form for powering small electronic circuit board devices such as the following power cells: alkaline, lithium hydride, lithium ion, lithium polymer, nickel cadmium, solar cells, and/or the like. Other types of AC or DC power sources may be used as well. In the case of solar cells, in one embodiment, the case provides an aperture through which the solar cell may capture photonic energy. The power cell 686 is connected to at least one of the interconnected subsequent components of the PPD thereby providing an electric current to all subsequent components. In one example, the power source 686 is connected to the system bus component 604. In an alternative embodiment, an outside power source 686 is provided through a connection across the I/O 608 interface. For example, a USB and/or IEEE 1394 connection carries both data and power across the connection and is therefore a suitable source of power.

Interface Adapters

Interface bus(ses) 607 may accept, connect, and/or communicate to a number of interface adapters, conventionally although not necessarily in the form of adapter cards, such as but not limited to: input output interfaces (I/O) 608, storage interfaces 609, network interfaces 610, and/or the like. Optionally, cryptographic processor interfaces 627 similarly may be connected to the interface bus. The interface bus provides for the communications of interface adapters with one another as well as with other components of the computer systemization. Interface adapters are adapted for a compatible interface bus. Interface adapters conventionally connect to the interface bus via a slot architecture. Conventional slot architectures may be employed, such as, but not limited to: Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and/or the like.

Storage interfaces 609 may accept, communicate, and/or connect to a number of storage devices such as, but not limited to: storage devices 614, removable disc devices, and/or the like. Storage interfaces may employ connection protocols such as, but not limited to: (Ultra) (Serial) Advanced Technology Attachment (Packet Interface) ((Ultra) (Serial) ATA(PI)), (Enhanced) Integrated Drive Electronics ((E)IDE), Institute of Electrical and Electronics Engineers (IEEE) 1394, fiber channel, Small Computer Systems Interface (SCSI), Universal Serial Bus (USB), and/or the like.

Network interfaces 610 may accept, communicate, and/or connect to a communications network 613. Through a communications network 613, the PPD controller is accessible through remote clients 633b (e.g., computers with web browsers) by users 633a. Network interfaces may employ connection protocols such as, but not limited to: direct connect, Ethernet (thick, thin, twisted pair 10/100/1000 Base T, and/or the like), Token Ring, wireless connection such as IEEE 802.11a-x, and/or the like. Should processing requirements dictate a greater amount speed and/or capacity, distributed network controllers (e.g., Distributed PPD), architectures may similarly be employed to pool, load balance, and/or otherwise increase the communicative bandwidth required by the PPD controller. A communications network may be any one and/or the combination of the following: a direct interconnection; the Internet; a Local Area Network (LAN); a Metropolitan Area Network (MAN); an Operating Missions as Nodes on the Internet (OMNI); a secured custom connection; a Wide Area Network (WAN); a wireless network (e.g., employing protocols such as, but not limited to a Wireless Application Protocol (WAP), I-mode, and/or the like); and/or the like. A network interface may be regarded as a specialized form of an input output interface. Further, multiple network interfaces 610 may be used to engage with various communications network types 613. For example, multiple network interfaces may be employed to allow for the communication over broadcast, multicast, and/or unicast networks.

Input Output interfaces (I/O) 608 may accept, communicate, and/or connect to user input devices 611, peripheral devices 612, cryptographic processor devices 628, and/or the like. I/O may employ connection protocols such as, but not limited to: audio: analog, digital, monaural, RCA, stereo, and/or the like; data: Apple Desktop Bus (ADB), IEEE 1394a-b, serial, universal serial bus (USB); infrared; joystick; keyboard; midi; optical; PC AT; PS/2; parallel; radio; video interface: Apple Desktop Connector (ADC), BNC, coaxial, component, composite, digital, Digital Visual Interface (DVI), high-definition multimedia interface (HDMI), RCA, RF antennae, S-Video, VGA, and/or the like; wireless transceivers: 802.11a/b/g/n/x; Bluetooth; cellular (e.g., code division multiple access (CDMA), high speed packet access (HSPA(+)), high-speed downlink packet access (HSDPA), global system for mobile communications (GSM), long term evolution (LTE), WiMax, etc.); and/or the like. One typical output device may include a video display, which typically comprises a Cathode Ray Tube (CRT) or Liquid Crystal Display (LCD) based monitor with an interface (e.g., DVI circuitry and cable) that accepts signals from a video interface, may be used. The video interface composites information generated by a computer systemization and generates video signals based on the composited information in a video memory frame. Another output device is a television set, which accepts signals from a video interface. Typically, the video interface provides the composited video information through a video connection interface that accepts a video display interface (e.g., an RCA composite video connector accepting an RCA composite video cable; a DVI connector accepting a DVI display cable, etc.).

User input devices 611 often are a type of peripheral device 612 (see below) and may include: card readers, dongles, finger print readers, gloves, graphics tablets, joysticks, keyboards, microphones, mouse (mice), remote controls, retina readers, touch screens (e.g., capacitive, resistive, etc.), trackballs, trackpads, sensors (e.g., accelerometers, ambient light, GPS, gyroscopes, proximity, etc.), styluses, and/or the like.

Peripheral devices 612 may be connected and/or communicate to I/O and/or other facilities of the like such as network interfaces, storage interfaces, directly to the interface bus, system bus, the CPU, and/or the like. Peripheral devices may be external, internal and/or part of the PPD controller. Peripheral devices may include: antenna, audio devices (e.g., line-in, line-out, microphone input, speakers, etc.), cameras (e.g., still, video, webcam, etc.), dongles (e.g., for copy protection, ensuring secure transactions with a digital signature, and/or the like), external processors (for added capabilities; e.g., crypto devices 628), force-feedback devices (e.g., vibrating motors), network interfaces, printers, scanners, storage devices, transceivers (e.g., cellular, GPS, etc.), video devices (e.g., goggles, monitors, etc.), video sources, visors, and/or the like. Peripheral devices often include types of input devices (e.g., cameras).

It should be noted that although user input devices and peripheral devices may be employed, the PPD controller may be embodied as an embedded, dedicated, and/or monitor-less (i.e., headless) device, wherein access would be provided over a network interface connection.

Cryptographic units such as, but not limited to, microcontrollers, processors 626, interfaces 627, and/or devices 628 may be attached, and/or communicate with the PPD controller. A MC68HC16 microcontroller, manufactured by Motorola Inc., may be used for and/or within cryptographic units. The MC68HC16 microcontroller utilizes a 16-bit multiply-and-accumulate instruction in the 16 MHz configuration and requires less than one second to perform a 512-bit RSA private key operation. Cryptographic units support the authentication of communications from interacting agents, as well as allowing for anonymous transactions. Cryptographic units may also be configured as part of the CPU. Equivalent microcontrollers and/or processors may also be used. Other commercially available specialized cryptographic processors include: the Broadcom's CryptoNetX and other Security Processors; nCipher's nShield, SafeNet's Luna PCI (e.g., 7100) series; Semaphore Communications' 40 MHz Roadrunner 184; Sun's Cryptographic Accelerators (e.g., Accelerator 6000 PCIe Board, Accelerator 500 Daughtercard); Via Nano Processor (e.g., L2100, L2200, U2400) line, which is capable of performing 500+MB/s of cryptographic instructions; VLSI Technology's 33 MHz 6868; and/or the like.

Memory

Generally, any mechanization and/or embodiment allowing a processor to affect the storage and/or retrieval of information is regarded as memory 629. However, memory is a fungible technology and resource, thus, any number of memory embodiments may be employed in lieu of or in concert with one another. It is to be understood that the PPD controller and/or a computer systemization may employ various forms of memory 629. For example, a computer systemization may be configured wherein the operation of on-chip CPU memory (e.g., registers), RAM, ROM, and any other storage devices are provided by a paper punch tape or paper punch card mechanism; however, such an embodiment would result in an extremely slow rate of operation. In a typical configuration, memory 629 will include ROM 606, RAM 605, and a storage device 614. A storage device 614 may be any conventional computer system storage. Storage devices may include a drum; a (fixed and/or removable) magnetic disk drive; a magneto-optical drive; an optical drive (i.e., Blueray, CD ROM/RAM/Recordable (R)/ReWritable (RW), DVD R/RW, HD DVD R/RW etc.); an array of devices (e.g., Redundant Array of Independent Disks (RAID)); solid state memory devices (USB memory, solid state drives (SSD), etc.); other processor-readable storage mediums; and/or other devices of the like. Thus, a computer systemization generally requires and makes use of memory.

Component Collection

The memory 629 may contain a collection of program and/or database components and/or data such as, but not limited to: operating system component(s) 615 (operating system); information server component(s) 616 (information server); user interface component(s) 617 (user interface); Web browser component(s) 618 (Web browser); database(s) 619; mail server component(s) 621; mail client component(s) 622; cryptographic server component(s) 620 (cryptographic server); the PPD component(s) 635; and/or the like (i.e., collectively a component collection). These components may be stored and accessed from the storage devices and/or from storage devices accessible through an interface bus. Although non-conventional program components such as those in the component collection, typically, are stored in a local storage device 614, they may also be loaded and/or stored in memory such as: peripheral devices, RAM, remote storage facilities through a communications network, ROM, various forms of memory, and/or the like.

Operating System

The operating system component 615 is an executable program component facilitating the operation of the PPD controller. Typically, the operating system facilitates access of I/O, network interfaces, peripheral devices, storage devices, and/or the like. The operating system may be a highly fault tolerant, scalable, and secure system such as: Apple Macintosh OS X (Server); AT&T Nan 9; Be OS; Unix and Unix-like system distributions (such as AT&T's UNIX; Berkley Software Distribution (BSD) variations such as FreeBSD, NetBSD, OpenBSD, and/or the like; Linux distributions such as Red Hat, Ubuntu, and/or the like); and/or the like operating systems. However, more limited and/or less secure operating systems also may be employed such as Apple Macintosh OS, IBM OS/2, Microsoft DOS, Microsoft Windows 2000/2003/3.1/95/98/CE/Millenium/NT/Vista/XP (Server), Palm OS, and/or the like. An operating system may communicate to and/or with other components in a component collection, including itself, and/or the like. Most frequently, the operating system communicates with other program components, user interfaces, and/or the like. For example, the operating system may contain, communicate, generate, obtain, and/or provide program component, system, user, and/or data communications, requests, and/or responses. The operating system, once executed by the CPU, may enable the interaction with communications networks, data, I/O, peripheral devices, program components, memory, user input devices, and/or the like. The operating system may provide communications protocols that allow the PPD controller to communicate with other entities through a communications network 613. Various communication protocols may be used by the PPD controller as a subcarrier transport mechanism for interaction, such as, but not limited to: multicast, TCP/IP, UDP, unicast, and/or the like.

Information Server

An information server component 616 is a stored program component that is executed by a CPU. The information server may be a conventional Internet information server such as, but not limited to Apache Software Foundation's Apache, Microsoft's Internet Information Server, and/or the like. The information server may allow for the execution of program components through facilities such as Active Server Page (ASP), ActiveX, (ANSI) (Objective-) C (++), C# and/or .NET, Common Gateway Interface (CGI) scripts, dynamic (D) hypertext markup language (HTML), FLASH, Java, JavaScript, Practical Extraction Report Language (PERL), Hypertext Pre-Processor (PHP), pipes, Python, wireless application protocol (WAP), WebObjects, and/or the like. The information server may support secure communications protocols such as, but not limited to, File Transfer Protocol (FTP); HyperText Transfer Protocol (HTTP); Secure Hypertext Transfer Protocol (HTTPS), Secure Socket Layer (SSL), messaging protocols (e.g., America Online (AOL) Instant Messenger (AIM), Application Exchange (APEX), ICQ, Internet Relay Chat (IRC), Microsoft Network (MSN) Messenger Service, Presence and Instant Messaging Protocol (PRIM), Internet Engineering Task Force's (IETF's) Session Initiation Protocol (SIP), SIP for Instant Messaging and Presence Leveraging Extensions (SIMPLE), open XML-based Extensible Messaging and Presence Protocol (XMPP) (i.e., Jabber or Open Mobile Alliance's (OMA's) Instant Messaging and Presence Service (IMPS)), Yahoo! Instant Messenger Service, and/or the like. The information server provides results in the form of Web pages to Web browsers, and allows for the manipulated generation of the Web pages through interaction with other program components. After a Domain Name System (DNS) resolution portion of an HTTP request is resolved to a particular information server, the information server resolves requests for information at specified locations on the PPD controller based on the remainder of the HTTP request. For example, a request such as http://

123.124.125.126/myInformation.html might have the IP portion of the request "123.124.125.126" resolved by a DNS server to an information server at that IP address; that information server might in turn further parse the http request for the "/myInformation.html" portion of the request and resolve it to a location in memory containing the information "myInformation.html." Additionally, other information serving protocols may be employed across various ports, e.g., FTP communications across port 21, and/or the like. An information server may communicate to and/or with other components in a component collection, including itself, and/or facilities of the like. Most frequently, the information server communicates with the PPD database 619, operating systems, other program components, user interfaces, Web browsers, and/or the like.

Access to the PPD database may be achieved through a number of database bridge mechanisms such as through scripting languages as enumerated below (e.g., CGI) and through inter-application communication channels as enumerated below (e.g., CORBA, WebObjects, etc.). Any data requests through a Web browser are parsed through the bridge mechanism into appropriate grammars as required by the PPD. In one embodiment, the information server would provide a Web form accessible by a Web browser. Entries made into supplied fields in the Web form are tagged as having been entered into the particular fields, and parsed as such. The entered terms are then passed along with the field tags, which act to instruct the parser to generate queries directed to appropriate tables and/or fields. In one embodiment, the parser may generate queries in standard SQL by instantiating a search string with the proper join/select commands based on the tagged text entries, wherein the resulting command is provided over the bridge mechanism to the PPD as a query. Upon generating query results from the query, the results are passed over the bridge mechanism, and may be parsed for formatting and generation of a new results Web page by the bridge mechanism. Such a new results Web page is then provided to the information server, which may supply it to the requesting Web browser.

Also, an information server may contain, communicate, generate, obtain, and/or provide program component, system, user, and/or data communications, requests, and/or responses.

User Interface

Computer interfaces in some respects are similar to automobile operation interfaces. Automobile operation interface elements such as steering wheels, gearshifts, and speedometers facilitate the access, operation, and display of automobile resources, and status. Computer interaction interface elements such as check boxes, cursors, menus, scrollers, and windows (collectively and commonly referred to as widgets) similarly facilitate the access, capabilities, operation, and display of data and computer hardware and operating system resources, and status. Operation interfaces are commonly called user interfaces. Graphical user interfaces (GUIs) such as the Apple Macintosh Operating System's Aqua, IBM's OS/2, Microsoft's Windows 2000/2003/3.1/95/98/CE/Millenium/NT/XP/Vista/7 (i.e., Aero), Unix's X-Windows (e.g., which may include additional Unix graphic interface libraries and layers such as K Desktop Environment (KDE), mythTV and GNU Network Object Model Environment (GNOME)), web interface libraries (e.g., ActiveX, AJAX, (D)HTML, FLASH, Java, JavaScript, etc. interface libraries such as, but not limited to, Dojo, jQuery(UI), MooTools, Prototype, script.aculo.us, SWFObject, Yahoo! User Interface, any of which may be used and) provide a baseline and means of accessing and displaying information graphically to users.

A user interface component 617 is a stored program component that is executed by a CPU. The user interface may be a conventional graphic user interface as provided by, with, and/or atop operating systems and/or operating environments such as already discussed. The user interface may allow for the display, execution, interaction, manipulation, and/or operation of program components and/or system facilities through textual and/or graphical facilities. The user interface provides a facility through which users may affect, interact, and/or operate a computer system. A user interface may communicate to and/or with other components in a component collection, including itself, and/or facilities of the like. Most frequently, the user interface communicates with operating systems, other program components, and/or the like. The user interface may contain, communicate, generate, obtain, and/or provide program component, system, user, and/or data communications, requests, and/or responses.

Web Browser

A Web browser component 618 is a stored program component that is executed by a CPU. The Web browser may be a conventional hypertext viewing application such as Microsoft Internet Explorer or Netscape Navigator. Secure Web browsing may be supplied with 128 bit (or greater) encryption by way of HTTPS, SSL, and/or the like. Web browsers allowing for the execution of program components through facilities such as ActiveX, AJAX, (D)HTML, FLASH, Java, JavaScript, web browser plug-in APIs (e.g., FireFox, Safari Plug-in, and/or the like APIs), and/or the like. Web browsers and like information access tools may be integrated into PDAs, cellular telephones, and/or other mobile devices. A Web browser may communicate to and/or with other components in a component collection, including itself, and/or facilities of the like. Most frequently, the Web browser communicates with information servers, operating systems, integrated program components (e.g., plug-ins), and/or the like; e.g., it may contain, communicate, generate, obtain, and/or provide program component, system, user, and/or data communications, requests, and/or responses. Also, in place of a Web browser and information server, a combined application may be developed to perform similar operations of both. The combined application would similarly affect the obtaining and the provision of information to users, user agents, and/or the like from the PPD enabled nodes. The combined application may be nugatory on systems employing standard Web browsers.

Mail Server

A mail server component 621 is a stored program component that is executed by a CPU 603. The mail server may be a conventional Internet mail server such as, but not limited to sendmail, Microsoft Exchange, and/or the like. The mail server may allow for the execution of program components through facilities such as ASP, ActiveX, (ANSI) (Objective-) C (++), C# and/or .NET, CGI scripts, Java, JavaScript, PERL, PHP, pipes, Python, WebObjects, and/or the like. The mail server may support communications protocols such as, but not limited to: Internet message access protocol (IMAP), Messaging Application Programming Interface (MAPI)/Microsoft Exchange, post office protocol (POPS), simple mail transfer protocol (SMTP), and/or the like. The mail server can route, forward, and process incoming and outgoing mail messages that have been sent, relayed and/or otherwise traversing through and/or to the PPD.

Access to the PPD mail may be achieved through a number of APIs offered by the individual Web server components and/or the operating system.

Also, a mail server may contain, communicate, generate, obtain, and/or provide program component, system, user, and/or data communications, requests, information, and/or responses.

Mail Client

A mail client component 622 is a stored program component that is executed by a CPU 603. The mail client may be a conventional mail viewing application such as Apple Mail, Microsoft Entourage, Microsoft Outlook, Microsoft Outlook Express, Mozilla, Thunderbird, and/or the like. Mail clients may support a number of transfer protocols, such as: IMAP, Microsoft Exchange, POP3, SMTP, and/or the like. A mail client may communicate to and/or with other components in a component collection, including itself, and/or facilities of the like. Most frequently, the mail client communicates with mail servers, operating systems, other mail clients, and/or the like; e.g., it may contain, communicate, generate, obtain, and/or provide program component, system, user, and/or data communications, requests, information, and/or responses. Generally, the mail client provides a facility to compose and transmit electronic mail messages.

Cryptographic Server

A cryptographic server component 620 is a stored program component that is executed by a CPU 603, cryptographic processor 626, cryptographic processor interface 627, cryptographic processor device 628, and/or the like. Cryptographic processor interfaces will allow for expedition of encryption and/or decryption requests by the cryptographic component; however, the cryptographic component, alternatively, may run on a conventional CPU. The cryptographic component allows for the encryption and/or decryption of provided data. The cryptographic component allows for both symmetric and asymmetric (e.g., Pretty Good Protection (PGP)) encryption and/or decryption. The cryptographic component may employ cryptographic techniques such as, but not limited to: digital certificates (e.g., X.509 authentication framework), digital signatures, dual signatures, enveloping, password access protection, public key management, and/or the like. The cryptographic component will facilitate numerous (encryption and/or decryption) security protocols such as, but not limited to: checksum, Data Encryption Standard (DES), Elliptical Curve Encryption (ECC), International Data Encryption Algorithm (IDEA), Message Digest 5 (MD5, which is a one way hash operation), passwords, Rivest Cipher (RC5), Rijndael, RSA (which is an Internet encryption and authentication system that uses an algorithm developed in 1977 by Ron Rivest, Adi Shamir, and Leonard Adleman), Secure Hash Algorithm (SHA), Secure Socket Layer (SSL), Secure Hypertext Transfer Protocol (HTTPS), and/or the like. Employing such encryption security protocols, the PPD may encrypt all incoming and/or outgoing communications and may serve as node within a virtual private network (VPN) with a wider communications network. The cryptographic component facilitates the process of "security authorization" whereby access to a resource is inhibited by a security protocol wherein the cryptographic component effects authorized access to the secured resource. In addition, the cryptographic component may provide unique identifiers of content, e.g., employing and MD5 hash to obtain a unique signature for an digital audio file. A cryptographic component may communicate to and/or with other components in a component collection, including itself, and/or facilities of the like. The cryptographic component supports encryption schemes allowing for the secure transmission of information across a communications network to enable the PPD component to engage in secure transactions if so desired. The cryptographic component facilitates the secure accessing of resources on the PPD and facilitates the access of secured resources on remote systems; i.e., it may act as a client and/or server of secured resources. Most frequently, the cryptographic component communicates with information servers, operating systems, other program components, and/or the like. The cryptographic component may contain, communicate, generate, obtain, and/or provide program component, system, user, and/or data communications, requests, and/or responses.

The PPD Database

The PPD database component 619 may be embodied in a database and its stored data. The database is a stored program component, which is executed by the CPU; the stored program component portion configuring the CPU to process the stored data. The database may be a conventional, fault tolerant, relational, scalable, secure database such as Oracle or Sybase. Relational databases are an extension of a flat file. Relational databases consist of a series of related tables. The tables are interconnected via a key field. Use of the key field allows the combination of the tables by indexing against the key field; i.e., the key fields act as dimensional pivot points for combining information from various tables. Relationships generally identify links maintained between tables by matching primary keys. Primary keys represent fields that uniquely identify the rows of a table in a relational database. More precisely, they uniquely identify rows of a table on the "one" side of a one-to-many relationship.

Alternatively, the PPD database may be implemented using various standard data-structures, such as an array, hash, (linked) list, struct, structured text file (e.g., XML), table, and/or the like. Such data-structures may be stored in memory and/or in (structured) files. In another alternative, an object-oriented database may be used, such as Frontier, ObjectStore, Poet, Zope, and/or the like. Object databases can include a number of object collections that are grouped and/or linked together by common attributes; they may be related to other object collections by some common attributes. Object-oriented databases perform similarly to relational databases with the exception that objects are not just pieces of data but may have other types of capabilities encapsulated within a given object. If the PPD database is implemented as a data-structure, the use of the PPD database 619 may be integrated into another component such as the PPD component 635. Also, the database may be implemented as a mix of data structures, objects, and relational structures. Databases may be consolidated and/or distributed in countless variations through standard data processing techniques. Portions of databases, e.g., tables, may be exported and/or imported and thus decentralized and/or integrated.

In one embodiment, the database component 619 includes several tables 619a-o. A Users table 619a may include fields such as, but not limited to: user_id, ssn, dob, first_name, last_name, age, state, address_firstline, address_secondline, zipcode, devices_list, contact_info, contact_type, alt_contact_info, alt_contact_type, user_gender, user_clothing_size, user_body_type, user_eye_color, user_hair_color, user_ complexion, user_personalized_gesture_models, user_recommended_items, user_image, user_image_date, user_body_joint_location, and/or the like. The Users table may support and/or track multiple entity accounts on a TVC. A Devices table 619b may include fields such as, but not limited to: device_ID, device_name, device_IP, device_GPS, device_MAC, device_serial, device_ECID, device_UDID, device_browser, device_type, device_model, device_version, device_OS, device_apps_list, device_securekey, wallet_app_installed_flag, and/or the like. An Apps table 619c may include fields such as, but not limited to: app_ID, app_name, app_type, app_dependencies, app_access_code, user_pin, and/or the like. An Accounts table 619d may include fields such as, but not limited to: account_number, account_security_code, account_name, issuer_acquirer_flag, issuer_name, acquirer_name, account_address, routing_number, access_API_call, linked_wallets_list, and/or the like. A Merchants table 619e may include fields such as, but not limited to: merchant_id, merchant_name, merchant_address, store_id, ip_address, mac_address, auth_key, port_num, security_settings_list, and/or the like. An Issuers table 619f may include fields such as, but not limited to: issuer_id, issuer_name, issuer_address, ip_address, mac_address, auth_key, port_num, security_settings_list, and/or the like. An Acquirers table 619g may include fields such as, but not limited to: account_firstname, account_lastname, account_type, account_num, account_balance_list, billingaddress_line1, billingaddress_line2, billing_zipcode, billing_state, shipping_preferences, shippingaddress_line1, shippingaddress_line2, shipping_zipcode, shipping_state, and/or the like. A Pay Gateways table 619h may include fields such as, but not limited to: gateway_ID, gateway_IP, gateway_MAC, gateway_secure_key, gateway_access_list, gateway_API_call_list, gateway_services_list, and/or the like. A Shop Sessions table 619i may include fields such as, but not limited to: user_id, session_id, alerts_URL, timestamp, expiry_lapse, merchant_id, store_id, device_type, device_ID, device_IP, device_MAC, device_browser, device_serial, device_ECID, device_model, device_OS, wallet_app_installed, total_cost, cart_ID_list, product_params_list, social_flag, social_message, social_networks_list, coupon_lists, accounts_list, CVV2_lists, charge_ratio_list, charge_priority_list, value_exchange_symbols_list, bill_address, ship_address, cloak_flag, pay_mode, alerts_rules_list, and/or the like. A Transactions table 619j may include fields such as, but not limited to: order_id, user_id, timestamp, transaction_cost, purchase_details_list, num_products, products_list, product_type, product_params_list, product_title, product_summary, quantity, user_id, client_id, client_ip, client_type, client_model, operating_system, os_version, app_installed_flag, user_id, account_firstname, account_lastname, account_type, account_num, account_priority_account_ratio, billingaddress_line1, billingaddress_line2, billing_zipcode, billing_state, shipping_preferences, shippingaddress_line1, shippingaddress_line2, shipping_zipcode, shipping_state, merchant_id, merchant_name, merchant_auth_key, and/or the like. A Batches table 619k may include fields such as, but not limited to: batch_id, transaction_id_list, timestamp_list, cleared_flag_list, clearance_trigger_settings, and/or the like. A Ledgers table 619l may include fields such as, but not limited to: request_id, timestamp, deposit_amount, batch_id, transaction_id, clear_flag, deposit_account, transaction_summary, payor_name, payor_account, and/or the like. A Products table 619m may include fields such as, but not limited to: product_ID, product_title, product_attributes_list, product_price, tax_info_list, related_products_list, offers_list, discounts_list, rewards_list, merchants_list, merchant_availability_list, product_date_added, product_image, product_qr, product_manufacturer, product_model, product_aisle, product_stack, product_shelf, product_type, and/or the like. An Offers table 619n may include fields such as, but not limited to: offer_ID, offer_title, offer_attributes_list, offer_price, offer_expiry, related_products_list, discounts_list, rewards_list, merchants_list, merchant_availability_list, and/or the like. A Behavior Data table 619o may include fields such as, but not limited to: user_id, timestamp, activity_type, activity_location, activity_attribute_list, activity_attribute_values_list, and/or the like.

In one embodiment, the PPD database may interact with other database systems. For example, employing a distributed database system, queries and data access by search PPD component may treat the combination of the PPD database, an integrated data security layer database as a single database entity.

In one embodiment, user programs may contain various user interface primitives, which may serve to update the PPD. Also, various accounts may require custom database tables depending upon the environments and the types of clients the PPD may need to serve. It should be noted that any unique fields may be designated as a key field throughout. In an alternative embodiment, these tables have been decentralized into their own databases and their respective database controllers (i.e., individual database controllers for each of the above tables). Employing standard data processing techniques, one may further distribute the databases over several computer systemizations and/or storage devices. Similarly, configurations of the decentralized database controllers may be varied by consolidating and/or distributing the various database components 619a-o. The PPD may be configured to keep track of various settings, inputs, and parameters via database controllers.

The PPD database may communicate to and/or with other components in a component collection, including itself, and/or facilities of the like. Most frequently, the PPD database communicates with the PPD component, other program components, and/or the like. The database may contain, retain, and provide information regarding other nodes and data.

The PPDs

The PPD component 635 is a stored program component that is executed by a CPU. In one embodiment, the PPD component incorporates any and/or all combinations of the aspects of the PPD discussed in the previous figures. As such, the PPD affects accessing, obtaining and the provision of information, services, transactions, and/or the like across various communications networks.

The PPD component may transform user triggering inputs (e.g., card swiping 102, touchscreen inputs, etc.) indicating a purchase request via PPD components (e.g., transaction processing 644, account usage verification 643, account management 642, etc.) into purchase transaction triggers and receipt notices (e.g., see 410 in FIG. 4).

The PPD component enabling access of information between nodes may be developed by employing standard development tools and languages such as, but not limited to: Apache components, Assembly, ActiveX, binary executables, (ANSI) (Objective-) C (++), C# and/or .NET, database adapters, CGI scripts, Java, JavaScript, mapping tools, procedural and object oriented development tools, PERL, PHP, Python, shell scripts, SQL commands, web application server extensions, web development environments and libraries (e.g., Microsoft's ActiveX; Adobe AIR, FLEX & FLASH; AJAX; (D)HTML; Dojo, Java; JavaScript; jQuery(UI); MooTools;

Prototype; script.aculo.us; Simple Object Access Protocol (SOAP); SWFObject; Yahoo! User Interface; and/or the like), WebObjects, and/or the like. In one embodiment, the PPD server employs a cryptographic server to encrypt and decrypt communications. The PPD component may communicate to and/or with other components in a component collection, including itself, and/or facilities of the like. Most frequently, the PPD component communicates with the PPD database, operating systems, other program components, and/or the like. The PPD may contain, communicate, generate, obtain, and/or provide program component, system, user, and/or data communications, requests, and/or responses.

Distributed PPDs

The structure and/or operation of any of the PPD node controller components may be combined, consolidated, and/or distributed in any number of ways to facilitate development and/or deployment. Similarly, the component collection may be combined in any number of ways to facilitate deployment and/or development. To accomplish this, one may integrate the components into a common code base or in a facility that can dynamically load the components on demand in an integrated fashion.

The component collection may be consolidated and/or distributed in countless variations through standard data processing and/or development techniques. Multiple instances of any one of the program components in the program component collection may be instantiated on a single node, and/or across numerous nodes to improve performance through load-balancing and/or data-processing techniques. Furthermore, single instances may also be distributed across multiple controllers and/or storage devices; e.g., databases. All program component instances and controllers working in concert may do so through standard data processing communication techniques.

The configuration of the PPD controller will depend on the context of system deployment. Factors such as, but not limited to, the budget, capacity, location, and/or use of the underlying hardware resources may affect deployment requirements and configuration. Regardless of if the configuration results in more consolidated and/or integrated program components, results in a more distributed series of program components, and/or results in some combination between a consolidated and distributed configuration, data may be communicated, obtained, and/or provided. Instances of components consolidated into a common code base from the program component collection may communicate, obtain, and/or provide data. This may be accomplished through intra-application data processing communication techniques such as, but not limited to: data referencing (e.g., pointers), internal messaging, object instance variable communication, shared memory space, variable passing, and/or the like.

If component collection components are discrete, separate, and/or external to one another, then communicating, obtaining, and/or providing data with and/or to other components may be accomplished through inter-application data processing communication techniques such as, but not limited to: Application Program Interfaces (API) information passage; (distributed) Component Object Model ((D)COM), (Distributed) Object Linking and Embedding ((D)OLE), and/or the like), Common Object Request Broker Architecture (CORBA), Jini local and remote application program interfaces, JavaScript Object Notation (JSON), Remote Method Invocation (RMI), SOAP, process pipes, shared files, and/or the like. Messages sent between discrete component components for inter-application communication or within memory spaces of a singular component for intra-application communication may be facilitated through the creation and parsing of a grammar. A grammar may be developed by using development tools such as lex, yacc, XML, and/or the like, which allow for grammar generation and parsing capabilities, which in turn may form the basis of communication messages within and between components.

For example, a grammar may be arranged to recognize the tokens of an HTTP post command, e.g.:

w3c-post http:// . . . Value1 where Value1 is discerned as being a parameter because "http://" is part of the grammar syntax, and what follows is considered part of the post value. Similarly, with such a grammar, a variable "Value1" may be inserted into an "http://" post command and then sent. The grammar syntax itself may be presented as structured data that is interpreted and/or otherwise used to generate the parsing mechanism (e.g., a syntax description text file as processed by lex, yacc, etc.). Also, once the parsing mechanism is generated and/or instantiated, it itself may process and/or parse structured data such as, but not limited to: character (e.g., tab) delineated text, HTML, structured text streams, XML, and/or the like structured data. In another embodiment, inter-application data processing protocols themselves may have integrated and/or readily available parsers (e.g., JSON, SOAP, and/or like parsers) that may be employed to parse (e.g., communications) data. Further, the parsing grammar may be used beyond message parsing, but may also be used to parse: databases, data collections, data stores, structured data, and/or the like. Again, the desired configuration will depend upon the context, environment, and requirements of system deployment.

For example, in some implementations, the PPD controller may be executing a PHP script implementing a Secure Sockets Layer ("SSL") socket server via the information server, which listens to incoming communications on a server port to which a client may send data, e.g., data encoded in JSON format. Upon identifying an incoming communication, the PHP script may read the incoming message from the client device, parse the received JSON-encoded text data to extract information from the JSON-encoded text data into PHP script variables, and store the data (e.g., client identifying information, etc.) and/or extracted information in a relational database accessible using the Structured Query Language ("SQL"). An exemplary listing, written substantially in the form of PHP/SQL commands, to accept JSON-encoded input data from a client device via a SSL connection, parse the data to extract variables, and store the data to a database, is provided below:

```
<?PHP
header('Content-Type: text/plain');
// set ip address and port to listen to for incoming data
$address = '192.168.0.100';
$port = 255;
// create a server-side SSL socket, listen for/accept incoming
communication
$sock = socket_create(AF_INET, SOCK_STREAM, 0);
socket_bind($sock, $address, $port) or die('Could not bind to address');
socket_listen($sock);
$client = socket_accept($sock);
// read input data from client device in 1024 byte blocks until end of
message
do {
    $input = "";
    $input = socket_read($client, 1024);
    $data .= $input;
} while($input != "");
// parse data to extract variables
$obj = json_decode($data, true);
```

```
// store input data in a database
mysql_connect("201.408.185.132",$DBserver,$password); // access
database server
mysql_select("CLIENT_DB.SQL"); // select database to append
mysql_query("INSERT INTO UserTable (transmission)
VALUES ($data)"); // add data to UserTable table in a CLIENT database
mysql_close("CLIENT_DB.SQL"); // close connection to database
?>
```

Also, the following resources may be used to provide example embodiments regarding SOAP parser implementation:

```
http://www.xav.com/perl/site/lib/SOAP/Parser.html
http://publib.boulder.ibm.com/infocenter/tivihelp/v2r1/index.jsp?topic=
  /com.ibm.IBMDI.doc/referenceguide295.htm
``` and other parser implementations:

http://publib.boulder.ibm.com/infocenter/tivihelp/v2r1/index.jsp?topic=/com.ibm .IBMDI.doc/referenceguide259.htm all of which are hereby expressly incorporated by reference herein.

Additional embodiments of the PPD include:

1. A portable prescription sample transaction payment device comprising:
   a substrate having surface with an image rendering thereon that corresponds to a prescription medical supply sample; and
   memory, in contact with the substrate, having data encoded therein including:
     an identifier for the prescription medical supply sample;
     a quantity for the prescription medical supply sample;
     a dosage for the prescription medical supply sample; and
     an identifier for a patient;
   a pharmaceutical company account for a dispensing pharmacist to charge the cost of the prescription medical supply sample for payment to a dispensing pharmacist account to reimburse the dispensing pharmacist for the prescription medical supply sample;
   an image corresponding to the prescription medical supply sample; and
   an identifier for a prescribing medical practitioner prescribing the prescription medical supply sample to the patient.

2. The portable prescription sample transaction payment device as defined in Embodiment 1, wherein:
   the pharmaceutical company account is a type of consumer account issued by an issuer to a pharmaceutical company;
   the portable prescription sample transaction payment device is a type of a portable prescription sample transaction payment device that is associated with a consumer account for a consumer to engage in a plurality of transactions on the consumer account with a plurality of merchants in a payment processing network;
   the payment processing network includes a plurality of merchants and consumers engaging in a plurality of transactions on a plurality of respective consumer accounts that respective issuers issue to the consumers; and
   each said transaction involves the merchant submitting the transaction to an acquirer for processing by a transaction handler who requests the issuer to obtain payment for the transaction from the consumer account, and wherein the issuer forwards the payment to the transaction handler who forwards the payment to the acquirer to reimburse the merchant for the transaction.

3. The portable prescription sample transaction payment device as defined in Embodiment 1, wherein the data encoded in the memory further includes an image of a prescription for the patient from the prescribing medical practitioner.

4. The portable prescription sample transaction payment device as defined in Embodiment 3, wherein the image of the prescription comprises respective images corresponding to:
   the identifier for the patient;
   the identifier for the prescribing medical practitioner of the prescription medical supply sample;
   the identifier for the prescription medical supply sample; and
   the quantity of the prescription medical supply sample.

5. The portable prescription sample transaction payment device as defined in Embodiment 1, wherein the image corresponding to the prescription medical supply sample includes a code identifying the prescription medical supply sample and configured for being scanned by a scanner at a Point of Service terminal.

6. The portable prescription sample transaction payment device as defined in Embodiment 1, wherein the image corresponding to the prescription medical supply sample includes an advertisement selected from the group consisting of:
   an advertisement for the prescription medical supply sample;
   an advertisement not for the prescription medical supply sample;
   an advertisement for the dispensing pharmacist;
   an advertisement for a different product other than the prescription medical supply sample that is also provided by the dispensing pharmacist; and
   a combination of the foregoing.

7. The portable prescription sample transaction payment device as defined in Embodiment 1, wherein the image corresponding to the prescription medical supply sample includes an advertisement selected from the group consisting of:
   an advertisement for a merchant geographically proximal to the prescribing medical practitioner;
   an advertisement for a merchant geographically proximal to the dispensing pharmacist; and
   a combination of the foregoing.

8. The portable prescription sample transaction payment device as defined in Embodiment 1, wherein the memory of the portable prescription sample transaction payment device is selected from the group consisting of:
   a non-volatile memory of a semiconductor device;
   a magnetic encoded data region of a magnetic stripe; and
   a combination of the foregoing.

9. The portable prescription sample transaction payment device as defined in Embodiment 1, wherein the substrate is a portion of a consumer transaction payment card selected from the group consisting of:
   a smart card having a Radio Frequency Identification (RFID) tag, a transponder device and a microchip; and
   a magstripe card; and
   a combination of the foregoing.

10. The portable prescription sample transaction payment device as defined in Embodiment 1, further comprising means for the memory to receive the information by a communication selected from the group consisting of a wireless communication, a hardwired communication, and a magnetic encoded communication for track data received by modifying the magnetism of magnetic particles on a band of magnetic material on the portable prescription sample transaction payment device.

11. The portable prescription sample transaction payment device as defined in Embodiment 1, wherein data in the memory of the portable prescription sample transaction payment device further comprises an identifier, a quantity, and a dosage of a prescription medical supply, other than the prescription medical supply sample, being prescribed by the prescribing medical practitioner to the patient.

12. The portable prescription sample transaction payment device as defined in Embodiment 11, wherein the identifier for the prescription medical supply sample and the identifier for the prescription medical supply, other than the prescription medical supply sample, are both selected from the group consisting of:
a Stock Keeping Unit (SKU);
a Universal Product Code (UPC);
a National Drug Code (NDC);
a trademark;
a commodity type and a trade name of a provider of the commodity type;
an active ingredient of the commodity type and the trade name of the provider of the commodity type; and
a combination of the foregoing.

13. A portable prescription transaction payment device comprising:
memory, embedded in a substrate, having stored therein:
an identifier, quantity, and dosage for each of a plurality of:
a prescription medical supply sample prescribed by a prescribing medical practitioner to a patient; and
a non-sample prescription medical supply each being prescribed by a corresponding said prescribing medical practitioner to the patient;
for each said prescription medical supply sample, a pharmaceutical company account for a dispensing pharmacist to charge the cost of the prescription medical supply sample for payment to a dispensing pharmacist account to reimburse the dispensing pharmacist for the prescription medical supply sample;
an identifier for the patient;
an identifier for each said prescribing medical practitioner;
an identifier for a consumer account issued by an issuer to the patient; and
an identifier to correlate which said prescription for the patient was prescribed by which said prescribing medical practitioner, wherein:
the pharmaceutical company account and the consumer account are each an account in a payment processing network by which a consumer can engage in a plurality of transactions on the account with a plurality of merchants in the payment processing network;
the payment processing network includes a plurality of said merchants and said consumers engaging in the plurality of said transactions on a plurality of respective said accounts that respective said issuers issue to the consumers; and
each said transaction involves the merchant submitting the transaction to an acquirer for processing by a transaction handler who requests the issuer to obtain payment for the transaction from the account, wherein the issuer forwards the payment to the transaction handler who forwards the payment to the acquirer to reimburse the merchant for the transaction;
and
means for providing access to the information in the memory.

14. The portable prescription transaction payment device as defined in Embodiment 13, wherein the consumer account issued by the issuer to the patient is a type selected from the group consisting of a Flexible Savings Account (FSA), a Health Savings Account (HAS), or a Health Reimbursement Account (HRA).

15. The portable prescription transaction payment device as defined in Embodiment 13, wherein the substrate has an image in a surface that the includes representing at least a portion of the information in the memory for being read by the image being scanned by a scanner at a Point of Service terminal.

16. The portable prescription transaction payment device as defined in Embodiment 13, wherein the memory is selected from the group consisting of:
a non-volatile memory of a semiconductor device;
a magnetic encoded data region of a magnetic stripe; and
a combination of the foregoing.

17. The portable prescription transaction payment device as defined in Embodiment 13, wherein the substrate is a portion of a consumer transaction payment card selected from the group consisting of:
a smart card having a Radio Frequency Identification (RFID) tag, a transponder device and a microchip; and
a magstripe card; and
a combination of the foregoing.

18. The portable prescription transaction payment device as defined in Embodiment 13, wherein the information in the memory further includes an image of each said prescription for the patient that was prescribed by the corresponding said prescribing medical practitioner.

19. The portable prescription transaction payment device as defined in Embodiment 18, wherein, for each said image of each said prescription, the prescription in the image is hand written by the prescribing medical practitioner.

20. The portable prescription transaction payment device as defined in Embodiment 18, further comprising means for the memory to receive the information by a communication selected from the group consisting of a wireless communication, a hardwired communication, and a magnetic encoded communication for track data received by modifying the magnetism of magnetic particles on a band of magnetic material on the portable prescription sample transaction payment device.

21. The portable prescription transaction payment device as defined in Embodiment 20, wherein, for each said image of each said prescription, the identifier for the prescribing medical practitioner comprises a handwritten signature of the prescribing medical practitioner.

22. The portable prescription transaction payment device as defined in Embodiment 18, wherein each said image of each said prescription comprises respective images corresponding to:
the identifier for the patient;
the identifier for the prescribing medical practitioner; and
the identifier, quantity, and dosage identifier for the prescription medical supply sample; and
the identifier, quantity, and dosage identifier for the non-sample prescription medical supply.

23. A portable prescription transaction payment device comprising:
   memory, embedded in a substrate, having information stored therein, wherein:
   the substrate has an image on a surface thereof that includes a representation of at least a portion of the information in the memory for being read by the image being scanned by a scanner at a Point of Service terminal:
   the information includes:
   an identifier, quantity, and dosage for each of a plurality of:
   a prescription medical supply sample prescribed by a prescribing medical practitioner to a patient; and
   a non-sample prescription medical supply prescribed by a corresponding said prescribing medical practitioner to the patient;
   an image, having multiple portion, of each said prescription for the patient that was prescribed by the corresponding said prescribing medical practitioner, wherein the portions of the image correspond to:
   the identifier for the patient;
   the identifier for the prescribing medical practitioner; and
   the identifier, quantity, and dosage identifier for the prescription medical supply sample; and
   the identifier, quantity, and dosage identifier for the non-sample prescription medical supply;
   for each said prescription medical supply sample, a pharmaceutical company account for a dispensing pharmacist to charge the cost of the prescription medical supply sample for payment to a dispensing pharmacist account to reimburse the dispensing pharmacist for the prescription medical supply sample; and
   an identifier to correlate which said prescription for the patient was prescribed by which said prescribing medical practitioner, wherein:
      the pharmaceutical company account and the consumer account are each an account in a payment processing network by which a consumer can engage in a plurality of transactions on the account with a plurality of merchants in the payment processing network;
      the payment processing network includes a plurality of said merchants and said consumers engaging in the plurality of said transactions on a plurality of respective said accounts that respective said issuers issue to the consumers; and
      each said transaction involves the merchant submitting the transaction to an acquirer for processing by a transaction handler who requests the issuer to obtain payment for the transaction from the account, wherein the issuer forwards the payment to the transaction handler who forwards the payment to the acquirer to reimburse the merchant for the transaction;
   and
   means for providing access to the information in the memory.
24. The portable prescription transaction payment device as defined in Embodiment 23, wherein the memory is selected from the group consisting of:
   a non-volatile memory of a semiconductor device;
   a magnetic encoded data region of a magnetic stripe; and
   a combination of the foregoing.
25. The portable prescription transaction payment device as defined in Embodiment 23, wherein the substrate is a portion of a consumer transaction payment card selected from the group consisting of:
   a smart card having a Radio Frequency Identification (RFID) tag, a transponder device and a microchip; and
   a magstripe card; and
   a combination of the foregoing.
26. The portable prescription transaction payment device as defined in Embodiment 23, further comprising means for the memory to receive the information by a communication selected from the group consisting of a wireless communication, a hardwired communication, and a magnetic encoded communication for track data received by modifying the magnetism of magnetic particles on a band of magnetic material on the portable prescription sample transaction payment device.
27. The portable prescription transaction payment device as defined in Embodiment 23, wherein, for each said image of each said prescription, the identifier for the prescribing medical practitioner comprises a handwritten signature of the prescribing medical practitioner.
28. The portable prescription transaction payment device as defined in Embodiment 23, wherein, for each said image of each said prescription, the prescription in the image is hand written by the prescribing medical practitioner.

Additional embodiments of the PPD include:
1. A method comprising a plurality of steps each being performed by a computing apparatus executing software, wherein the computing apparatus is enabled for network communications, and wherein the steps include:
   receiving in a transmission from the network, in response to a request sent over the network, information about a free sample that includes:
   an advertising account for a merchant to charge the cost of the free sample for payment to a merchant account to reimburse the merchant for the free sample; and
   an identifier and quantity of the free sample; and
   writing the received information to memory of a portable consumer transaction payment device, wherein:
      the memory of the portable consumer transaction payment device has encoded therein a consumer account for the consumer to engage in a plurality of transactions on the consumer account with a plurality of said merchants in a payment processing network; and
      each said transaction in the payment processing network is submitted by the merchant to an acquirer for processing by a transaction handler who requests an issuer of the account upon which the transaction was conducted to obtain payment for the transaction from the account, and wherein the issuer of the account forwards the payment for the transaction to the transaction handler who forwards the payment for the transaction to the acquirer to reimburse the merchant for the transaction.
2. The method as defined in Embodiment 1, wherein the identifier of the free sample corresponds to a selection from the group consisting of:
   a type of a commodity of a good or service;
   a Stock Keeping Unit (SKU);
   a Universal Product Code (UPC);
   a trademark;
   a trade name of a wholesaler;
   a trade name of a manufacturer;
   an active ingredient of the type of the commodity of the good or service; and
   a combination of the foregoing.
3. The method as defined in Embodiment 1, wherein the received information further comprises an advertisement selected from the group consisting of:

an advertisement for a type of a commodity of a good or service;
an advertisement for one said merchant retailing the commodity;
an advertisement for a provider of the commodity;
an advertisement for a different said commodity also provided the provider of the commodity;
an advertisement for a different said commodity also retailed by the merchant; and
an advertisement for a different said merchant having a retail location proximal to the merchant.

4. The method as defined in Embodiment 1, wherein the consumer account of the portable consumer transaction payment device and the advertising account are different accounts each of which is a type of account selected from the group consisting of:
an account of regulated limited use for payments to healthcare providers;
a revolving credit account;
a debit account;
a prepaid account;
a Flexible Saving Account (FSA) card account;
a Health Saving Account (HAS) card account;
a Health Reimbursement Account (HRA) card account; and
a combination of the foregoing.

5. The method as defined in Embodiment 1, wherein the writing to the memory further includes writing to the memory an image corresponding to the free sample.

6. The method as defined in Embodiment 5, wherein the image is selected from the group consisting of:
an advertisement for the free sample;
an advertisement for the manufacturer of the free sample;
an offer of a discount on a purchase of the good or service corresponding to the free sample; and
a combination of the foregoing.

7. The method as defined in Embodiment 1, wherein the memory of the portable consumer transaction payment device is selected from the group consisting of:
a non-volatile memory of a semiconductor device;
a magnetic encoded data region of a magnetic stripe; and
a combination of the foregoing.

8. The method as defined in Embodiment 1, wherein the portable consumer transaction payment device is selected from the group consisting of:
a card having a Radio Frequency Identification (RFID) tag, a transponder device and a microchip; and
a magstripe card; and
a combination of the foregoing.

9. The method as defined in Embodiment 1, wherein the writing to the memory of the portable consumer transaction payment device is performed by a step selected from the group consisting of:
transmitting data wirelessly to the portable consumer transaction payment device;
transmitting data via a hardwired communication to the portable consumer transaction payment device; and
magnetically encoding track data by modifying the magnetism of magnetic particles on a band of magnetic material on the portable consumer transaction payment device.

10. The method as defined in Embodiment 1, wherein the network comprises the Internet and the method further comprises, prior to the receiving:
browsing to an Internet website in communication with a web service having a database of information that includes a plurality of different said free samples; and sending the request to the web service, wherein the request includes a selection of the free sample.

11. The method as defined in Embodiment 1, wherein data written to memory of the portable consumer transaction payment device further comprises an identifier and quantity of a plurality of other said free samples and their respective said advertising accounts.

12. A method comprising a plurality of steps each being performed by a web enabled computing apparatus by executing software, wherein the steps include:
browsing to an Internet website in communication with a web service having a database of information that includes a plurality of different free samples;
sending a request to the web service, wherein the request includes a selection of one said free sample;
receiving in a transmission from the web service, in response to the request, information about the one said free sample that includes:
an advertising account for a merchant to charge the cost of the one said free sample for payment to a merchant account to reimburse the merchant for the one said free sample;
a graphic image for rendering at a Point Of Service terminal (POS) of the merchant; and
an identifier and quantity of the one said free sample; and
writing the received information to memory of a portable consumer transaction payment device, wherein the memory of the portable consumer transaction payment device has encoded therein a consumer account for the consumer to engage in a plurality of transactions on the consumer account with a plurality of merchants in a payment processing network, and wherein each said transaction in the payment processing network is submitted by the merchant to an acquirer for processing by a transaction handler who requests an issuer of a corresponding account upon which the transaction was conducted to obtain payment for the transaction from the corresponding account, and wherein the issuer of the corresponding account forwards the payment for the transaction to the transaction handler who forwards the payment for the transaction to the acquirer to reimburse the merchant for the transaction.

13. The method as defined in Embodiment 12, wherein the consumer account is a type of account selected from the group consisting of:
a Flexible Saving Account card account;
a Health Saving Account card account;
a Health Reimbursement Account card account; and
a combination of the foregoing.

14. The method as defined in Embodiment 12, wherein the identifier of the one said free sample is selected from the group consisting of:
a bar code;
a Stock Keeping Unit (SKU);
a Universal Product Code (UPC);
a trademark;
a trade name of a wholesaler;
a trade name of a manufacturer;
an active ingredient of the type of the commodity of the good or service; and
a combination of the foregoing.

15. The method as defined in Embodiment 12, wherein the graphic image for rendering at the POS of the merchant is selected from the group consisting of:
a bar code;
a Universal Product Code (UPC);

an advertisement for a type of a commodity of a good or service;
an advertisement for the merchant;
an advertisement for a provider of the commodity;
an advertisement for a different said commodity also provided the provider of the commodity;
an advertisement for a different said commodity also retailed by the merchant; and
an advertisement for a different said merchant having a retail location proximal to the merchant.

16. The method as defined in Embodiment 12, wherein the memory of the portable consumer transaction payment device is selected from the group consisting of:
a non-volatile memory of a semiconductor device;
a magnetic encoded data region of a magnetic stripe; and
a combination of the foregoing.

17. The method as defined in Embodiment 12, wherein the portable consumer transaction payment device is selected from the group consisting of:
a card having a Radio Frequency Identification (RFID) tag, a transponder device and a microchip; and
a magstripe card; and
a combination of the foregoing.

18. The method as defined in Embodiment 12, wherein the writing to the memory of the portable consumer transaction payment device is performed by a step selected from the group consisting of:
transmitting data wirelessly to the portable consumer transaction payment device;
transmitting data via a hardwired communication to the portable consumer transaction payment device; and
magnetically encoding track data by modifying the magnetism of magnetic particles on a band of magnetic material on the portable consumer transaction payment device.

19. An apparatus comprising:
a user interface to receive a request for a free sample;
a network communication device to:
send the request for the free sample; and
receive an advertising account for a merchant to charge the cost of the free sample for payment to a merchant account to reimburse the merchant for the free sample; and
a card writer to encode data in memory of the portable consumer transaction payment device, wherein:
the data includes:
the advertising account;
an identifier and a quantity of the free sample; and
a graphic image for rendering at a Point Of Service terminal (POS) of the merchant;
the memory of the portable consumer transaction payment device includes a consumer account for a consumer to engage in a plurality of transactions on the consumer account with a plurality of said merchants in a payment processing network; and
each said transaction in the payment processing network is submitted by the merchant to an acquirer for processing by a transaction handler who requests an issuer of a corresponding account upon which the transaction was conducted to obtain payment for the transaction from the corresponding account, and wherein the issuer of the corresponding account forwards the payment for the transaction to the transaction handler who forwards the payment for the transaction to the acquirer to reimburse the merchant for the transaction.

20. The apparatus as defined in Embodiment 19, further comprising a card reader for reading consumer data encoded in the memory on the portable consumer transaction payment device.

Additional embodiments of PPD include:

1. A method comprising a plurality of steps each being performed by a computing apparatus executing software, wherein the computing apparatus is enabled for network communications, and wherein the steps include:
receiving in a transmission from the network, in response to a request sent over the network, information about a prescription medical supply sample that includes:
an advertising account for a dispensing pharmacist to charge the cost of the prescription medical supply sample for payment to a dispensing pharmacist account to reimburse the dispensing pharmacist for the prescription medical supply sample; and
an identifier, quantity, and dosage of the prescription medical supply sample;
and
writing to memory of a portable consumer transaction payment device:
the received information;
an identifier for a patient; and
an identifier for a prescribing medical practitioner prescribing the prescription medical supply sample to the patient, wherein the portable consumer transaction payment device is associated with a patient account for the patient to engage in a plurality of transactions on the patient account with a plurality of merchants in a payment processing network.

2. The method as defined in Embodiment 1, wherein the patient account of the portable consumer transaction payment device and the advertising account are different accounts each of which is a type of account selected from the group consisting of:
an account of regulated limited use for payments to healthcare providers;
a revolving credit account;
a debit account;
a prepaid account;
a Flexible Saving Account (FSA) card account;
a Health Saving Account (HAS) card account;
a Health Reimbursement Account (HRA) card account; and
a combination of the foregoing.

3. The method as defined in Embodiment 1, wherein the writing to the memory further includes writing to the memory an image of a prescription for the patient from the prescribing medical practitioner.

4. The method as defined in Embodiment 3, wherein the image of the prescription comprises respective images corresponding to:
the identifier for the patient;
the identifier for the prescribing medical practitioner of the prescription medical supply sample;
the identifier for the prescription medical supply sample; and
the quantity of the prescription medical supply sample.

5. The method as defined in Embodiment 1, wherein the memory of the portable consumer transaction payment device is selected from the group consisting of:
a non-volatile memory of a semiconductor device;
a magnetic encoded data region of a magnetic stripe; and
a combination of the foregoing.

6. The method as defined in Embodiment 1, wherein the portable consumer transaction payment device is selected from the group consisting of:
a card having a Radio Frequency Identification (RFID) tag, a transponder device and a microchip;
a magstripe card; and
a combination of the foregoing.

7. The method as defined in Embodiment 1, wherein the writing to the memory of the portable consumer transaction payment device is performed by a step selected from the group consisting of:
transmitting data wirelessly to the portable consumer transaction payment device;
transmitting data via a hardwired communication to the portable consumer transaction payment device; and
magnetically encoding track data by modifying the magnetism of magnetic particles on a band of magnetic material on the portable consumer transaction payment device.

8. The method as defined in Embodiment 1, wherein:
the dispensing pharmacist is one said merchant in the payment processing network;
the charging of the cost of the prescription medical supply sample to the advertising account for the payment to the dispensing pharmacist account is another said transaction in the payment processing network; and
each said transaction in the payment processing network is submitted by the merchant to an acquirer for processing by a transaction handler who requests an issuer of a corresponding account upon which the transaction was conducted to obtain payment for the transaction from the corresponding account, and wherein the issuer of the corresponding account forwards the payment for the transaction to the transaction handler who forwards the payment for the transaction to the acquirer to reimburse the merchant for the transaction.

9. The method as defined in Embodiment 1, wherein the network comprises the Internet and the method further comprises, prior to the receiving:
browsing to an Internet website in communication with a web service having a database of information that includes a plurality of different free pharmaceutical samples; and
sending the request to the web service, wherein the request includes a selection of the prescription medical supply sample.

10. The method as defined in Embodiment 1, wherein data written to memory of the portable consumer transaction payment device further comprises an identifier, a quantity, and a dosage of a prescription medical supply, other than the prescription medical supply sample, being prescribed by the prescribing medical practitioner to the patient.

11. A method comprising a plurality of steps each being performed by a computing apparatus by executing software, the computing apparatus being enabled for network communications, wherein the steps include:
receiving a transmission from a network, in response to a request, information about a prescription medical supply sample that includes:
an advertising account for a dispensing pharmacist to charge the cost of the prescription medical supply sample for payment to a dispensing pharmacist account to reimburse the dispensing pharmacist for the prescription medical supply sample; and
an identifier, quantity, and dosage of the prescription medical supply sample; and
writing to memory of a portable consumer health services payment device:
the received information;
an identifier for a patient;
an identifier for a prescribing medical practitioner prescribing the prescription medical supply sample to the patient; and
an identifier, a quantity, and a dosage of a prescription medical supply, other than the prescription medical supply sample, being prescribed by the prescribing medical practitioner to the patient, wherein the patient account is regulated for limited use for payments to the healthcare providers and is for the dispensing pharmacist to charge the cost of the prescription medical supply for payment to the dispensing pharmacist account to reimburse the dispensing pharmacist for the prescription medical supply.

12. The method as defined in Embodiment 11, wherein:
the dispensing pharmacist is one said merchant in the payment processing network;
the charging of the cost of the prescription medical supply sample to the advertising account for the payment to the dispensing pharmacist account is another said transaction in the payment processing network; and
each said transaction in the payment processing network is submitted by the merchant to an acquirer for processing by a transaction handler who requests an issuer of a corresponding account upon which the transaction was conducted to obtain payment for the transaction from the corresponding account, and wherein the issuer of the corresponding account forwards the payment for the transaction to the transaction handler who forwards the payment for the transaction to the acquirer to reimburse the merchant for the transaction.

13. The method as defined in Embodiment 11, wherein the patient account is a type of account selected from the group consisting of:
a Flexible Saving Account card account;
a Health Saving Account card account;
a Health Reimbursement Account card account; and
a combination of the foregoing.

14. The method as defined in Embodiment 11, wherein the writing to the memory further includes writing to the memory an image of a prescription for the patient from the prescribing medical practitioner.

15. The method as defined in Embodiment 14, wherein the image of the prescription comprises respective images corresponding to:
the identifier for the patient;
the identifier for the prescribing medical practitioner of the prescription medical supply sample;
the identifier for the prescription medical supply sample; and
the quantity of the prescription medical supply sample.

16. The method as defined in Embodiment ii, wherein the memory of the portable consumer health services payment device is selected from the group consisting of:
a non-volatile memory of a semiconductor device;
a magnetic encoded data region of a magnetic stripe; and
a combination of the foregoing.

17. The method as defined in Embodiment 11, wherein the portable consumer health services payment device is selected from the group consisting of:
a card having a Radio Frequency Identification (RFID) tag, a transponder device and a microchip;
a magstripe card; and
a combination of the foregoing.

18. The method as defined in Embodiment 11, wherein the writing to the memory of the portable consumer health services payment device is performed by a step selected from the group consisting of:
transmitting data wirelessly to the portable consumer health services payment device;
transmitting data via a hardwired communication to the portable consumer health services payment device; and
magnetically encoding track data by modifying the magnetism of magnetic particles on a band of magnetic material on the portable consumer health services payment device.
19. The method as defined in Embodiment ii, wherein the network comprises the Internet and the method further comprises, prior to the receiving of the transmission:
browsing to an Internet website in communication with a web service having a database of information that includes a plurality of different free pharmaceutical samples; and
sending the request to the web service, wherein the request includes a selection of the prescription medical supply sample.
20. An apparatus comprising:
a user interface to receive a request for a prescription medical supply sample;
a network communication device to:
send the request for the prescription medical supply sample; and
receive an advertising account for a dispensing pharmacist to charge the cost of the prescription medical supply sample for payment to a dispensing pharmacist account to reimburse the dispensing pharmacist for the prescription medical supply sample; and
a card writer to encode prescription data in memory of the portable consumer transaction payment device, wherein:
the prescription data includes:
the advertising account;
an identifier for a patient; and
an identifier for a prescribing medical practitioner;
an identifier, a quantity, and a dosage of:
the prescription medical supply sample; and
a prescription medical supply, other than the prescription medical supply sample, being prescribed by the prescribing medical practitioner to the patient; and
an image of a prescription for the patient from the prescribing medical practitioner;
the memory of the portable consumer transaction payment device includes a consumer account for a consumer to engage in a plurality of transactions on the consumer account with a plurality of merchants in a payment processing network;
the dispensing pharmacist is one said merchant in the payment processing network;
the charging of the cost of the prescription medical supply sample to the advertising account for the payment to the dispensing pharmacist account is another said transaction in the payment processing network; and
each said transaction in the payment processing network is submitted by the merchant to an acquirer for processing by a transaction handler who requests an issuer of a corresponding account upon which the transaction was conducted to obtain payment for the transaction from the corresponding account, and wherein the issuer of the corresponding account forwards the payment for the transaction to the transaction handler who forwards the payment for the transaction to the acquirer to reimburse the merchant for the transaction.
21. The apparatus as defined in Embodiment 20, further comprising a card reader for reading consumer data encoded in the memory on the portable consumer transaction payment device.

Additional PPD embodiments include:
1. For a payment processing network that includes a plurality of merchants and consumers engaging in a plurality of transactions on a plurality of respective consumer accounts that respective issuers issue to the consumers, each said transaction involving a free sample associated with a free sample account issued by an issuer, wherein the merchant submits the transaction to an acquirer for processing by a transaction handler who requests the issuer to obtain payment for the free sample given by the merchant to the consumer in the transaction from the free sample account, and wherein the issuer forwards the payment to the transaction handler who forwards the payment to the acquirer to reimburse the merchant for the free sample given in the transaction, a method of providing a free sample account transaction payment card to a user of a kiosk, the method comprising:
receiving, at an input device of a user interface of the kiosk, a selection a free sample from a database having a plurality of selectable said free samples each:
being associated with a free sample account issued by an issuer to a sponsor financially responsible for the cost of providing the free sample to one said consumer, wherein:
the free sample account is acceptable by one said merchant for payment in one said transaction in which the one said merchant tenders the free sample to the one said consumer;
the cost of the free sample is to be debited from the free sample account and credited to a merchant account for the one said merchant to be reimbursed for tendering the free sample to the one said consumer; and
the merchant account is issued by another said issuer to the one said merchant;
retrieving, from the database, to memory in the kiosk:
a rendering image corresponding to a rendering capability of the kiosk; and
the free sample information including an identifier for:
the free sample account;
a quantifier for the fee sample; and
at least one of a good and a service;
writing, from the memory in the kiosk with a card writing device of the kiosk, the free sample information to a memory location in a free sample account transaction payment card stored within the kiosk; and
rendering a hard copy of the rendering image on a surface of the free sample account transaction payment card.
2. The method of Embodiment 1, wherein said retrieving further comprises connecting to a network, wherein the database is stored on the network.
3. The method of Embodiment 1, wherein the rendering image includes a bar code corresponding to the free sample information.
4. The method of Embodiment 1, further comprising displaying, on the user interface of the kiosk, an advertisement associated with each of the selectable said free samples.
5. The method of Embodiment 1, wherein the rendering image includes an advertisement for the free sample.
6. The method of Embodiment 1, wherein the free sample account is issued to a member of the group consisting of:

the one said merchant;
a manufacturer of the free sample;
a wholesaler of the free sample; and
a distributor of the free sample.

7. For a payment processing network that includes a plurality of merchants and consumers engaging in a plurality of transactions on a plurality of respective consumer accounts that respective issuers issue to the consumers, each said transaction involving an electronic coupon associated with a sponsor account issued by an issuer, wherein the merchant submits the transaction to an acquirer for processing by a transaction handler who requests the issuer to obtain payment for a discount applied by the merchant to the transaction from the sponsor account, and wherein the issuer forwards the payment to the transaction handler who forwards the payment to the acquirer to reimburse the merchant for the discount given on the transaction, a kiosk comprising:

means for displaying a plurality of selectable said free samples each:
being associated with a free sample account issued by an issuer to a sponsor financially responsible for the cost of providing the free sample to one said consumer, wherein:
the free sample account is acceptable by one said merchant for payment in one said transaction in which the one said merchant tenders the free sample to the one said consumer;
the cost of the free sample is to be debited from the free sample account and credited to a merchant account for the one said merchant to be reimbursed for tendering the free sample to the one said consumer; and
the merchant account is issued by another said issuer to the one said merchant;
means for receiving a selection of a free sample from the selectable said free samples;
means for retrieving, from the database, to memory in the kiosk:
a rendering image corresponding to a rendering capability of the kiosk; and
the free sample information including an identifier for:
the free sample account;
a quantifier for the fee sample; and
at least one of a good and a service;
means for writing, with a card writing device of the kiosk, the free sample information from the memory in the kiosk to memory in a free sample account transaction payment card; and
means for rendering a hard copy of the rendering image on a surface of the free sample account transaction payment card.

8. The kiosk of Embodiment 7, wherein said means for retrieving includes a means for communicating with a network, wherein the database is stored on the network.

9. The kiosk of Embodiment 7, wherein the rendering image includes a bar code corresponding to the free sample information.

10. The kiosk of Embodiment 7, wherein the means for displaying further comprises an advertisement associated with each of the selectable said free samples.

11. The kiosk of Embodiment 7, wherein the rendering image includes an advertisement for the free sample.

12. The kiosk of Embodiment 7, wherein the free sample account is issued to a member of the group consisting of:
the one said merchant;
a manufacturer of the free sample;
a wholesaler of the free sample; and
a distributor of the free sample.

13. A kiosk comprising:
a user interface having a display device and an input device;
memory;
a computing apparatus executing an internet browser to:
access a web site associated with a server serving one or more web pages for displaying on the display device a plurality of selectable said free samples each:
being associated with a free sample account issued by an issuer to a sponsor who is financially responsible for the cost of providing the free sample to a consumer, wherein:
the free sample account is acceptable by a merchant for payment in a transaction in which the merchant tenders the free sample to the consumer;
the cost of the free sample is to be debited from the free sample account and credited to a merchant account for the merchant to be reimbursed for tendering the free sample to the consumer; and
the merchant account is issued by another said issuer to the merchant;
transmit to the server input received at the input device and corresponding to a selection of a free sample from the selectable said free samples;
receive from the server for storage in the memory of the kiosk:
a rendering image corresponding to a rendering capability of the kiosk; and
the free sample information including an identifier for:
the free sample account;
a quantifier for the fee sample; and
at least one of a good and a service; and
a card writing device to:
write the free sample information from the memory in the kiosk to memory in a free sample account transaction payment card; and
render a hard copy of the rendering image on a surface of the free sample account transaction payment card.

14. The kiosk of Embodiment 13, wherein the rendering image includes a bar code corresponding to the free sample information.

15. The kiosk of Embodiment 13, wherein the one or more web pages for displaying on the display device further comprises an advertisement associated with each of the selectable said free samples.

16. The kiosk of Embodiment 13, wherein the rendering image includes an advertisement for the free sample.

17. The kiosk of Embodiment 13, wherein the free sample account is issued to a member of the group consisting of:
the merchant;
a manufacturer of the free sample;
a wholesaler of the free sample; and
a distributor of the free sample.

18. The kiosk of Embodiment 13, wherein the memory in the free sample account transaction payment card is selected from the group consisting of:
a non-volatile memory of a semiconductor device;
a magnetic encoded data region of a magnetic stripe; and
a combination of the foregoing.

19. The kiosk of Embodiment 13, wherein the free sample account transaction payment card is selected from the group consisting of:
a card having a Radio Frequency Identification (RFID) tag, a transponder device and a microchip; and
a magstripe card; and
a combination of the foregoing.

20. The kiosk of Embodiment 13, wherein the card writing device writes to the memory of the free sample account transaction payment card by a process selected from the group consisting of:

transmitting data wirelessly to the free sample account transaction payment card;

transmitting data via a hardwired communication to the free sample account transaction payment card; and magnetically encoding track data by modifying the magnetism of magnetic particles on a band of magnetic material on the free sample account transaction payment card.

Additional PPD embodiments may include:

1. A method comprising a plurality of steps performed by a computing apparatus executing software, wherein the steps include:

receiving, using an input device of a user interface:

an identifier, quantity, and dosage of a free prescription medical supply sample; and an identifier for a patient;

sending a transmission out to a network including the identifier for the free prescription medical supply sample;

receiving a transmission from the network, in response to the sending, and including free prescription medical supply sample information including:

a pharmaceutical company account for a dispensing pharmacist to charge the cost of the free prescription medical supply sample for payment to a dispensing pharmacist account to reimburse the dispensing pharmacist for the free prescription medical supply sample;

the identifier, quantity, and dosage of the free prescription medical supply sample; and an image corresponding to the free prescription medical supply sample;

receiving a prescription medical supply sample transaction payment card;

writing to memory of the prescription medical supply sample transaction payment card:

the free prescription medical supply sample information;

an identifier for a patient; and an identifier for a prescribing medical practitioner prescribing the free prescription medical supply sample to the patient;

and rendering the image corresponding to the free prescription medical supply sample on a surface of the prescription medical supply sample transaction payment card.

2. The method as defined in Embodiment 1, wherein:

the pharmaceutical company account is a type of consumer account issued by an issuer to a pharmaceutical company;

the prescription medical supply sample transaction payment card is a type of a portable consumer transaction payment device that is associated with a consumer account for a consumer to engage in a plurality of transactions on the consumer account with a plurality of merchants in a payment processing network;

the payment processing network includes a plurality of merchants and consumers engaging in a plurality of transactions on a plurality of respective consumer accounts that respective issuers issue to the consumers; and each said transaction involves the merchant submitting the transaction to an acquirer for processing by a transaction handler who requests the issuer to obtain payment for the transaction from the consumer account, and wherein the issuer forwards the payment to the transaction handler who forwards the payment to the acquirer to reimburse the merchant for the transaction.

3. The method as defined in Embodiment 1, wherein the writing to the memory of the prescription medical supply sample transaction payment card further includes writing to the memory an image of a prescription for the patient from the prescribing medical practitioner.

4. The method as defined in Embodiment 3, wherein the image of the prescription comprises respective images corresponding to:

the identifier for the patient;

the identifier for the prescribing medical practitioner of the free prescription medical supply sample;

the identifier for the free prescription medical supply sample; and the quantity of the free prescription medical supply sample.

5. The method as defined in Embodiment 1, wherein the image corresponding to the free prescription medical supply sample includes a code identifying the free prescription medical supply and configured for being scanned by a scanner at a Point of Service terminal.

6. The method as defined in Embodiment 1, wherein the image corresponding to the free prescription medical supply sample includes an advertisement selected from the group consisting of:

an advertisement for the free prescription medical supply;

an advertisement not for the free prescription medical supply;

an advertisement for the dispensing pharmacist;

an advertisement for a different product other than the free prescription medical supply that is also provided by the dispensing pharmacist; and a combination of the foregoing.

7. The method as defined in Embodiment 1, wherein the steps further comprise retrieving a geographic location for the dispensing pharmacist, wherein the image corresponding to the free prescription medical supply sample includes an advertisement selected from the group consisting of:

an advertisement for a merchant geographically proximal to the prescribing medical practitioner;

an advertisement for a merchant geographically proximal to the dispensing pharmacist; and a combination of the foregoing.

8. The method as defined in Embodiment 1, wherein the memory of the prescription medical supply sample transaction payment card is selected from the group consisting of:

a non-volatile memory of a semiconductor device;

a magnetic encoded data region of a magnetic stripe; and a combination of the foregoing.

9. The method as defined in Embodiment 1, wherein the prescription medical supply sample transaction payment card is selected from the group consisting of:

a card having a Radio Frequency Identification (RFID) tag, a transponder device and a microchip; and a magstripe card; and a combination of the foregoing.

10. The method as defined in Embodiment 1, wherein the writing to the memory of the prescription medical supply sample transaction payment card is performed by a step selected from the group consisting of:

transmitting data wirelessly to the prescription medical supply sample transaction payment card;

transmitting data via a hardwired communication to the prescription medical supply sample transaction payment card; and magnetically encoding track data by modifying the magnetism of magnetic particles on a band of magnetic material on the prescription medical supply sample transaction payment card.

11. The method as defined in Embodiment 1, wherein the network comprises the Internet and the method further comprises:

browsing, using the input device, to an Internet website in communication with a web service having a database of information that includes a plurality of different free pharmaceutical samples; and sending other said transmissions out to the network including respective requests to the web service each of which includes a selection of a different said free prescription medical supply sample; and receiving other said transmissions from the network, in response to the sending of the other said transmissions, and including free prescription medical supply sample information respectively corresponding to each selection of the different said free prescription medical supply sample.

12. The method as defined in Embodiment 1, wherein the steps further comprise receiving, using the input device of the user interface, an identifier, a quantity, and a dosage of a prescription medical supply, other than the free prescription medical supply sample, being prescribed by the prescribing medical practitioner to the patient.

13. The method as defined in Embodiment 1, wherein data written to memory of the prescription medical supply sample transaction payment card further comprises an identifier, a quantity, and a dosage of a prescription medical supply, other than the free prescription medical supply sample, being prescribed by the prescribing medical practitioner to the patient.

14. A method comprising a plurality of steps performed by a computing apparatus executing software, wherein the steps include:

browsing, using an input device of a user interface, to an Internet website in communication with a web service having a database of information that includes a plurality of different free pharmaceutical samples;

receiving, using the input device of the user interface:

an identifier, quantity, and dosage of:

a selected one said free prescription medical supply sample; and a prescription for a prescription medical supply, other than the selected one said free prescription medical supply sample, being prescribed by a prescribing medical practitioner to a patient;

sending a transmission out to the web service including the identifier for the selected one said free prescription medical supply sample;

receiving a transmission from the network, in response to the sending, and including free prescription medical supply sample information including:

a pharmaceutical company account for a dispensing pharmacist to charge the cost of the selected one said free prescription medical supply sample for payment to a dispensing pharmacist account to reimburse the dispensing pharmacist for the selected one said free prescription medical supply sample; and an image corresponding to the selected one said free prescription medical supply sample;

receiving a prescription medical supply sample transaction payment card;

writing to memory of the prescription medical supply sample transaction payment card:

the free prescription medical supply sample information;

the identifier for the patient;

an identifier for the prescribing medical practitioner prescribing:

the prescription to the patient; and the selected one said free prescription medical supply sample; and an image of the prescription for the patient from the prescribing medical practitioner; and rendering the image corresponding to the selected one said free prescription medical supply sample on a surface of the prescription medical supply sample transaction payment card, wherein:

the pharmaceutical company account is a type of consumer account issued by an issuer to a pharmaceutical company;

the prescription medical supply sample transaction payment card is a type of a portable consumer transaction payment device that is associated with a consumer account for a consumer to engage in a plurality of transactions on the consumer account with a plurality of merchants in a payment processing network;

the payment processing network includes a plurality of merchants and consumers engaging in a plurality of transactions on a plurality of respective consumer accounts that respective issuers issue to the consumers; and each said transaction involves the merchant submitting the transaction to an acquirer for processing by a transaction handler who requests the issuer to obtain payment for the transaction from the consumer account, and wherein the issuer forwards the payment to the transaction handler who forwards the payment to the acquirer to reimburse the merchant for the transaction.

15. An apparatus comprising:

means for receiving:

an identifier, quantity, and dosage of a free prescription medical supply sample;

an identifier for a prescribing medical practitioner; and an identifier for a patient;

first communication means for sending a transmission out to a network including the identifier for the free prescription medical supply sample;

second communication means for receiving a transmission from the network, in response to the sending, including free prescription medical supply sample information that includes:

a pharmaceutical company account for a dispensing pharmacist to charge the cost of the free prescription medical supply sample for payment to a dispensing pharmacist account to reimburse the dispensing pharmacist for the free prescription medical supply sample; and an image corresponding to the free prescription medical supply sample;

means for writing to data in memory of a prescription medical supply sample transaction payment card, the data including:

the identifier, quantity, and dosage of the free prescription medical supply sample;

the identifier for a prescribing medical practitioner;

the identifier for the patient; and the pharmaceutical company account;

and means for printing the image corresponding to the free prescription medical supply sample on a surface of the prescription medical supply sample transaction payment card.

16. The apparatus as defined in Embodiment 15, wherein:

the means for receiving further comprises means for receiving an identifier, a quantity, and a dosage of a prescription medical supply, other than the free prescription medical supply sample, being prescribed by the prescribing medical practitioner to the patient; and the data written in the memory of the prescription medical supply sample transaction payment card by the means for writing further comprises the identifier, the quantity, and the dosage of the prescription medical supply, other than the free prescription medical supply sample, being prescribed by the prescribing medical practitioner to the patient.

17. The apparatus as defined in Embodiment 15, wherein:

the pharmaceutical company account being used by the dispensing pharmacist to charge the cost of the free prescription medical supply sample for payment to the dispensing pharmacist account to reimburse the dispensing pharmacist for the free prescription medical supply sample corresponds to a transaction in a payment processing network;

the dispensing pharmacist is a merchant;

the patient is a consumer;

the pharmaceutical company account is a consumer account; and the payment processing network includes a plurality of said merchants and said consumers engaging in a plurality of said transactions on a plurality of respective said consumer accounts that respective issuers issue to the consumers, each said transaction involving the merchant submitting the transaction to an acquirer for processing by a transaction handler who requests the issuer to obtain payment for the transaction from the corresponding consumer account, and wherein the issuer forwards the payment to the transaction handler who forwards the payment to the acquirer to reimburse the merchant for the transaction.

18. The apparatus as defined in Embodiment 17, wherein the pharmaceutical company account is issued by one said issuer to a member of the group comprising:

the merchant in the transaction;

a manufacturer of the purchase;

a wholesaler of the free prescription medical supply sample; and a distributor of the free prescription medical supply sample.

19. The apparatus as defined in Embodiment 15, wherein the image printed on the surface of the prescription medical supply sample transaction payment card includes a bar code that is scannable by a scanner at a Point of Service terminal.

20. The apparatus as defined in Embodiment 15, wherein:

the memory of the prescription medical supply sample transaction payment card is selected from the group consisting of:

a non-volatile memory of a semiconductor device;

a magnetic encoded data region of a magnetic stripe; and a combination of the foregoing; and the prescription medical supply sample transaction payment card is selected from the group consisting of:

a card having a Radio Frequency Identification (RFID) tag, a transponder device and a microchip;

a magstripe card; and a combination of the foregoing.

Additional PPD embodiments include:

1. A portable coupon payment device comprising: a substrate having surface with an image rendering thereon that corresponds to a free sample; and memory, in contact with the substrate, having data encoded therein including: an identifier for the free sample; and a quantity for the free sample; a sponsor company account for a selling merchant to charge the cost of the free sample for payment to a selling merchant account to reimburse the selling merchant for the free sample; an image corresponding to the free sample; and an identifier for a coupon provider donating the free sample to a consumer.

2. The portable coupon payment device as defined in embodiment 1, wherein: the sponsor company account is a type of consumer account issued by an issuer to a sponsor company; the portable coupon payment device is a type of a portable coupon payment device that is associated with a consumer account for a consumer to engage in a plurality of transactions on the consumer account with a plurality of merchants in a payment processing network; the payment processing network includes a plurality of merchants and consumers engaging in a plurality of transactions on a plurality of respective consumer accounts that respective issuers issue to the consumers; and each said transaction involves the merchant submitting the transaction to an acquirer for processing by a transaction handler who requests the issuer to obtain payment for the transaction from the consumer account, and wherein the issuer forwards the payment to the transaction handler who forwards the payment to the acquirer to reimburse the merchant for the transaction.

3. The portable coupon payment device as defined in embodiment 1, wherein the data encoded in the memory further includes an image of a donation for the consumer from the coupon provider.

4. The portable coupon payment device as defined in embodiment 3, wherein the image of the donation comprises respective images corresponding to: the identifier for the consumer; the identifier for the coupon provider of the free sample; the identifier for the free sample; and the quantity of the free sample.

5. The portable coupon payment device as defined in embodiment 1, wherein the image corresponding to the free sample includes a code identifying the free sample and configured for being scanned by a scanner at a Point of Service terminal.

6. The portable coupon payment device as defined in embodiment 1, wherein the image corresponding to the free sample includes an advertisement selected from the group consisting of: an advertisement for the free sample; an advertisement not for the free sample; an advertisement for the selling merchant; an advertisement for a different product other than the free sample that is also provided by the selling merchant; and a combination of the foregoing.

7. The portable coupon payment device as defined in embodiment 1, wherein the image corresponding to the free sample includes an advertisement selected from the group consisting of: an advertisement for a merchant geographically proximal to the coupon provider; an advertisement for a merchant geographically proximal to the selling merchant; and a combination of the foregoing.

8. The portable coupon payment device as defined in embodiment 1, wherein the memory of the portable coupon payment device is selected from the group consisting of: a non-volatile memory of a semiconductor device; a magnetic encoded data region of a magnetic stripe; and a combination of the foregoing.
9. The portable coupon payment device as defined in embodiment 1, wherein the substrate is a portion of a consumer transaction payment card selected from the group consisting of: a smart card having a Radio Frequency Identification (RFID) tag, a transponder device and a microchip; and a magstripe card; and a combination of the foregoing.
10. The portable coupon payment device as defined in embodiment 1, further comprising means for the memory to receive the information by a communication selected from the group consisting of a wireless communication, a hardwired communication, and a magnetic encoded communication for track data received by modifying the magnetism of magnetic particles on a band of magnetic material on the portable coupon payment device.
11. The portable coupon payment device as defined in embodiment 1, wherein data in the memory of the portable coupon payment device further comprises an identifier, a quantity, and a quantity of an item, other than the free sample, being donated by the coupon provider to the consumer.
12. The portable coupon payment device as defined in embodiment 11, wherein the identifier for the free sample and the identifier for the item, other than the free sample, are both selected from the group consisting of: a Stock Keeping Unit (SKU); a Universal Product Code (UPC); a trademark; a commodity type and a trade name of a provider of the commodity type; an ingredient of the commodity type and the trade name of the provider of the commodity type; and a combination of the foregoing.
13. A portable coupon transaction payment device comprising: memory, embedded in a substrate, having stored therein: an identifier and a quantity for each of a plurality of: a free sample donated by a coupon provider to a consumer; and a non-sample item each being offered by a corresponding said coupon provider to the consumer; for each said free sample, a sponsor company account for a selling merchant to charge the cost of the free sample for payment to a selling merchant account to reimburse the selling merchant for the free sample; an identifier for the consumer; an identifier for each said coupon provider; an identifier for a consumer account issued by an issuer to the consumer; and an identifier to correlate which said donation for the consumer was donated by which said coupon provider, wherein: the sponsor company account and the consumer account are each an account in a payment processing network by which a consumer can engage in a plurality of transactions on the account with a plurality of merchants in the payment processing network; the payment processing network includes a plurality of said merchants and said consumers engaging in the plurality of said transactions on a plurality of respective said accounts that respective said issuers issue to the consumers; and each said transaction involves the merchant submitting the transaction to an acquirer for processing by a transaction handler who requests the issuer to obtain payment for the transaction from the account, wherein the issuer forwards the payment to the transaction handler who forwards the payment to the acquirer to reimburse the merchant for the transaction; and means for providing access to the information in the memory.
14. The portable coupon transaction payment device as defined in embodiment 13, wherein the consumer account issued by the issuer to the consumer is a type selected from the group consisting of a debit account, a credit account, a prepaid account, and a gift card account.
15. The portable coupon transaction payment device as defined in embodiment 13, wherein the substrate has an image in a surface that the includes representing at least a portion of the information in the memory for being read by the image being scanned by a scanner at a Point of Service terminal.
16. The portable coupon transaction payment device as defined in embodiment 13, wherein the memory is selected from the group consisting of: a non-volatile memory of a semiconductor device; a magnetic encoded data region of a magnetic stripe; and a combination of the foregoing.
17. The portable coupon transaction payment device as defined in embodiment 13, wherein the substrate is a portion of a consumer transaction payment card selected from the group consisting of: a smart card having a Radio Frequency Identification (RFID) tag, a transponder device and a microchip; and a magstripe card; and a combination of the foregoing.
18. The portable coupon transaction payment device as defined in embodiment 13, wherein the information in the memory further includes an image of each said free sample for the consumer that was donated by the corresponding said coupon provider.
19. The portable coupon transaction payment device as defined in embodiment 18, wherein, for each said image of each said free sample, the free sample in the image is hand written by the coupon provider.
20. The portable coupon transaction payment device as defined in embodiment 18, further comprising means for the memory to receive the information by a communication selected from the group consisting of a wireless communication, a hardwired communication, and a magnetic encoded communication for track data received by modifying the magnetism of magnetic particles on a band of magnetic material on the portable coupon payment device.
21. The portable coupon transaction payment device as defined in embodiment 20, wherein, for each said image of each said free sample, the identifier for the coupon provider comprises a handwritten signature of the coupon provider.
22. The portable coupon transaction payment device as defined in embodiment 18, wherein each said image of each said free sample comprises respective images corresponding to: the identifier for the consumer; the identifier for the coupon provider; and the identifier and the quantity for the free sample; and the identifier, quantity, and dosage identifier for the non-sample item.
23. A portable coupon transaction payment device comprising: memory, embedded in a substrate, having information stored therein, wherein: the substrate has an image on a surface thereof that includes a representation of at least a portion of the information in the memory for being read by the image being scanned by a scanner at a Point of Service terminal: the information includes: an identifier and a quantity for each of a plurality of: a free sample donated by a coupon provider to a consumer; and a non-sample item offered by a corresponding said coupon provider to the consumer; an image, having multiple portion, of each said donation for the consumer that was donated by the corresponding said coupon provider, wherein the portions of the image correspond to: the identifier for the consumer; the identifier for the coupon provider; and the identifier and the quantity for the free sample; and the identifier and the quantity for the non-sample item; for each said free sample, a sponsor company account for a selling merchant to charge the cost of the free sample for payment to a selling merchant account to reimburse the selling merchant for the free sample; and an identifier to correlate which said donation for the consumer was donated by which said coupon provider, wherein: the sponsor company account and the consumer account are each an account in a payment processing network by which a consumer can engage in a plurality of transactions on the account with a plurality of merchants in the payment processing network; the payment processing network includes a plurality of said merchants and said consumers engaging in the plurality of said transactions on a plurality of respective said accounts that respective said issuers issue to the consumers; and each said transaction involves the merchant submitting the transaction to an acquirer for processing by a transaction handler who requests the issuer to obtain payment for the transaction from the account, wherein the issuer forwards the payment to the transaction handler who forwards the payment to the acquirer to reimburse the merchant for the transaction; and means for providing access to the information in the memory.

24. The portable coupon transaction payment device as defined in embodiment 23, wherein the memory is selected from the group consisting of: a non-volatile memory of a semiconductor device; a magnetic encoded data region of a magnetic stripe; and a combination of the foregoing.

25. The portable coupon transaction payment device as defined in embodiment 23, wherein the substrate is a portion of a consumer transaction payment card selected from the group consisting of: a smart card having a Radio Frequency Identification (RFID) tag, a transponder device and a microchip; and a magstripe card; and a combination of the foregoing.

26. The portable coupon transaction payment device as defined in embodiment 23, further comprising means for the memory to receive the information by a communication selected from the group consisting of a wireless communication, a hardwired communication, and a magnetic encoded communication for track data received by modifying the magnetism of magnetic particles on a band of magnetic material on the portable coupon payment device.

27. The portable coupon transaction payment device as defined in embodiment 23, wherein, for each said image of each said donation, the identifier for the coupon provider comprises a handwritten signature of the coupon provider.

28. The portable coupon transaction payment device as defined in embodiment 23, wherein, for each said image of each said free sample, the free sample in the image is hand written by the coupon provider.

In order to address various issues and advance the art, the entirety of this application for PORTABLE PRESCRIPTION PAYMENT DEVICE MANAGEMENT PLATFORM APPARATUSES, METHODS AND SYSTEMS (including the Cover Page, Title, Headings, Field, Background, Summary, Brief Description of the Drawings, Detailed Description, Claims, Abstract, Figures, Appendices and/or otherwise) shows by way of illustration various embodiments in which the claimed innovations may be practiced. The advantages and features of the application are of a representative sample of embodiments only, and are not exhaustive and/or exclusive. They are presented only to assist in understanding and teach the claimed principles. It should be understood that they are not representative of all claimed innovations. As such, certain aspects of the disclosure have not been discussed herein. That alternate embodiments may not have been presented for a specific portion of the innovations or that further undescribed alternate embodiments may be available for a portion is not to be considered a disclaimer of those alternate embodiments. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure. Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure. Furthermore, it is to be understood that such features are not limited to serial execution, but rather, any number of threads, processes, services, servers, and/or the like that may execute asynchronously, concurrently, in parallel, simultaneously, synchronously, and/or the like are contemplated by the disclosure. As such, some of these features may be mutually contradictory, in that they cannot be simultaneously present in a single embodiment. Similarly, some features are applicable to one aspect of the innovations, and inapplicable to others. In addition, the disclosure includes other innovations not presently claimed. Applicant reserves all rights in those presently unclaimed innovations, including the right to claim such innovations, file additional applications, continuations, continuations in part, divisions, and/or the like thereof. As such, it should be understood that advantages, embodiments, examples, functional, features, logical, operational, organizational, structural, topological, and/or other aspects of the disclosure are not to be considered limitations on the disclosure as defined by the claims or limitations on equivalents to the claims. It is to be understood that, depending on the particular needs and/or characteristics of a PPD individual and/or enterprise user, database configuration and/or relational model, data type, data transmission and/or network framework, syntax structure, and/or the like, various embodiments of the PPD may be implemented that enable a great deal of flexibility and customization. For example, aspects of the PPD may be adapted for financial trading; operations security; resource management; and/or the like. While various embodiments and discussions of the PPD have been directed to restricted product supply management, however, it is to be understood that the embodiments described herein may be readily configured and/or customized for a wide variety of other applications and/or implementations.

What is claimed is:

1. A prescription medical supply sample dispensing transaction processor-implemented method, comprising:
   receiving a prescription medical supply sample dispensing authorization request from a dispensing pharmacist,
   said prescription medical supply sample dispensing authorization request including information loaded from a portable consumer device storing a graphic image of the prescription medical supply sample and information of an electronic voucher;
   obtaining an account identifier associated with the electronic voucher;
   sending a verification request to an issuer of the electronic voucher to verify the account associated with the electronic voucher has been loaded with sufficient funds by a sponsor to pay for the requested drug sample distribution;
   sending an authorization response to the dispensing pharmacist upon receipt of the verification from the issuer; and
   transacting an amount to cover the requested prescription medical supply sample dispensing from the account associated with the electronic voucher to the dispensing pharmacist.

2. The method of claim 1, wherein the portable consumer device is associated with any of the following accounts:
   an account of regulated limited use for payments to healthcare providers;
   a revolving credit account;
   a debit account;
   a prepaid account;
   a Flexible Saving Account (FSA) card account;
   a Health Saving Account (HAS) card account;
   a Health Reimbursement Account (HRA) card account; and
   a combination of the foregoing.

3. The method of claim 1, wherein the graphic image of the prescription medical supply sample is printed on a surface of the portable consumer device.

4. The method of claim 3, wherein the graphic image of the prescription medical supply sample comprises respective images corresponding to: an identifier for s patient; an identifier for a prescribing medical practitioner of the prescription medical supply sample; an identifier for the prescription medical supply sample; and a quantity of the prescription medical supply sample.

5. The method of claim 1, wherein a memory of the portable consumer device comprises any of: a non-volatile memory of a semiconductor device; a magnetic encoded data region of a magnetic stripe.

6. The method of claim 1, wherein the portable consumer device comprises any of: a card having a Radio Frequency Identification (RFID) tag, a transponder device and a microchip; and a magstripe card.

7. The method of claim 1, further comprising:
   transmitting data wirelessly to the portable consumer device;
   transmitting data via a hardwired communication to the portable consumer device; and
   magnetically encoding track data by modifying the magnetism of magnetic particles on a band of magnetic material on the portable consumer device.

8. The method of claim 1, further comprising:
   charging a cost of the prescription medical supply sample to an advertising account for the payment to a dispensing pharmacist account.

9. The method of claim 1, further comprising:
   prior to the receiving: browsing to an Internet website in communication with a web service having a database of information that includes a plurality of different free pharmaceutical samples; and
   sending the request to the web service, wherein the request includes a selection of the prescription medical supply sample.

10. The method of claim 1, wherein the portable consumer device further comprises an identifier, a quantity, and a dosage of a prescription medical supply, other than the prescription medical supply sample, being prescribed by the prescribing medical practitioner to the patient.

11. The method of claim 1, wherein the sponsor comprises any of:
    a merchant in the transaction;
    a manufacturer of the purchase;
    a wholesaler of the free prescription medical supply sample; and
    a distributor of the free prescription medical supply sample.

12. The method of claim 1, wherein the graphic image includes a bar code that is scanable by a scanner at a Point of Service terminal.

13. The method of claim 1, wherein the prescription medical supply sample comprises a free product sample.

14. The method of claim 1, wherein the portable consumer device comprises: a substrate having surface with an image rendering thereon that corresponds to a free sample.

15. The method of claim 1, wherein the portable consumer device comprises:
    information of a sponsor company account for a selling merchant to charge a cost of the f prescription medical supply sample.

16. The method of claim 1, further comprising:
    writing to data in memory of the portable consumer device.

17. The method of claim 16, wherein the data written comprises:
    the identifier, quantity, and dosage of the prescription medical supply sample;
    the identifier for a prescribing medical practitioner; and
    the identifier for a patient.

18. A prescription medical supply sample dispensing transaction apparatus, comprising:
    a processor; and
    a memory disposed in communication with the processor and storing processor-executable instructions to:
    receive a prescription medical supply sample dispensing authorization request from a dispensing pharmacist,
    said prescription medical supply sample dispensing authorization request including information loaded from a portable consumer device storing a graphic image of the prescription medical supply sample and information of an electronic voucher;
    obtain an account identifier associated with the electronic voucher;
    send a verification request to an issuer of the electronic voucher to verify the account associated with the electronic voucher has been loaded with sufficient funds by a sponsor to pay for the requested drug sample distribution;
    send an authorization response to the dispensing pharmacist upon receipt of the verification from the issuer; and
    transact an amount to cover the requested prescription medical supply sample dispensing from the account associated with the electronic voucher to the dispensing pharmacist.

19. A processor-readable non-transitory medium storing processor-issuable instructions executable by a processor to:
receive a prescription medical supply sample dispensing authorization request from a dispensing pharmacist,
said prescription medical supply sample dispensing authorization request including information loaded from a portable consumer device storing a graphic image of the prescription medical supply sample and information of an electronic voucher;
obtain an account identifier associated with the electronic voucher;
send a verification request to an issuer of the electronic voucher to verify the account associated with the electronic voucher has been loaded with sufficient funds by a sponsor to pay for the requested drug sample distribution;
send an authorization response to the dispensing pharmacist upon receipt of the verification from the issuer; and
transact an amount to cover the requested prescription medical supply sample dispensing from the account associated with the electronic voucher to the dispensing pharmacist.

20. A portable consumer free sample redemption device, comprising:
a substrate having a surface with a first graphic image of a free product sample printed thereon;
a memory, in contact with the substrate, storing information including:
an identifier for the free product sample,
a quantity for the free product sample,
a sponsor company account for a selling merchant to charge a cost of the free product sample,
wherein the charge includes a payment to a selling merchant account to reimburse the selling merchant for the free product sample;
a second graphic image of the free product sample; and
an identifier for a coupon provider distributing the free product sample to a consumer.

* * * * *